(12) United States Patent
Rehnke

(10) Patent No.: US 7,780,690 B2
(45) Date of Patent: Aug. 24, 2010

(54) INSTRUMENTS AND METHOD FOR MINIMALLY INVASIVE CARPAL TUNNEL RELEASE

(75) Inventor: Robert D. Rehnke, St. Petersburg, FL (US)

(73) Assignee: ReCon Surgical, Inc., St. Petersburg, FL (US)

( * ) Notice: Subject to any disclaimer, the term of this patent is extended or adjusted under 35 U.S.C. 154(b) by 737 days.

(21) Appl. No.: 11/449,470

(22) Filed: Jun. 8, 2006

(65) Prior Publication Data

US 2007/0288043 A1 Dec. 13, 2007

(51) Int. Cl.
*A61B 17/32* (2006.01)

(52) U.S. Cl. .................... 606/170; 606/167; 600/104

(58) Field of Classification Search ......... 606/167–185, 606/190; 600/101–135, 160, 164, 170, 171, 600/173, 176; 604/264
See application file for complete search history.

(56) References Cited

U.S. PATENT DOCUMENTS

| | | | |
|---|---|---|---|
| 3,094,124 A * | 6/1963 | Birtwell ..................... 604/523 |
| 4,573,981 A * | 3/1986 | McFarlane ................. 604/263 |
| 4,962,770 A | 10/1990 | Agee et al. |
| 5,029,573 A | 7/1991 | Chow |
| 5,089,000 A | 2/1992 | Agee et al. |
| 5,179,963 A | 1/1993 | Berger |
| 5,269,796 A | 12/1993 | Miller et al. |
| 5,273,024 A | 12/1993 | Menon et al. |
| 5,282,816 A | 2/1994 | Miller et al. |
| 5,318,582 A | 6/1994 | Chow |
| 5,323,765 A | 6/1994 | Brown |
| 5,325,883 A | 7/1994 | Orr |
| 5,331,975 A | 7/1994 | Bonutti |
| 5,346,503 A | 9/1994 | Chow |
| 5,356,419 A | 10/1994 | Chow |
| 5,366,465 A * | 11/1994 | Mirza ......................... 606/170 |
| 5,387,222 A | 2/1995 | Strickland |
| 5,400,768 A * | 3/1995 | McNamara et al. ......... 600/104 |
| 5,443,474 A * | 8/1995 | Sfakianos et al. .......... 606/167 |
| 5,458,611 A | 10/1995 | Resnick et al. |
| 5,507,800 A | 4/1996 | Strickland |
| 5,545,136 A | 8/1996 | Berger |
| 5,569,283 A | 10/1996 | Green et al. |

(Continued)

OTHER PUBLICATIONS

David H. Palmer, MD et al; "Social and Economic Costs of Carpal Tunnel Surgery", American Academy of Orthopaedic Surgeons, 1995 7pgs.

(Continued)

*Primary Examiner*—Anhtuan T Nguyen
*Assistant Examiner*—Kathleen Sonnett

(57) ABSTRACT

Instruments for use in minimally invasive carpal tunnel release include a cannula and a cutting member movable longitudinally within the cannula to advance a cutting blade of the cutting member along a longitudinal slot in the cannula to sever a transverse carpal ligament disposed over the slot. A dilating member is provided for creating a subligamentous space to accommodate the cannula and/or for removing adhered synovium from a lower surface of the ligament. A method for minimally invasive carpal tunnel release involves establishing a subcutaneous pathway to the carpal tunnel from an incision in the forearm, introducing the cannula in the carpal tunnel via the pathway, and severing the transverse carpal ligament with the cutting blade of the cutting member, all of which steps are performed under direct endoscopic visualization.

20 Claims, 32 Drawing Sheets

U.S. PATENT DOCUMENTS

| | | | |
|---|---|---|---|
| 5,578,051 | A | 11/1996 | Mirza |
| RE35,523 | E | 6/1997 | Berger |
| 5,649,946 | A | 7/1997 | Bramlet |
| 5,651,790 | A | 7/1997 | Resnick et al. |
| 5,716,321 | A * | 2/1998 | Kerin et al. ................. 600/114 |
| 5,730,749 | A | 3/1998 | Battenfield |
| 5,735,865 | A * | 4/1998 | Schaumann et al. ......... 606/167 |
| 5,738,628 | A * | 4/1998 | Sierocuk et al. ............. 600/104 |
| 5,769,865 | A | 6/1998 | Kermode et al. |
| 5,827,312 | A | 10/1998 | Brown et al. |
| 5,908,431 | A | 6/1999 | Battenfield |
| 5,968,061 | A | 10/1999 | Mirza |
| 5,993,378 | A | 11/1999 | Lemelson |
| 6,096,026 | A * | 8/2000 | Schultz .......................... 606/1 |
| 6,179,852 | B1 | 1/2001 | Strickland et al. |
| 2003/0023260 | A1 | 1/2003 | Bonutti |
| 2004/0143280 | A1 | 7/2004 | Suddaby |
| 2004/0267243 | A1 | 12/2004 | Klotz et al. |
| 2004/0267253 | A1 | 12/2004 | Klotz et al. |
| 2005/0038423 | A1 | 2/2005 | Makin et al. |

OTHER PUBLICATIONS

Robert H. Ablove, MD et al; "Morphologic Changes Following Endoscopic and Two- portal Subcutaneous Carpal Tunnel Release"; Journal of Hand Surgery,vol. 19A, No. 5, Sep. 1994.

David H. Palmer et al; "Endoscopic Carpal Tunnel Release: A Comparison of Two Techniques with Open Release" Journal of Arthroscopic and Related Surgery, 1995, pp. 498-508.

Ulrich Lanz, MD; "Anatomical variations of the median nerve in the carpal tunnel"; The Journal of Hand Surgery, Jan. 1977, vol. 2 No. 1 pp. 44-53.

Ulrich Lanz, MD; "Anatomical variations of the median nerve in the carpal tunnel"; Internet article, Apr. 18, 2006; 1 page.

Scott D. Boden, MD et al; "An AOA Critical Issue: The Future of the Orthopaedic Surgeon-Proceduralist or Keeper of the Musculoskeletal System?"; Journal of Bone and Joint Surgery, Dec. 2005, vol. 87, Issue 12, p. 2812,10 pgs (Internet).

Ichiro Okutsu et al, "Endoscopic Management of Carpal Tunnel Syndrome", Arthroscopy, vol. 5, No. 1, 1989, 8 pages.

Paul Cotton, Symptoms May Return After Carpal Tunnel Surgery, JAMA, Apr. 17, 1991, vol. 265, No. 15, 1 page.

Patrick Browning, "Carpal Tunnel Syndrome", Internet article, Jul. 2, 2004, 8 pages.

John M. Agee et al, "Endoscopic Carpal Tunnel Release: A Prospective Study of Complications and Surgical Experience", The Journal of Hand Surgery, 1995, 20A: 165-171.

Peter A. Feinstein, "Endoscopic carpal tunnel release in a community-based series", The Journal of Hand Surgery, 1993; 18A:451-4.

David F. Jimenez, et al, "Endoscopie treatment of carpal tunnel syndrome: a critical review", J. Neurosurg./vol. 88/ May, 1998, 10 pages.

Connie O'Kane, "Endoscopic Carpal Tunnel Release", Outpatient Surgery Magazine, Mar. 2006, 4 pages.

George S. Phalen, "The Carpal-Tunnel Syndrome", The Journal of Bone and Joint Surgery, vol. 48-A, No. 2, Mar. 1966, 18 pages.

Michael Feuerstein et al, "Clinical Management of Carpal Tunnel Syndrome: A 12-Year Review of Outcomes", American Journal of Industrial Medicine 35:232-245 (1999).

Robert A. Weber et al, "Consecutive Versus Simultaneous Bilateral Carpal Tunnel Release", Annals of Plastic Surgery, vol. 54, No. 1, Jan. 2005, 5 pages.

Robert A. Weber, MD et al; "Consecutive Versus Simultaneous Bilateral Carpal Tunnel Release"; Annals of Plastic Surgery; vol. 54, No. 1, Jan. 2005, 5 pgs.

David T. Netscher, MD; "The Benefit of Transverse Carpal Ligament Reconstruction following Open Carpal Tunnel Release"; from the Division of Plastic Surgery, Baylor College of Medicine, and Plastic Surgery Service, Dept. of Vertans Affair Medical Center, Oct. 3, 2002, 3 pgs.

Richard Chapell, Ph.D. et al; Poor Outcome for Neural Surgery (Epineurotomy or Neurolysis) for Carpal Tunnel Syndrome Compared with Carpal Tunnel Release Alone: A Meta-analysis of Global Outcomes; Fro ECRI; May 30, 2002, Nov. 19, 2002, 8 pgs.

Rodney I. MacDonald et al; "Complications of surgical release for carpal tunnel syndrome"; The Journal of Hand Surgery; Jan. 1978, 7 pgs.

Dean S. Louis, M.D. et al; "Complications of carpal tunnel surgery"; J. Neurosurg. vol. 62, Mar. 1985, 5 pgs.

Michael I. Kulick, D.D.S., MD et al; "Long-term analysis of patients having surgical treatment for carpal tunnel syndrome"; The Journal of Hand Surgery, Apr. 29, 1985, 8 pgs.

S. Rojviroj et al; "Pressures in the Carpal Tunnel"; The Journal of Bone and Joint Surgery (Br) 1990; 72-B; pp. 516-518.

Richard H. Gelberman, M.D. et al; "The Carpal Tunnel Syndrome—A Study of Carpal Canal Pressures"; The Journal of Bone and Joint Surgery; vol. 63-A, No. 3, Mar. 1981; 4 pgs.

Ichiro Okutsu, M.D. et al; "Measurement of Pressure in the Carpal Canal before and after Endoscopic Management of Carpal Tunnel Syndrome"; Journal of Bone and Joint Surgery vol. 71 A, No. 5, Jun. 1989, 6 pgs.

Richard N. Hinrichs et al; "Creep Response of the Transverse Carpal Ligament in Cadavers: Application to Carpal Tunnel Syndrome"; Dept. of Exercise Science, Arizona State University, Tempe, AZ, 2 pgs.

Paul G. Kiritsis, BS et al; "Biomechanical Changes After Carpal Tunnel Release: A Cadaveric Model for Comparing Open, Endoscopic, and Step-cut Lengthening Techniques"; Journal of Hand Surgery 1995; 20A:173-180.

Harris Gellman, MD. et al; "Analysis of pinch and grip strength after carpal tunnel release"; The Journal of Hand Surgery 1989; 14A: 863-864.

S.C. Kline et al; "The Transverse Carpal Ligament"; The Journal of Bone and Joint Surgery, vol. 74-A, No. 10, Dec. 1992, 6 pgs.

Dean S. Louis, MD, "Commentary: Progress?—At What Price?", The Journal of Hand Surgery, 1 page.

Mitchell B. Rotman, MD et al, "Anatomic relationships of an endoscopic carpal tunnel device to surrounding structures", Journal of Hand Surgery, 1993; 18A: 442-50.

Kenneth H. Duncan, M.D. et al, "Treatment of carpal tunnel syndrome by members of the american Society for Surgery of the Hand: Results of a questionnaire", The Journal of Hand Surgery, 1987; 12A: 384-391.

A.C.F. Hui et al, "A randomized controlled trial of surgery vs steroid injection for carpal tunnel syndrome", Neurology 64, Jun. 2005, 5 pgs.

Clifton L. Gooch, MD et al, "Treatment of carpal tunnel syndrome—Is there a role for local corticosteroid injection?", Neurology 2005, 64: 2006-2007.

Douglas L. Forman, MD et al, "Persistent or Recurrent Carpal Tunnel Syndrome Following Prior Endoscopic Carpal Tunnel Release", The Journal of Hand Surgery, vol. 23A No. 6 Nov. 1998, 5 pgs.

Benjamin M. Sucher, DO et al, Manipulative Treatment of Carpal Tunnel Syndrome: Biomechanical and Osteopathic Intervention to Increase the Length of the Transverse Carpal.

Ligament: Part 2. Effect of Sex Differences and Manipulative 'Priming', Journal of American Osteopathic Association, vol. 105, No. 3, Mar. 2005, 9 pgs.

Editorial, "Thoughts on the technique of carpal tunnel release", The Journal of Hand Surgery, Nov. 1992, vol. 17A, No. 6, 2 pgs.

Richard A Brown et al, "Carpal Tunnel Release A Prospective Randomized Assessment of Open and Endoscopic Methods", Journal of Bone and Joint Surgery, vol. 75-A, No. 9, 1993.

Achilleas Thoma et al, A Meta-Analysis of Randomized Controlled Trials Comparing Endoscopic and Open Carpal Tunnel Decompression, Plastic and Reconstructive Surgery, Oct. 2004, 10 pgs.

Lee Berger, "Balloon Carpal Tunnel Plasty: First Comparative Clinical Study", Pittsburgh Orthopaedic Journal, Hand Research Laboratory, 2 pgs.

Thomas E Trumble et al, "Single-Portal Endoscopic Carpal Tunnel Release Compared with Open Release", The Journal of Bone and Joint Surgery, Incorporated, vol. 84-A, No. 7 Jul. 2002, 9 pgs.

Rodney E. Schmelzer et al, "Endoscopic Carpal Tunnel Release: A Review of 753 Cases in 486 Patients", Plastic and Reconstructive Surgery, Jan. 2006, 9 pgs.

Internet article, "Endoscopic treatment of carpal tunnel syndrome: a critical review", 5 pgs.

* cited by examiner

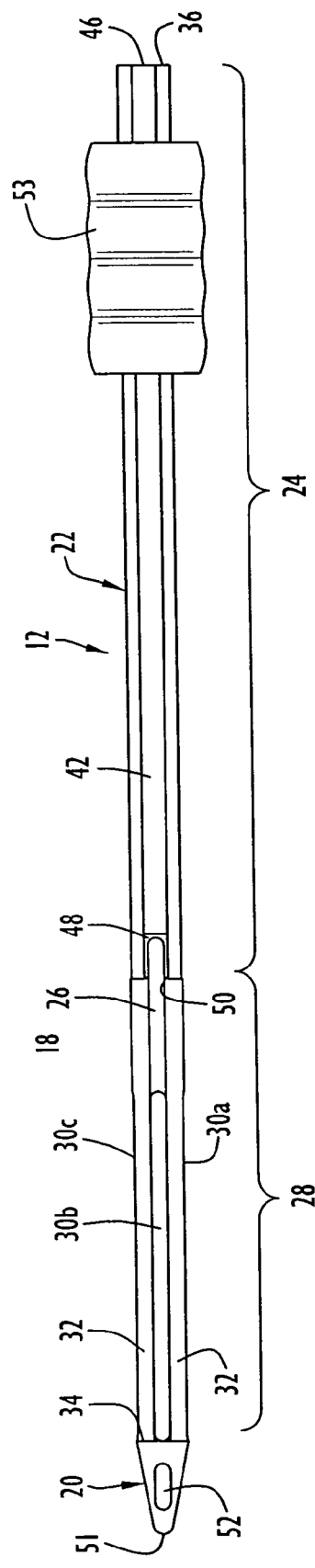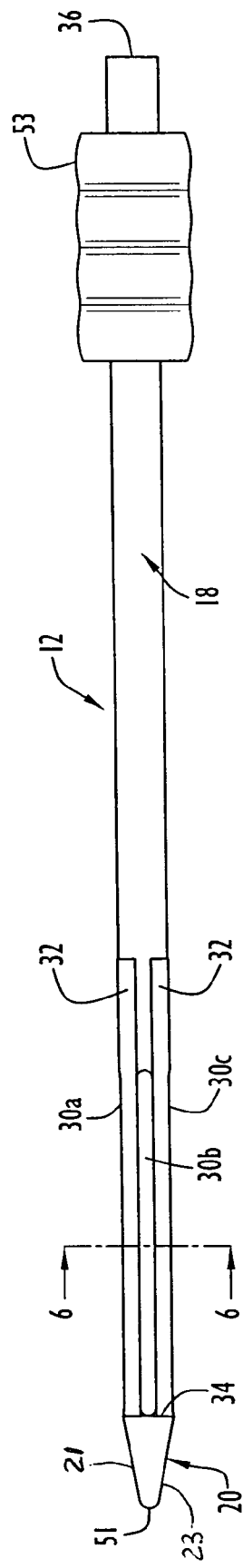
FIG.3
FIG.4

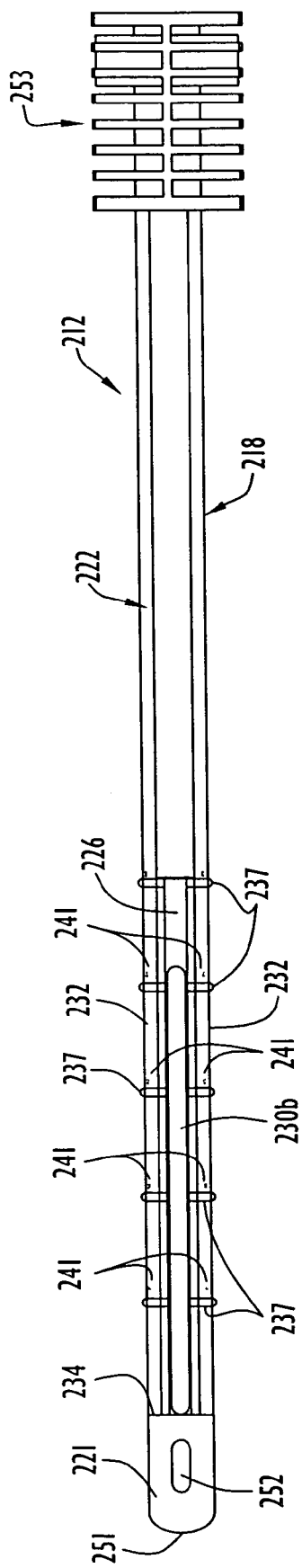
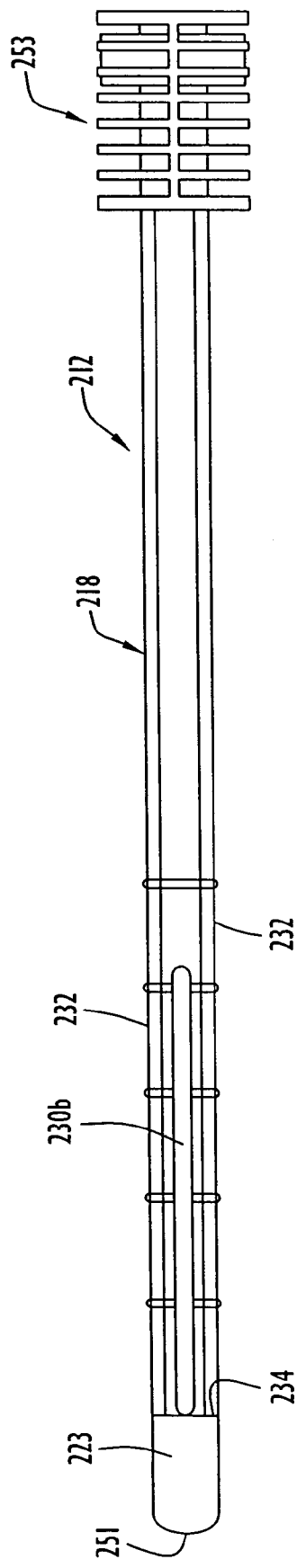
FIG.16
FIG.17

INSTRUMENTS AND METHOD FOR MINIMALLY INVASIVE CARPAL TUNNEL RELEASE

BACKGROUND OF THE INVENTION

1. Field of the Invention

The present invention relates to instruments and methods for carpal tunnel release and, more particularly, to instruments and methods for minimally invasive carpal tunnel release wherein the transverse carpal ligament is accessed via a relatively small size incision and is divided with the assistance of endoscopic visualization.

2. Brief Discussion of the Related Art

Carpal tunnel syndrome is a commonly occurring medical condition arising from compression of the median nerve passing through the carpal tunnel of the wrist. Carpal tunnel syndrome is associated with various problematic symptoms including numbness, tingling, loss of sensation, pain which may be localized to the hand and which may radiate to the elbow, shoulder or neck of the patient, reduced grip strength, loss of muscle function, muscle atrophy, and loss of sleep due to nocturnal symptoms.

Various conditions may cause and/or aggravate carpal tunnel syndrome including non-specific flexor tenosynovitis, aberrant anatomy, injury, infection, inflammatory disease, metabolic disorders, intraneural hemorrhage, intrinsic enlargement of the volume of anatomical structures within the carpal tunnel, extrinsic compression of anatomical structures within the carpal tunnel, strenuous use of the hand and wrist, and repetitive motion of the hand and wrist. Carpal tunnel syndrome is one of the most common repetitive use injuries encountered in working adults and is being encountered with increasing frequency in younger age groups. Carpal tunnel syndrome oftentimes occurs bilaterally in a patient.

The carpal tunnel is defined by a concave arrangement of the wrist bones spanned on the volar or palmar aspect of the wrist by the flexor retinaculum, an essentially rigid ligament also known as the transverse carpal ligament. A distal portion of the ligament attaches to the hook of the hamate and to the ridge of the trapezium. A proximal portion of the ligament attaches to the pisiform and to the scaphoid tubercle. The transverse carpal ligament may be considered to define the roof of the carpal tunnel, with the floor and sides thereof being defined by the concave arrangement of the wrist bones. The carpal tunnel is a narrow space of essentially fixed size through which numerous important anatomical structures pass including the median nerve and various tendons. The median nerve passes through the carpal tunnel from the forearm and branches out distally to provide sensory enervation to the thumb, index finger, middle finger, and a portion of the ring finger. A motor branch of the median nerve supplies the thenar muscles that control movement of the thumb into opposition with the other fingers of the hand. The flexor digitorum superficialis tendons and the flexor digitorum profundis tendons pass through the carpal tunnel and are covered by a common synovial sheath. The flexor pollicis longus tendon passes through the carpal tunnel and is contained in its own synovial sheath. The synovium promote gliding of the tendons in conjunction with flexion and extension of the fingers. The median nerve is located in the carpal tunnel just under the transverse carpal ligament and over the synovial sheath containing the flexor digitorum tendons. In some atypical cases, an anomalous motor branch of the median nerve is present in the carpal tunnel or in the transverse carpal ligament.

Other important and sensitive anatomical structures or tissue in the vicinity of the carpal tunnel include the ulnar and radial arteries, the superficial palmar arterial arch, the ulnar and digital nerves, palmar aponeurosis, palmaris longus, abductor pollicis, and flexor carpi radialis. In addition to defining the roof of the carpal tunnel, the transverse carpal ligament defines the floor of the Guyon tunnel, which has the palmar carpal ligament as its volar boundary. The ulnar nerve and ulnar artery pass through the Guyon tunnel. The ulnar artery and nerve lie superficial to the transverse carpal ligament within the deep fascia overlying the transverse carpal ligament along the volar or palmar aspect of the wrist. The superficial fascia, in turn, overlies the deep fascia along the volar or palmar aspect of the wrist. Distal and proximal flexion creases are present in the skin along the volar aspect of the wrist, and the deep and superficial fascia are more tightly interconnected to one another at these flexion creases than are the deep and superficial fascia along the volar aspect of the forearm. The distal flexion crease normally demarcates the proximal boundary of the transverse carpal ligament. The distal boundary of the transverse carpal ligament is normally demarcated by Kaplan's cardinal line which courses from the hook of the hamate to the ulnar base of the thumb.

Non-surgical treatments for carpal tunnel syndrome, including rest, immobilization and anti-inflammatory medications, are not successful in relieving symptoms in a high percentage of cases. Consequently, surgical treatment known as carpal tunnel release, wherein the transverse carpal ligament is divided, transected or severed, is the treatment of choice in many cases of carpal tunnel syndrome. By completely severing the transverse carpal ligament, additional space is provided in the carpal tunnel to relieve pressure on the median nerve while retaining essentially normal wrist function in the patient.

Carpal tunnel release has traditionally been performed as an open surgical procedure requiring a long, deep incision through the skin and underlying anatomical structures or tissue extending from the wrist to mid-palm in order to expose the transverse carpal ligament. In open procedures, therefore, it is ordinarily necessary to divide or incise the palmaris brevis muscle, palmar fascia, thenar and hypothenar muscle fibers, fat and nerve fibers. There are many drawbacks to open surgical procedures for carpal tunnel release including considerable post-operative pain, increased risk of infection, long recovery times in which use of the hand is greatly curtailed, the need for the patient to wear immobilizing devices such as splints, unsightly scarring, loss of grip and pinch strength, the potential for inadvertent injury to nearby anatomical structures such as the palmar cutaneous nerve, and losses due to missed work. It is not unusual for patients recovering from open carpal tunnel release surgery to be unable to engage in normal employment or other routine activities for up to four to six weeks. The drawbacks associated with open carpal tunnel release surgery tend to be exacerbated in procedures involving palmar incisions on account of the highly specialized and sensitive nature of the skin and anatomical tissue in the area of the palm. However, any incision in the wrist at or close to a flexion crease is undesirable. Incisions that cross a flexion crease may result in undesirable complications including undesired tension on the incision line and hypertrophic scar formation. Incisions at or close to a flexion crease also result in greater pain for the patient due to this area being an anatomical joint subjected to frequent movement.

Some open surgical procedures for carpal tunnel release avoid a palmar incision by gaining access to the transverse carpal ligament from a transverse wrist incision proximal to the carpal tunnel. However, such procedures typically involve "blind" cutting of the transverse carpal ligament, thusly presenting a greater risk of inadvertent injury to nearby important anatomical structures as well as the risk that the transverse carpal ligament will not be completely severed. Moreover, in surgical procedures where a deep incision, even a transverse one, is made in the volar aspect of the wrist through the skin and underlying tissue, there is still a heightened risk of inadvertent injury and other complications for the patient because of the specialized and sensitive important anatomical structures and tissue in this area of the wrist.

It has been proposed to perform carpal tunnel release as a minimally invasive or endoscopic surgical procedure in which the transverse carpal ligament is accessed and severed using instruments introduced through a relatively small size incision and assisted by remote or endoscopic visualization. Minimally invasive carpal tunnel release provides many advantages over open surgical procedures including smaller incisions with less trauma and scarring for the patient, less pain and shorter recovery times for the patient, reduced risk of infection, the ability for the patient to begin using the hand and to return to employment and other normal activities sooner after the surgery, and a reduction in the need for immobilizing devices such as splints. Various instruments and methods for minimally invasive carpal tunnel release are represented by U.S. Pat. No. 5,968,061, U.S. Pat. No. 5,578,051 and U.S. Pat. No. 5,366,465 to Mirza, U.S. Pat. No. 5,908,431 and U.S. Pat. No. 5,730,749 to Battenfield, U.S. Pat. No. 5,651,790 and U.S. Pat. No. 5,458,611 to Resnick et al, U.S. Pat. No. 5,356,419, U.S. Pat. No. 5,346,503, U.S. Pat. No. 5,318,582 and U.S. Pat. No. 5,029,573 to Chow, U.S. Pat. No. 5,325,883 to Orr, U.S. Pat. No. 5,323,765 to Brown, U.S. Pat. No. 5,282,816 and U.S. Pat. No. 5,269,796 to Miller et al, U.S. Pat. No. 5,273,024 to Menon et al, U.S. Pat. No. 5,089,000, U.S. Pat. No. 4,963,147 and U.S. Pat. No. 4,962,770 to Agee et al, and by Okutsu et al in "Endoscopic Management of Carpal Tunnel Syndrome", Arthroscopy: The Journal of Arthroscopic and Related Surgeries, Vol. 5(1), pages 11-18 (1989). Despite the benefits of minimally invasive or endoscopic procedures, prior instruments and methods for endoscopic carpal tunnel release have all too frequently resulted in various complications including injury to the superficial palmar arch, tendon lacerations, nerve injuries, incomplete release of the transverse carpal ligament, recurrence of symptoms, hematomas, and reflex sympathetic dystrophy. In many prior methods of endoscopic carpal tunnel release, the median nerve cannot be identified endoscopically with confidence or certainty, thereby creating reluctance on the part of many surgeons to perform carpal tunnel release as a minimally invasive procedure despite the benefits to be derived therefrom.

The minimally invasive procedure described in the Okutsu et al article is a single portal technique that involves forming an incision at the forearm, but still close to the flexion creases, inserting an obturator through the incision and into the carpal tunnel from the radial side of the palmaris longus tendon, removing the obturator and inserting a tube or sheath through the incision and into the carpal tunnel, and advancing an endoscope in the sheath to visualize the median nerve, flexor tendons and transverse carpal ligament. The sheath has a beveled distal end and is transparent to allow the endoscope to visualize the operative site through the wall of the sheath. Since the endoscope is not introduced until after formation of the incision, insertion of the obturator into the carpal tunnel and then insertion of the sheath into the carpal tunnel, the Okutsu et al procedure involves blind insertion of various instruments into the carpal tunnel and presents various opportunities for unintentional injury to critical anatomical structures before endoscopic visualization is established. Before the transverse carpal ligament is severed in the procedure described in the Okutsu et al article, the endoscope and sheath are removed and reinserted into the carpal tunnel on the ulnar side of the palmaris longus tendon. In a modified version of the procedure, the endoscope is initially inserted on the ulnar side of the palmaris longus. A hook knife is introduced into the carpal tunnel along the ulnar side of the sheath, and the median nerve is protected merely by retracting it away from the knife using the sheath. The knife is moved proximally to cut the transverse carpal ligament from its distal edge to its proximal edge, and the endoscope is simultaneously moved proximally within the sheath to visualize the cutting. The cutting performed with the knife is essentially freehand since the knife, and the sheath for that matter, are free to rotate or otherwise deviate out of position. It is thusly difficult to control the depth of the cut as well as the cutting location on the ligament. The ability to protect the median nerve depends on being able to hold the sheath in a position where it retracts the nerve away from the knife. Given the small size of the carpal tunnel, even small positional deviations of the instruments risk injury to important anatomical structures. It is also possible in the Okutsu et al procedure for the endoscopic image to be distorted due to visualization through the curved clear wall of the sheath. Furthermore, the need to move two separate instruments, i.e. the knife and the endoscope, independently but at the same time makes execution of the Okutsu et al procedure awkward and difficult as well as increases the potential for positional deviations of the instruments.

Another single portal endoscopic procedure in which the transverse carpal ligament is cut from distal to proximal and instruments for use in such procedure are exemplified by the Orr patent (U.S. Pat. No. 5,325,883). Orr provides a cannula for receiving an endoscope and a knife together therein. The cannula is a cylindrical tube, preferably made of metal, having an open proximal end and a closed blunt distal end defined by a convex distal end surface in union with the outer circumference of the tube. The cannula has a single slot therein beginning at its open proximal end and extending to its closed distal end. The slot allows the knife to access the transverse carpal ligament for cutting and allows the endoscope to visualize the cutting procedure from within the cannula. In the method of carpal tunnel release described by Orr, a transverse skin incision is made in the wrist 1 cm proximal to the volar flexion crease, and the incision is deepened by blunt dissection. A series of dilators of increasing diametric size are consecutively passed through the incision and into the carpal tunnel to create space for the cannula. An elevator is passed into the carpal tunnel and is used to separate the synovium from the underside or deep surface of the transverse carpal ligament. After these steps have been completed, the cannula is introduced into the carpal tunnel with the slot directed against the underside or deep surface of the ligament, and thereafter the endoscope is inserted in the cannula to visualize the ligament. Accordingly, all of the steps performed prior to introduction of the endoscope are performed blindly and unassisted by endoscopic visualization. After the distal margin of the ligament is identified using a hooked probe inserted in the cannula, the knife is inserted in the cannula and used to cut the ligament from its distal edge to its proximal edge while being visualized with the endoscope. Orr shows there to be a considerable amount of unoccupied space within the cannula when the endoscope and the knife are received together therein such that the endoscope and the knife are each free to move or deviate out of position within the cannula. Extension of the knife blade from the slot to cut through the ligament the proper depth is not controlled other than by the visualization provided by the endoscope. Moreover, the thickness of the slot is shown as being many times larger than the width of the knife blade such that the location of the knife blade within the slot width and, therefore, the cutting location on the ligament, is also not controlled other than by endoscopic visualization. In addition, it is difficult in the Orr procedure, and in other procedures that utilize a cannula or sheath of uniformly round external cross-section, to maintain alignment of the knife with a desired cutting location on the ligament because the uniformly round external cross-section of the cannula makes it especially prone to rotate. Despite the knife blade being contained in the slot while cutting the ligament, the lack of positional control over the instruments makes the cutting performed in the Orr procedure very similar to freehand cutting.

The endoscopic methods and instruments of the Agee et al patents (U.S. Pat. Nos. 4,962,770, 4,963,147 and 5,089,000) also relate to single portal carpal tunnel release involving distal to proximal cutting of the transverse carpal ligament. Agee et al provide a probe including a hollow sheath having a lateral aperture and having a closed blunt distal end terminating at a flat, angled distal end wall. A working tool comprising a pivotable cutting blade connected to a hollow shaft is received in the probe, the shaft being incrementally movable longitudinally within the probe via operation of a trigger grip to pivot the blade from a position where the blade is enclosed within the probe to a position where the blade is radially extended from the probe to project through the lateral aperture. A sight tube of an optical system is received in the shaft of the working tool, and is extended from a distal end of the shaft to provide visualization through the lateral aperture in the probe. The method of carpal tunnel release disclosed by Agee et al involves forming an incision proximal to but in close proximity to the carpal tunnel, continuing the incision through the deep fascia and the finger flexor synovium, and placing the wrist in extension to expose the proximal entry into the carpal tunnel, all of which steps are performed blindly since the probe and sight tube are not yet employed in the procedure. After the proximal entry into the carpal tunnel has been exposed, the probe is inserted through the incision and moved through the carpal tunnel to the distal edge of the transverse carpal ligament. The sight tube within the probe allows visualization of the anatomy within the carpal tunnel through the lateral aperture. The blade is extended from the lateral aperture to enable contact with the distal edge of the transverse carpal ligament. In order to cut the ligament from distal to proximal, the entire probe, with the working tool and sight tube received therein, is moved proximally. The cutting movement is repeated from distal to proximal as many passes or times as necessary to obtain complete division of the ligament. However, since the entire probe is moved from distal to proximal for each cutting movement or pass, it is difficult to return the probe to its previous distal position in order to obtain an endoscopic view of the cut already made in the ligament and/or to continue the cutting movement along the previously established cutting line. The instrumentation provided by Agee et al is bulky, difficult to maneuver with precision or accuracy, and provides limited endoscopic visualization through the lateral aperture of the probe.

The Menon et al patent (U.S. Pat. No. 5,273,024) pertains to a single portal endoscopic surgical procedure for carpal tunnel release in which an obturator is introduced in the carpal tunnel via a wrist incision, and is then removed and replaced with a series of increasingly larger dilators to prepare a space for insertion of a cannula/obturator assembly. The cannula/obturator assembly comprises a cannula of D-shaped interior cross-section and an obturator received within the cannula. The cannula has a closed blunt distal end and has a longitudinal slot extending from a point adjacent the distal end to a point adjacent an open proximal end of the cannula. After the distal end of the cannula/obturator assembly has been placed approximately at the distal margin of the transverse carpal ligament, the obturator is removed from the cannula and an endoscope is inserted axially in the cannula to provide visualization of the transverse carpal ligament via the slot. Accordingly, the Menon et al procedure entails blind insertion of various instruments into the carpal tunnel prior to establishment of endoscopic visualization. The Menon et al procedure further entails retracting the endoscope proximally within the cannula so that room is created in the cannula distal of the endoscope for accommodation of a knife used to cut the transverse carpal ligament. The knife is maneuvered into the slot in the cannula at an oblique angle distal of the endoscope. The knife is moved distally along the cannula to cut the transverse carpal ligament from proximal to distal and, in order to visualize the cutting procedure, the endoscope must be moved distally within the cannula to follow behind the knife. A standard needle inserted in the palm at the distal border of the ligament serves as a marker for visualization by the endoscope to prevent the surgeon from cutting too deeply into the palm. In order to inspect the median nerve endoscopically, the entire cannula must be rotated so that the slot faces the median nerve.

A further alternative single portal endoscopic surgical procedure for carpal tunnel release and instruments therefor are embodied in the Mirza patents (U.S. Pat. Nos. 5,968,061, 5,578,051 and 5,366,465). The instruments disclosed by Mirza include a cannula having an open blunt distal end and a slot extending the length of the cannula, an obturator for being received in the cannula and having a rib for mating engagement with the slot, an endoscope for being received in the cannula, and a knife blade for being mounted to the distal end of the endoscope. The Mirza procedure involves making an incision in the palm, deepening the incision to expose the palmar fascia, identifying the distal edge of the transverse carpal ligament and dividing it for approximately 5-6 mm, dividing the palmar fascia longitudinally, and exposing the transverse carpal ligament, all of which steps are performed without endoscopic visualization. Thereafter, the hand is secured in hyperextension, and a dissector inserted through the incision is used to dissect the transverse carpal ligament from the synovium. The dissector is withdrawn and the cannula having the obturator received therein is advanced along the path previously established by the dissector, which step is again performed without endoscopic visualization. The obturator is then withdrawn from the cannula and replaced with the endoscope for visualization of the transverse carpal ligament. Once the transverse carpal ligament has been identified, the endoscope is withdrawn from the cannula and replaced with the same or a different endoscope that has the knife blade mounted thereto, the knife blade slidably engaging in the slot in the cannula. The endoscope with the knife blade mounted thereto is advanced in the cannula, and the knife blade is used to cut the transverse carpal ligament under endoscopic visualization. Because the endoscope and knife blade are attached to one another in fixed relative positions, the field of endoscopic view is also fixed in relation to the knife blade and the cutting performed therewith on the ligament. Upon completion of cutting, the endoscope is removed and replaced in the cannula by an endoscope without a knife blade in order to inspect the ligament and median nerve, which requires that the cannula be rotated to afford a broader field of view. The Mirza procedure is disadvantageous for its blind insertion of instruments, its limited field of endoscopic view prior to, during and subsequent to the cutting procedure, the need for insertion and withdrawal of many instruments, the lack of protection for the knife blade as the scope is distally advanced within the cannula prior to actual cutting, and the need for securement of the hand in hyperextension. In addition, even a small size palmar incision is undesirable given the specialized nature of the palmar tissue and the presence of critical anatomical structures in the area of the palm.

The Chow patents (U.S. Pat. Nos. 5,029,573, 5,318,582, 5,346,503 and 5,356,419) relate to a dual or two portal endoscopic surgical procedure for carpal tunnel release and to instruments therefor. The instruments utilized in the Chow procedure include a sheath, a trocar, and a plurality of cutting instruments. The sheath is an elongate tube having an open proximal end, an open beveled distal end, and a slot extending the full length of the tube. The slot mates with a prominence on the trocar, which slidably fits within the sheath, and also provides access to the operative site for the cutting instruments inserted in the sheath. The cutting instruments include a probe knife, a triangular knife and a retrograde knife. The procedure is initiated by forming an entry portal or incision through the skin and subcutaneous tissue of the wrist, followed by a longitudinal cut of the fascia to expose the ulnar bursa and flexor tendons. The sheath, with the trocar disposed therein, is inserted in the incision and is advanced distally beneath the transverse carpal ligament. Following this step in the procedure, the patient's hand is secured in hyperextension. Following hyperextension of the hand, the sheath and trocar are together advanced further distally to exit the hand through an exit portal or incision in the palm. The trocar is then withdrawn from the sheath. All of the steps performed up to this point are performed blindly and without endoscopic visualization. An endoscope is then inserted into either of the open distal or proximal ends of the sheath, and the probe knife is inserted into the end of the sheath opposite the endoscope. The probe knife is used to locate the distal or proximal edge of the transverse carpal ligament via the slot in the sheath and is used to make an initial stab cut in the edge of the ligament. The probe knife is withdrawn and replaced in the sheath by the triangular knife, which is used to cut the mid-section of the ligament. The triangular knife is withdrawn and the retrograde knife is inserted into the sheath. The retrograde knife is used to form a cut joining the stab cut to the mid-section cut to complete division of a distal or proximal portion of the ligament depending on whether the stab cut originated in the distal or proximal edge of the ligament. The remaining distal or proximal portion of the ligament is divided in a similar but reverse manner after removing the endoscope and inserting it into the opposite end of the sheath. In the Chow procedure, the location of the entry and exit portals and the path for blind advancement of instruments between these portals are determined from external anatomical landmarks. Undesirable complications may ensue in patient's with internal anatomical anomalies, such as unusual anatomical location of the superficial palmer arch artery or unusual positioning of the motor branch of the median nerve. Moreover, given the small confined space in which critical anatomical structures are located in the wrist, undesirable complications may result where the instruments deviate even a small amount from the prescribed path. Because the hand is secured in hyperextension, the median nerve and other important anatomical structures are at increased risk of injury since they too are held in an immovable position. Furthermore, it is difficult in the Chow procedure to accurately position each of the several cutting instruments at the proper location so that each of the separately formed cuts in the ligament combine to form a continuous complete cut through the ligament. Additional drawbacks of the Chow procedure are that two portals are required and these are undesirably located in the volar aspect of the wrist and in the specialized tissue of the palm. In the Chow procedure as well as in other endoscopic procedures that utilize an incision in the palm and/or an incision in the volar aspect of the wrist, the location(s) of the incision(s) gives rise to various disadvantages including increased pain and longer recovery times for the patient, higher risk of inadvertent injury to the patient, and greater risk of complications. The need for multiple separate cuts and cutting instruments in order to effectuate a complete cut of the transverse carpal ligament in the Chow procedure increases the cost of instrumentation for the procedure and also extends the duration of the procedure. Surgical procedures of longer duration translate into greater cost but even more importantly place the patient at greater risk.

The Miller et al patents (U.S. Pat. Nos. 5,282,816 and 5,269,796) and the Resnick et al patents (U.S. Pat. Nos. 5,651,790 and 5,458,611) relate to instruments and methods for two portal endoscopic surgical procedures for carpal tunnel release which, like the Chow procedure, require an entry portal in the wrist and an exit portal in the palm determined from external anatomical landmarks. In discussing the Chow procedure, Miller et al and Resnick et al consider it a drawback of the Chow procedure to retract the flexor tendons toward the radial side after incising the volar antebrachial fascia to expose the flexor tendons. Miller et al and Resnick et al believe that retraction of the flexor tendons places undue traction upon both the ulnar and median neurovascular structure and results in an increased incidence of postoperative median and ulnar nerve neuropraxiae. In addition, Miller et al and Resnick et al believe that the Chow procedure places the ulnar neurovascular structures at risk by requiring deep dissection into the carpal tunnel. In the procedure described by Miller et al, after the volar antebrachial fascia is incised to expose the flexor tendons, a cannula/obturator assembly is placed under the transverse carpal ligament using direct visualization, and gentle pressure is used to "walk" the assembly under the ligament. Miller et al provides a slotted cannula having an open distal end with a blunt, flat distal end surface, and provides an obturator for insertion in the cannula to form the cannula/obturator assembly. The slot in the cannula extends practically the entire length of the cannula. In reality, the cannula/obturator assembly is "walked" under the ligament in essentially a blind fashion due to the limited field of direct view distal to the assembly and due to there being no provision for endoscopic visualization at this point in the procedure. The obturator is removed from the cannula and replaced with an endoscope only after the cannula/obturator assembly has exited the palm at the exit portal, the endoscope being used to visualize the transverse carpal ligament through the slot. Cutting of the ligament involves multiple separate cuts and cutting instruments similar to the Chow procedure. The instruments and method of the Resnick et al patents are similar to those of the Miller et al patents. In addition to blind insertion of the cannula/obturator assembly through the carpal tunnel, the procedures described by Miller et al and Resnick et al have many of the same disadvantages as the Chow procedure.

The Brown patent (U.S. Pat. No. 5,323,765) describes a dual portal endoscopic procedure for carpal tunnel release that is essentially a modification of the Chow procedure and describes instruments for use in the procedure. As in the Chow procedure, the procedure of Brown involves blindly passing a cannula/obturator assembly under the transverse carpal ligament from an entry portal in the volar aspect of the wrist and through an exit portal in the palm. The cannula of the cannula/obturator assembly has an open, blunt distal end and a single longitudinal slot extending nearly the entire length of the cannula. The entry portal is located 0.5 to 1.5 cm proximal to the distal flexion crease and, preferably, is located in the proximal flexion crease. Prior to the cannula/obturator assembly being inserted in the entry portal, retractors are inserted to expose and raise the fascia, and an elevator is inserted to dissect the synovium from the transverse carpal ligament. After the distal end of the cannula has exited the exit portal, the obturator is removed from the cannula and an endoscope is introduced in the distal end of the cannula. The procedure is therefore performed blindly up to this point and gives rise to the disadvantages associated with blind entry into the carpal tunnel and blind insertion of instruments therein. A hooked knife introduced in the proximal end of the cannula is used to divide the transverse carpal ligament from distal to proximal in one continuous motion as the endoscope is simultaneously moved proximally within the cannula to follow the knife. Like some of the other endoscopic procedures discussed above, the Brown procedure is disadvantageous not only for its blind procedural steps but also for its palmar and wrist incisions, its need for separate instruments to be introduced in opposite ends of the cannula, its lack of positional control over the instruments in the carpal tunnel and over the cutting location on the transverse carpal ligament, its limited field of endoscopic view, and its need for simultaneous movement of the knife and the endoscope from opposite ends of the cannula.

The Battenfield patents (U.S. Pat. Nos. 5,908,431 and 5,730,749) pertain to instruments for use in dual portal endoscopic carpal tunnel release. The instruments disclosed by Battenfield include a cannula, preferably made of stainless steel, having an open diametrically narrowing distal tip terminating at a flat distal end surface and having a slot extending almost the entire length of the cannula. Other instruments disclosed by Battenfield include an obturator and a rasp for being received in the cannula. The rasp has a toothed segment that extends through the slot in the cannula. Battenfield mentions that an endoscope can be placed in the cannula but does not disclose that any other instrument can be present in the cannula along with the endoscope.

As seen from the above, prior methods of endoscopic carpal tunnel release propose to introduce instruments under the transverse carpal ligament in the subligamentous plane between the transverse carpal ligament and the flexor tendon synovial sheath. The insertion of instruments in the subligamentous plane between the transverse carpal ligament and the flexor tendon synovium sheath in endoscopic carpal tunnel release procedures is made more difficult due to the fact that wrist anatomy imparts an upward slope to the subligamentous plane in the distal direction. Conventional dilators and other conventional instruments used to enter the carpal tunnel in prior endoscopic carpal tunnel release procedures have distal end configurations which make it difficult to guide the instruments to follow the upward slope of the subligamentous plane. When these instruments are forwardly or distally advanced toward or beneath the transverse carpal ligament in a straight horizontal path or plane, the instruments commonly become obstructed, snagged or trapped in or by the synovium. In addition to increasing the complexity of the procedure and inflicting trauma on the patient, instruments that are obstructed, snagged or trapped by or in the synovium provide a poor vantage point for reliable endoscopic visualization of anatomical structures in the carpal tunnel because the clarity of the endoscopic image viewed through the synovium is distorted or impaired. Furthermore, some of the synovium will remain attached to the underside of the transverse carpal ligament which impairs endoscopic visualization of the ligament and the ability to identify the ligament with confidence.

In view of the deficiencies of prior instruments and methods for endoscopic carpal tunnel release, a need exists for improved instruments and methods for endoscopic carpal tunnel release which allow access to the carpal tunnel to be gained via a single portal located in the volar aspect of the forearm in an anatomically safe area, a considerable distance away from the flexion creases and other critical and sensitive anatomical structures and tissue in the more anatomically complex area of the wrist, which avoid a palmar incision as well as a wrist incision, which avoid the blind entry and insertion of instruments into the carpal tunnel, which allow introduction of a cannula into the carpal tunnel without an obturator or trocar disposed in the cannula, which enable entry into the carpal tunnel along the subligamentous plane between the transverse carpal ligament and flexor tendon synovium sheath, which provide enhanced endoscopic visualization, which provide a broader field of view of the operative site via an endoscope received in a cannula and without requiring that the cannula itself be rotated, which allow critical anatomical structures to be identified by endoscopic visualization with greater confidence and certainty, which provide improved positional stability of the instruments in the carpal tunnel while allowing relative displacement of adjacent anatomical structures, which avoid the need for securement of the wrist in hyperextension, which provide greater control and guidance over cutting of the transverse carpal ligament including the cutting location on the ligament as well as the depth of cut, which enable constant endoscopic visualization of the cutting procedure as well as improved visualization in the direction of cutting, which protect or shield the cutting blade when not intentionally deployed for cutting the transverse carpal ligament, which better ensure that the transverse carpal ligament will be completely divided, which avoid freehand cutting of the ligament, which increase the safety of endoscopic carpal tunnel release, which reduce the duration of endoscopic carpal tunnel release procedures, and which reduce the potential for surgeon error.

SUMMARY OF THE INVENTION

An instrument for use in minimally invasive carpal tunnel release includes a cannula and a cutting member receivable in the cannula. The cannula has an open proximal end, a closed distal tip, and a tubular member between the open proximal end and the distal tip. The tubular member has a central longitudinal axis, a proximal length portion, a distal length portion, a longitudinal interior passage in communication with the open proximal end for receiving the cutting member, and a longitudinal slot extending along the proximal and distal length portions in communication with the passage along a top of the cannula. The cannula further includes a blade housing extending longitudinally along the proximal length portion of the tubular member and enclosing an interior channel extending through the blade housing in communication with the slot. The slot along the distal length portion of the tubular member is positionable beneath a transverse carpal ligament to be severed, and a forward end of the blade housing may have a configuration to engage the ligament to hold it in place over the slot. The distal tip tapers distally in height from the tubular member to a distal terminus. In one configuration for the distal tip, the distal tip also tapers distally in width from the tubular member to the distal terminus. In other configurations for the distal tip, the distal tip does not taper distally in width from the tubular member to the distal terminus and may be of increased width along the distal terminus. The distal terminus may be in alignment with a horizontal plane containing the central longitudinal axis or may be offset from the horizontal plane toward the top of the cannula. The distal tip may have a window along the top of the cannula in communication with the interior passage. The slot in the tubular member along the top of the cannula is a volar slot, and the tubular member may have a dorsal slot along the bottom of the cannula and radial and ulnar slots along opposite sides of the cannula. The slots and window permit visualization therethrough by an endoscope received in the interior passage with or without the cutting member. The cannula may further include a plurality of exterior protuberances extending longitudinally along the tubular member at spaced radial locations about the central longitudinal axis. The protuberances may be arranged on the tubular member so that each protuberance is located between a pair of adjacently located slots. The cannula can have a plurality of interior ribs extending longitudinally along an inner surface of the tubular member to project into the interior passage. The distal length portion of the cannula may be provided with reference formations and indicia. It is preferred that the distal tip and at least the distal length portion of the tubular member be of transparent material.

The cutting member comprises an elongate tube slidably receivable in the interior passage of the cannula, a lumen extending entirely through the tube for receiving an endoscope, a cutting blade extending outwardly from the tube, and a longitudinal fenestration in the tube proximal of the cutting blade. The cutting blade extends through the volar slot of the cannula when the tube is slidably disposed in the passage and is moved longitudinally along the volar slot in response to longitudinal movement of the tube within the passage. The blade extends through the volar slot into the channel of the blade housing to be in a protected position when disposed longitudinally along the proximal length portion of the tubular member. The blade is extendable distally from the blade housing for distal movement along the volar slot along the distal length portion of the tubular member. Distal advancement of the blade from the blade housing exposes the blade to sever a transverse carpal ligament disposed over the volar slot along the distal length portion of the tubular member. The fenestration in the tube is a volar fenestration that comes into alignment with the volar slot of the cannula as the blade is extended distally from the blade housing, and permits endoscopic visualization therethrough by an endoscope within the lumen of the tube. The tube may be provided with a radial fenestration and an ulnar fenestration that come into respective alignment with the radial and ulnar slots of the cannula for endoscopic visualization therethrough in other directions by an endoscope received in the cutting member.

Another instrument for use in minimally invasive carpal tunnel release comprises a dilating member for creating and/or enlarging a subligamentous space beneath the transverse carpal ligament and/or for removing adhered synovium from the lower surface of the ligament. The dilating member comprises an open proximal end, a closed distal end, a tubular portion between the proximal and distal ends, a longitudinal interior passage in the tubular portion in communication with the open proximal end for receiving an endoscope, an aperture in the distal end along a top of the dilating member to permit visualization therethrough by an endoscope within the dilating member, and a plurality of elevated cutting edges extending longitudinally along the tubular portion. The distal end has an external configuration that tapers distally in height from the tubular portion toward the top of the dilating member to terminate at a leading edge extending transverse to a central longitudinal axis of the dilating member. The distal tip may be of increased width along the leading edge. The cutting edges may be disposed on upper surfaces of raised ridges extending longitudinally along the tubular portion with a depression between the ridges. It is preferred that the distal end and at least the part of the tubular portion that has the cutting edges thereon be made of transparent material. The dilating member is introduced in the carpal tunnel from proximal to distal along the subligamentous plane between the transverse carpal ligament and the flexor tendon synovial sheath. The distal end configuration of the dilating member facilitates insertion of the dilating member along the upward slope of the subligamentous plane while gently separating the flexor tendon synovial sheath from the transverse carpal ligament. The dilating member is inserted along the subligamentous plane with the cutting edges extending in the same direction as the width of the transverse carpal ligament. By placing the cutting edges in contact with the lower surface of the ligament and rotating the dilating member about its central longitudinal axis, adhered synovium is removed or abraded from the lower surface of the transverse carpal ligament and may collect in the depression for removal from the operative site when the dilating member is withdrawn. The aperture in the distal end of the dilating member as well as the transparency of the distal end and tubular portion permits endoscopic visualization therethrough by an endoscope received in the dilating member.

A method for minimally invasive carpal tunnel release involves formation of a small size access incision along the volar aspect of the forearm proximally well away from the wrist to be operated on, dissection of the superficial fascia from the deep fascia of the forearm distally toward the wrist under endoscopic visualization, and establishment of a proximal entry into the carpal tunnel by dissection performed under endoscopic visualization. A subcutaneous pathway leading from the incision into the carpal tunnel is thusly established for the subsequent introduction of instruments. Prior to inserting any instruments in the carpal tunnel, however, it is preferred that important anatomical structures including the transverse carpal ligament, median nerve and flexor tendons be located and identified via endoscopic visualization. A distal length portion of a cannula is introduced into the carpal tunnel via the incision and pathway under endoscopic visualization. The cannula is distally advanced in the carpal tunnel along the subligamentous plane between the transverse carpal ligament and flexor tendon synovial sheath under endoscopic visualization. It is desirable at this point to carry out endoscopic visualization via an endoscope within the cannula viewing through a window in a distal tip of the cannula and/or through one or more longitudinal slots in the cannula. A volar slot in the cannula is positioned to face the lower surface of the transverse carpal ligament, with the width of the ligament between its proximal edge and its distal edge disposed over the volar slot. A cutting member slidably received in the cannula is moved longitudinally distally within the cannula to move a cutting blade of the cutting member longitudinally distally along the volar slot to sever or cut the transverse carpal ligament from its proximal edge to its distal edge. Severing the ligament is visualized by an endoscope within the cutting member, which visualization may be obtained through a fenestration in the cutting member that is in alignment with the volar slot of the cannula. Endoscopic visualization may also be obtained in other directions through a window in the distal tip of the cannula and/or additional fenestrations in the cutting member that are in respective alignment with additional slots in the cannula. Once the transverse carpal ligament has been severed, the endoscope and cutting member may be removed from the cannula and the endoscope alone inserted in the cannula to perform endoscopic visualization through a window and/or one or more longitudinal slots in the cannula. Prior to introducing the cannula in the carpal tunnel, a subligamentous space may be created and/or enlarged to accommodate the cannula. Creation and/or enlargement of a subligamentous space may be accomplished by introducing a dilating member along the subligamentous plane to separate the flexor tendon synovial sheath from the transverse carpal ligament by gently displacing the flexor tendon synovial sheath downwardly away from the transverse carpal ligament as the dilating member follows the upward slope of the subligamentous plane. Adhered synovium may be removed from the lower surface of the transverse carpal ligament by moving cutting edges on the dilating member against the lower surface of the transverse carpal ligament.

Various objects, benefits and advantages of the present invention will become apparent from the following description of preferred embodiments of the invention taken in conjunction with the accompanying drawings wherein like reference numerals refer to like or similar parts.

BRIEF DESCRIPTION OF THE DRAWINGS

FIG. 3 is a top view of an outer member, sheath or cannula of the cutting and visualization instrument assembly.

FIG. 4 is a bottom view of the cannula.

FIG. 16 is a top view of a cannula of the preferred cutting and visualization instrument assembly.

FIG. 17 is a bottom view of the cannula of the preferred cutting and visualization instrument assembly.

DESCRIPTION OF THE PREFERRED EMBODIMENTS

Figure 1:
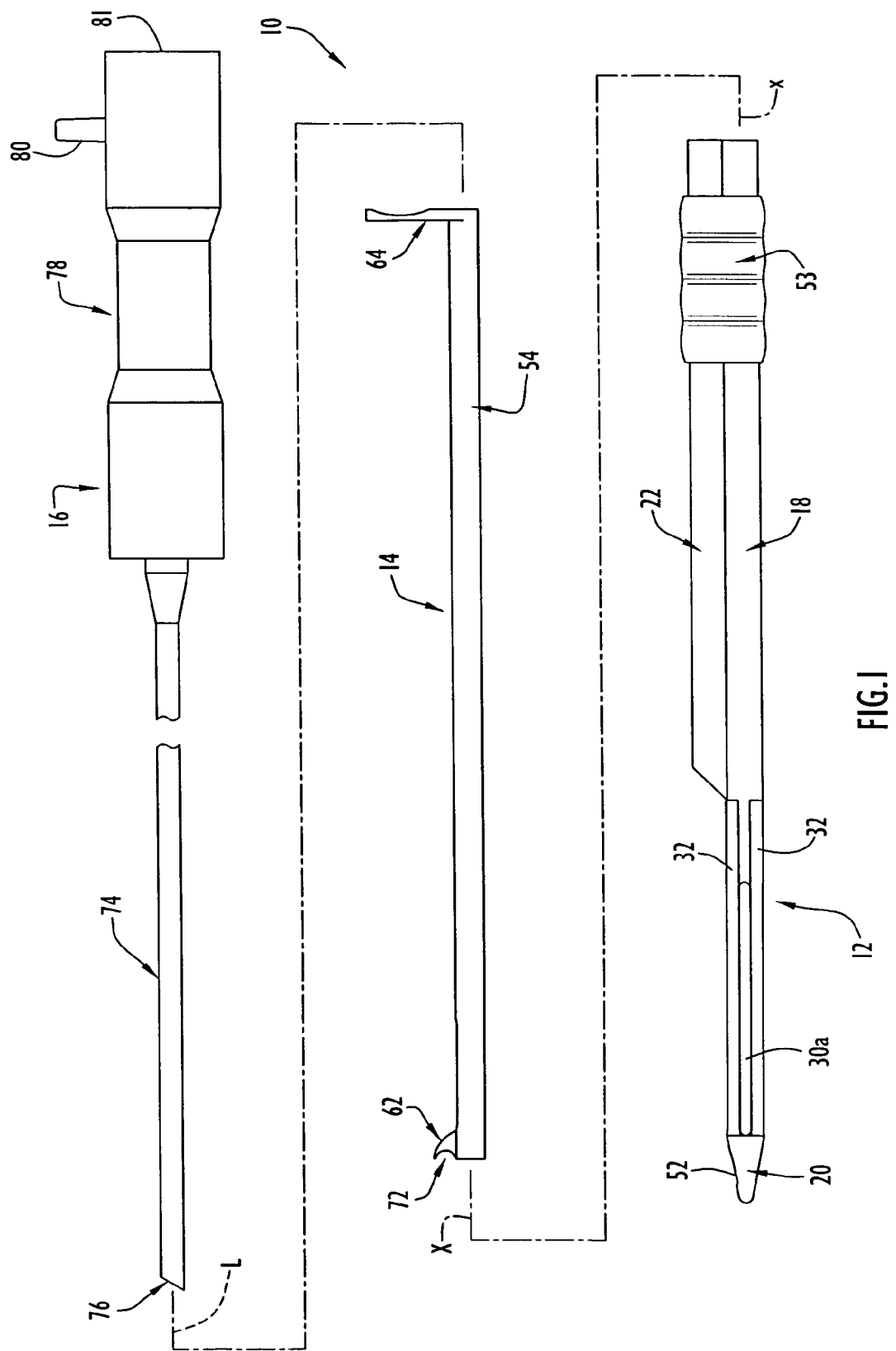
FIG. 1 is an exploded or unassembled side view of a cutting and visualization instrument assembly for use in endoscopic carpal tunnel release.
Figure 2:
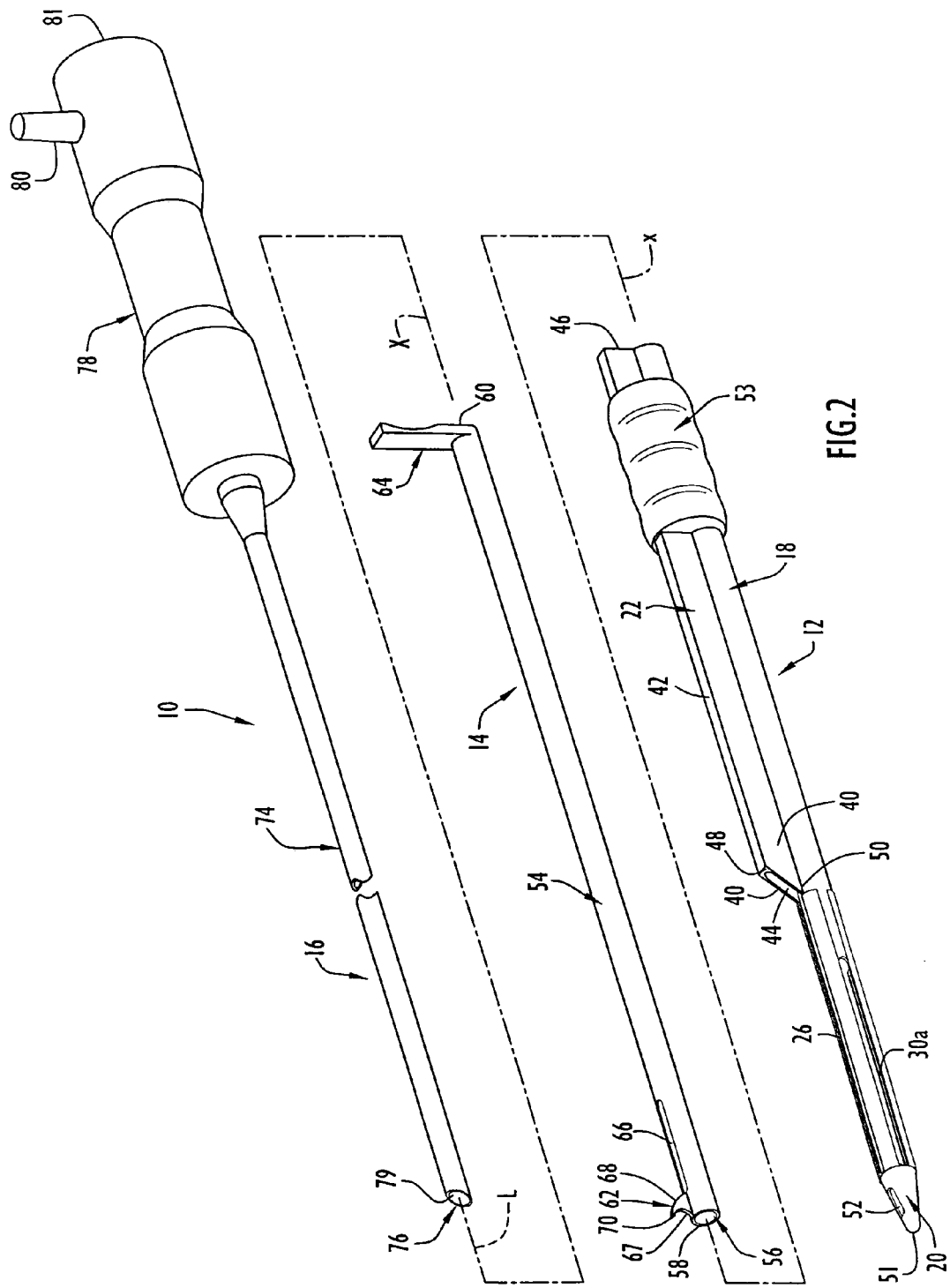
FIG. 2 is an exploded or unassembled perspective view of the cutting and visualization instrument assembly.
Figure 5:
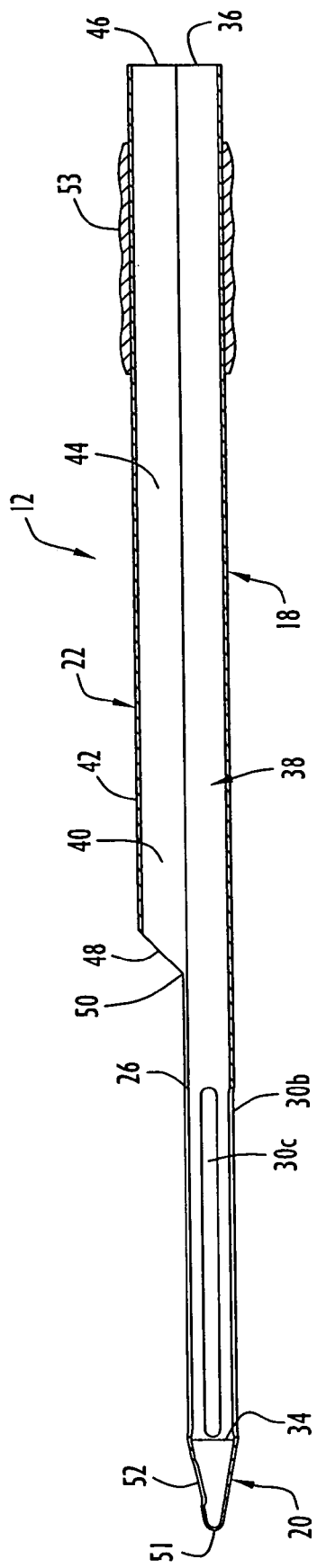
FIG. 5 is a longitudinal sectional view of the cannula.
Figure 8:
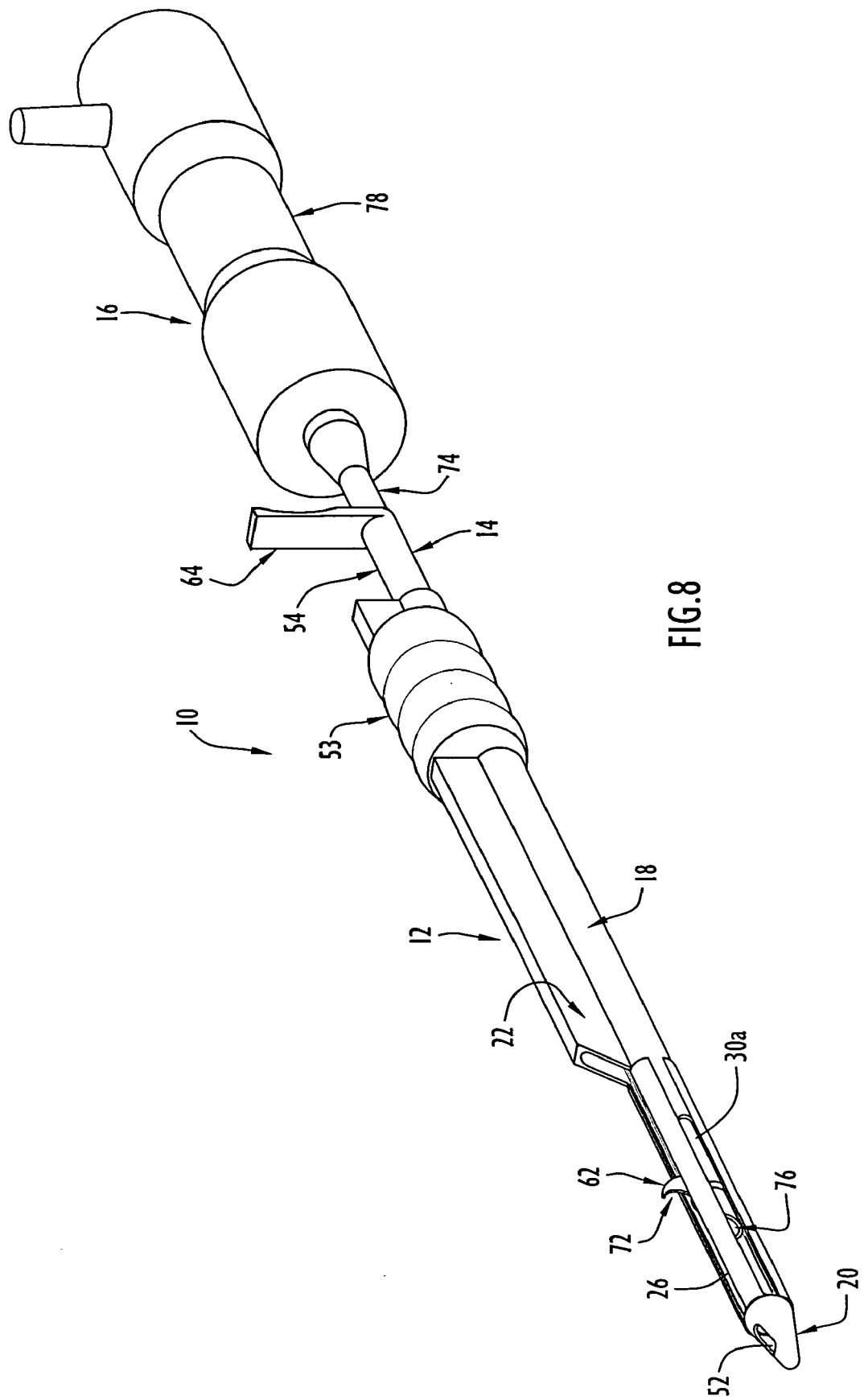
FIG. 8 is a perspective view of the cannula, the cutting member and an endoscope of the cutting and visualization instrument assembly shown in an assembled condition for the cutting and visualization instrument assembly.
Figure 9:
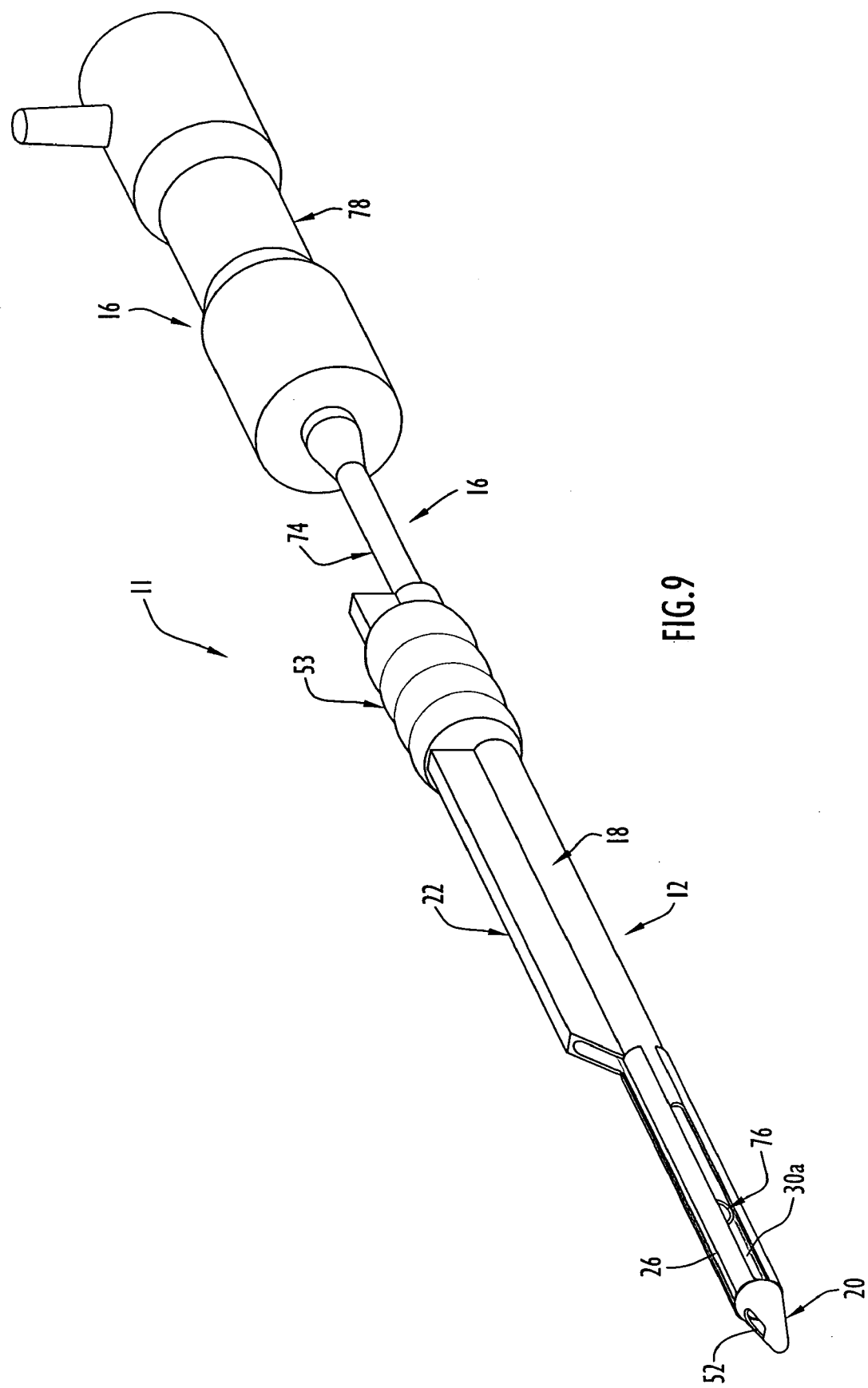
FIG. 9 is a perspective view depicting the cannula and the endoscope in an assembled condition, without the cutting member, to form a visualization instrument assembly.
Figure 10:
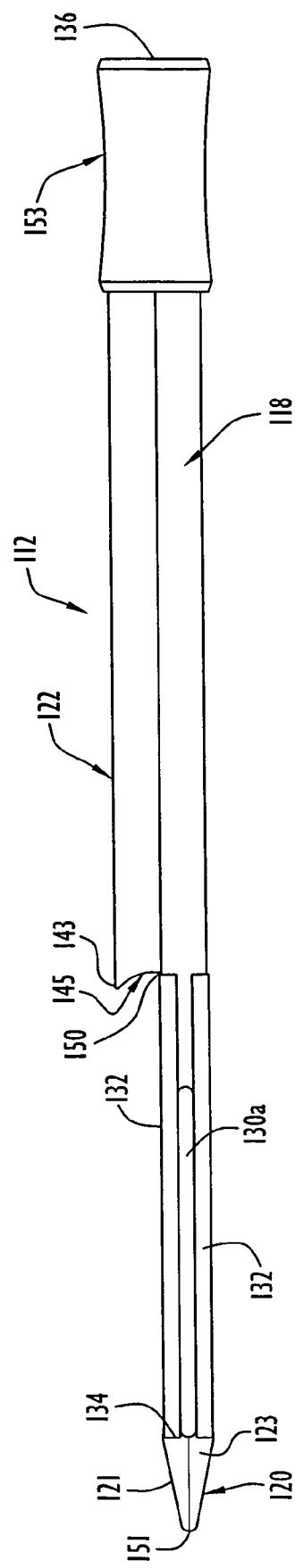
FIG. 10 is a side view of an alternative cannula for the instrument assemblies of the present invention.
Figure 11:
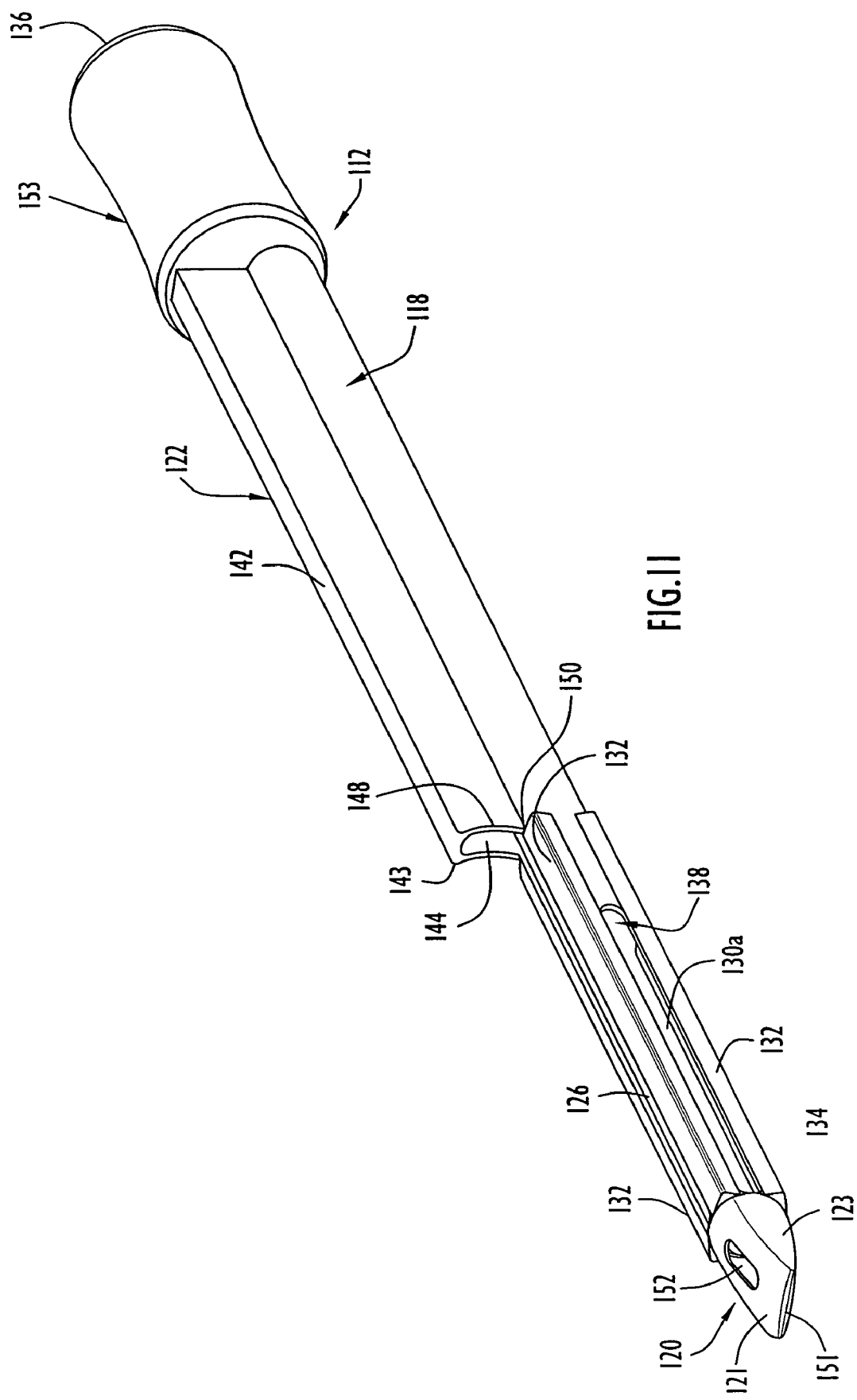
FIG. 11 is a perspective view of the alternative cannula.
Figure 12:
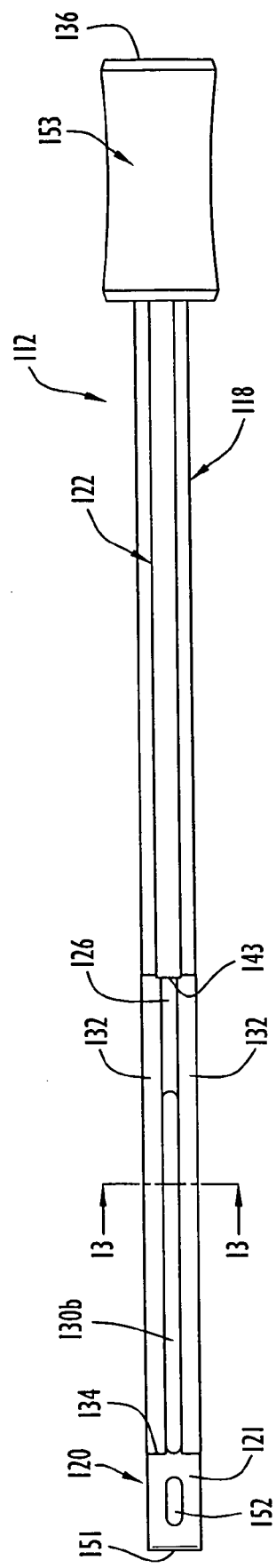
FIG. 12 is a top view of the alternative cannula.

FIGS. 1 and 2 illustrate the components of a cutting and visualization instrument assembly 10 in an exploded or unassembled condition. The cutting and visualization instrument assembly 10 comprises an outer member, cannula or sheath 12, a cutting member 14 for being received within the cannula 12, and an endoscope or remote visualization device 16 for being received within the cutting member 14. FIG. 8 depicts the cutting and visualization instrument assembly 10 in an assembled condition with the cutting member 14 slidably received within the cannula 12 and the endoscope 16 slidably received within the cutting member 14 for use in a minimally invasive or endoscopic carpal tunnel release procedure. FIG. 9 illustrates the cannula 12 with the endoscope 16 slidably received therein in an assembled condition without the cutting member 14, thereby forming a visualization instrument assembly 11 for use in a minimally invasive carpal tunnel release procedure.

As shown in FIGS. 1-6, cannula 12 comprises an elongate tubular member 18 having a central longitudinal axis x, a hollow distal tip 20 joined to one end of the tubular member 18, a blade housing 22 extending from an exterior surface of the tubular member 18 along a proximal length portion 24 of the tubular member 18, a longitudinal slot or fenestration 26 in an exterior or outer wall of the tubular member 18 extending through blade housing 22 and along a distal length portion 28 of the tubular member 18, a plurality of longitudinal slots or fenestrations 30a, 30b and 30c in the exterior wall of tubular member 18 extending along the distal length portion 28, and a plurality of exterior protuberances 32 on the tubular member 18 along the distal length portion 28. The distal tip 20 is joined to the one end of the tubular member 18 at a peripheral or circumferential junction 34 disposed in a plane perpendicular to the central longitudinal axis x, which is also the central longitudinal axis of the cannula 12. The distal tip 20 defines a closed distal end of cannula 12, and the end of tubular member 18 opposite the distal tip 20 defines or is in communication with an open proximal end 36 of cannula 12. The lumen of tubular member 18 circumscribed by the exterior wall defines a longitudinal interior passage 38 in the cannula 12 coaxial with the central longitudinal axis x and in communication with the open proximal end 36 and with the interior of the hollow distal tip 20. The proximal length portion 24 of tubular member 18 defines a proximal length portion of cannula 12. The distal length portion 28 of tubular member 18 and the distal tip 20 of cannula 12 together define a distal length portion of the cannula 12.

The longitudinal slot 26 is formed through the exterior wall of the tubular member 18 along the top of the cannula 12 and extends distally from the open proximal end 36 in parallel with the central longitudinal axis x to terminate at, adjacent or near the junction 34. The slot 26 thusly extends along the proximal and distal length portions 24 and 28 of the tubular member 18 and provides communication with the passage 38 through the wall of the tubular member 18. As explained further below, the slot 26 also provides communication between the passage 38 and an interior channel of blade housing 22. The slot 26 has a width extending between parallel side edges of the slot and has a length extending the entire or substantially the entire length of tubular member 18. A rearward or proximal end of slot 26 is open at the open proximal end 36 of the cannula 12. A forward or distal end of slot 26 disposed at, adjacent or near the junction 34 is closed by a forward or distal edge of the slot 26. The forward edge of slot 26 interconnects the side edges of the slot and may be arcuate or curved between the side edges of the slot.

Figure 6:
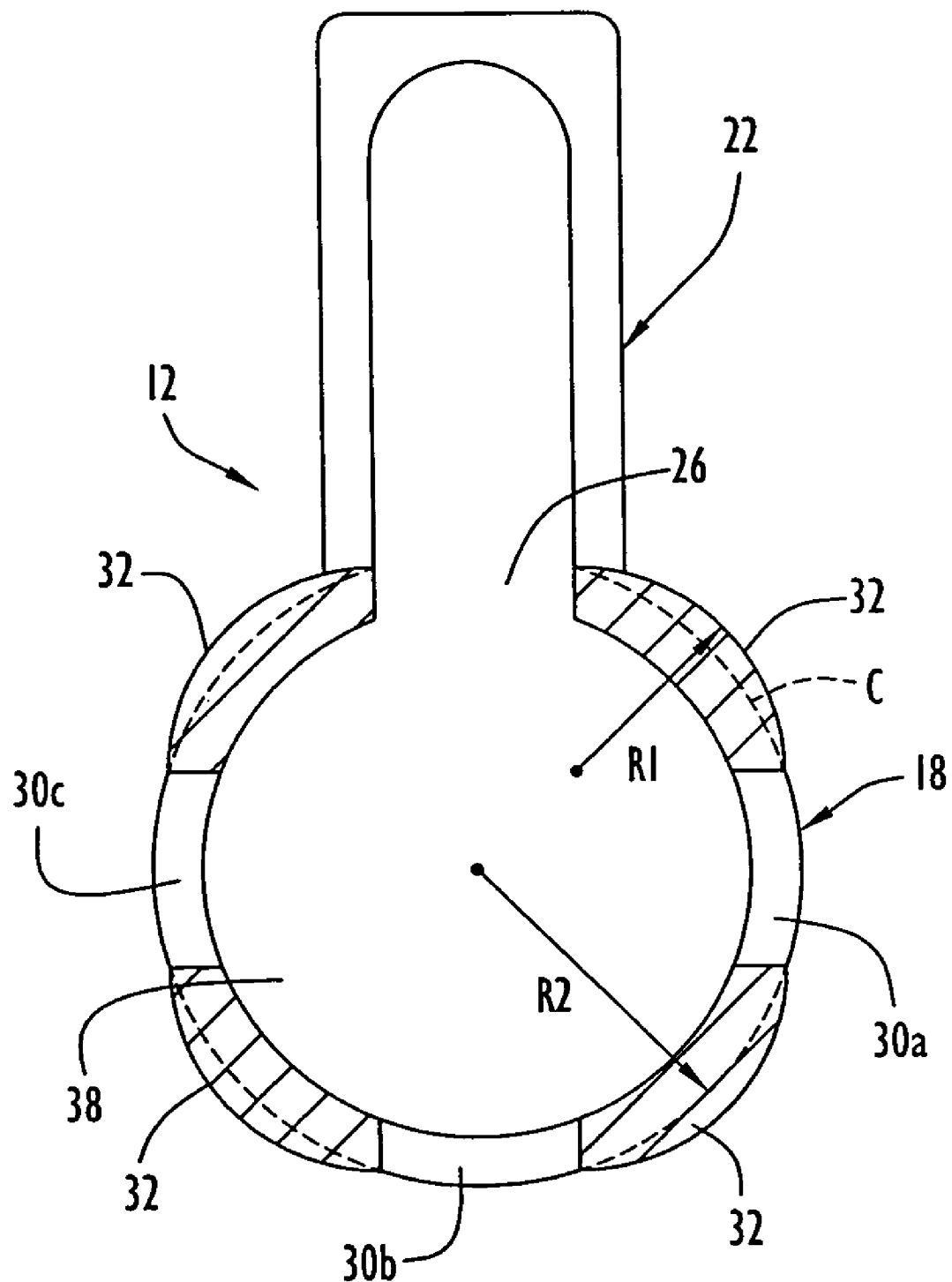
FIG. 6 is a sectional view of the cannula taken along line 6-6 of FIG. 4.

Blade housing 22 extends outwardly from the exterior surface of tubular member 18 in a direction radial to central longitudinal axis x along the top of the cannula 12. The blade housing 22 comprises a pair of spaced side walls 40 extending outwardly from the exterior surface of tubular member 18 to a top wall or roof 42 of the blade housing. The top wall 42 interconnects the side walls 40 to enclose an interior channel 44 that extends entirely through blade housing 22 and is in communication with the interior passage 38 via slot 26. The side walls 40 have lower ends joined to the tubular member 18 and have upper ends respectively joined to opposite sides of top wall 42. As illustrated in FIG. 6, the exterior corners where the upper ends of the side walls 40 are respectively joined to the sides of top wall 42 may be beveled or rounded to eliminate sharp corners. The side walls 40 extend along or follow the respective side edges of longitudinal slot 26 in the distal direction from an open rearward or proximal end 46 of the blade housing 22 to a forward or distal end surface 48 of the blade housing. An opening along the forward end surface 48 leads into the channel 44, and the forward end surface 48 defines an open forward or distal end of the blade housing 22. The forward end surface 48 slopes or extends angularly downwardly from the top wall 42 in the distal direction in a plane disposed at an acute angle to the central longitudinal axis x to meet the tubular member 18 at a union 50, such that the forward end of the blade housing 22 has a beveled configuration. The distal length portion 28 of the tubular member 18 extends from the union 50 to the junction 34. The channel 44 has a width between the side walls 40 and has a height between the top wall 42 and the slot 26 in a direction radial to central longitudinal axis x. Blade housing 22 is illustrated with the side walls 40 being planar and parallel to each other, with the channel 44 being of uniform width along the length of the blade housing, with the top wall 42 having an arcuate interior surface between planar interior surfaces of the side walls 40, and with the top wall 42 having a planar exterior surface extending perpendicularly between planar exterior surfaces of the side walls 40. However, it should be appreciated that various other configurations are possible for the blade housing 22 while still fulfilling its intended purpose and function as described further below.

The slots 30a, 30b and 30c are, like slot 26, formed through the exterior wall of the tubular member 18 in parallel with the central longitudinal axis x and provide communication through the wall of the tubular member 18 with the interior passage 38. The slots 30a, 30b and 30c, however, are confined to the distal length portion 28 of the tubular member 18. Each slot 30a, 30b and 30c has parallel side edges interconnected by a rearward or proximal edge at a closed proximal end of the slot and by a forward or distal edge at a closed distal end of the slot. The rearward edges of slots 30a, 30b and 30c are spaced distally or forwardly from the union 50, and the forward edges of slots 30a, 30b and 30c are disposed at, adjacent or near the junction 34. Each slot 30a, 30b and 30c has a width between its parallel side edges and a length between its forward and rearward edges. The width of each slot 30a, 30b and 30c may be the same or substantially the same as the width of slot 26, and the forward and rearward edges of the slots 30a, 30b and 30c may be arcuate or curved.

The slots 26, 30a, 30b and 30c are located in the tubular member 18 at 90° spaced radial locations about the central longitudinal axis x. As best seen in FIG. 6, slot 26 is located at a 0° or twelve o'clock radial location at the top of the cannula 12; slot 30a is located at a 90° or three o'clock radial location at a side of the cannula 12; slot 30b is located at a 180° or six o'clock radial location at the bottom of the cannula 12; and slot 30c is located at a 270° or nine o'clock radial location at a side of the cannula 12 opposite the slot 30a. The slot 26 may be considered a volar slot relative to the wrist being operated on in the minimally invasive carpal tunnel release procedure described herein, and the slot 30b may be considered a dorsal slot relative to the wrist being operated on in the minimally invasive carpal tunnel release procedure. The slots 30b and 30c may be considered radial or ulnar slots relative to the wrist being operated on in the minimally invasive carpal tunnel release procedure depending on whether the wrist being operated on is the wrist of the right or left hand of the patient.

Four exterior protuberances 32 are provided on tubular member 18 at spaced radial locations about axis x, each protuberance 32 being located between a pair of adjacent slots 26, 30a, 30b and 30c. Each protuberance 32 is at a radial location mid-way between the radial locations for the corresponding pair of adjacent slots. As best seen in FIG. 6, a first protuberance 32 is located on the tubular member 18 at a 45° radial location; a second protuberance 32 is located at a 135° radial location; a third protuberance 32 is located at a 225° radial location; and a fourth protuberance is located at a 315° radial location. Each protuberance 32 has a cross-sectional configuration forming a convex or rounded bulge along the exterior surface of the tubular member 18 extending beyond the outer circumference C of the exterior wall of the tubular member 18. The convexly curving outer or exterior surface of each protuberance 32 extends between adjacent side edges of the pair of adjacent slots between which the protuberance is located. Each protuberance 32 has a radius of curvature R1 less than the radius of curvature R2 of the outer circumference C, such that the protuberances 32 are of greater curvature than the outer circumference of the tubular member 18. The protuberances 32, which may be formed by thickened portions of the exterior wall of the tubular member 18, have rearward or proximal ends at, adjacent or near the union 50 and have forward or distal ends at, adjacent or near the junction 34. The protuberances 32 extend longitudinally along the distal length portion 28 of the tubular member 18 in parallel with the central longitudinal axis x. The protuberances 32 are advantageous for providing additional stiffness and strength to the cannula 12, for guiding the cannula 12 along the subligamentous plane between the transverse carpal ligament and flexor tendon synovial sheath, for stabilizing the cannula 12 in position in the subligamentous plane, for retracting or displacing adjacent anatomical tissue and/or structures via clockwise and/or counterclockwise rocking movement of the cannula and for keeping important anatomical structures clear of the cutting zone of the cutting blade.

The distal tip 20 has an exterior configuration that tapers or narrows in height and width from junction 34 to a narrow distal terminus 51. The exterior configuration of the distal tip 20 is defined by a conical configuration having a circular base joined to the tubular member 18 at junction 34 and tapering or narrowing to a rounded or convexly curved apex or point forming distal terminus 51 aligned with the central longitudinal axis x. The distal tip 20 thusly includes a semi-spherical lower wall or surface segment 23 extending angularly upwardly in the distal direction from tubular member 18 to distal terminus 51, and a semi-spherical upper wall or surface segment 21 extending angularly downwardly in the distal direction from tubular member 18 to distal terminus 51 at the same but oppositely directed slope or angle as the lower wall segment. The interior of distal tip 20 is in communication with the interior passage 38 of the tubular member 18. A window 52 is formed through the wall of distal tip 20 at a location in line with the longitudinal slot 26 along the top or volar aspect of the cannula 12. The window 52 may have an oblong or oval peripheral configuration with its length or major dimension extending lengthwise along the distal tip 20. The window 52, the slot 26 and the interior channel 44 may be bisected by a common vertical plane radial to the central longitudinal axis x at the 0° or twelve o'clock position. The window 52 provides communication with the interior of distal tip 20 and, due to the taper of distal tip 20, the window 52 faces distally or forwardly at an acute angle to the central longitudinal axis x. The window 52 is located distally beyond the cutting zone of a cutting blade of the cutting member 14 that moves within and along slot 26, and the window 52 thusly provides viewing in a forward volar direction by the image receiving end of the endoscope 16 when disposed within the cannula as described further below.

At least the distal length portion of cannula 12 is made of a medically acceptable clear or transparent material including plastics such as polycarbonate. Preferably, the entire cannula is formed integrally unitarily or monolithically of transparent material, and it is preferred that the cannula be disposable following a single patient use. The cannula may include a handgrip 53 provided on the proximal length portion 24 of tubular member 18 to facilitate manual grasping. The handgrip 53 is depicted as a generally barrel-shaped member having the tubular member 18 and blade housing 22 passing entirely therethrough and having external circumferential indentations or grooves to promote a sound grip. It should be appreciated, however, that the handgrip 53 can have various configurations and can be mounted in various ways at various locations on the tubular member 18. The tubular member 18 and/or the blade housing 22 can terminate within the handgrip 53 and not extend entirely therethrough. The handgrip 53 can be made of the same material as the tubular member 18 or of a different material, and the handgrip need not be transparent. The handgrip 53 can be formed integrally unitarily or monolithically with the tubular member 18 or as a separate component assembled on the tubular member 18.

The proximal end 36 of the tubular member 18 and/or the handgrip 53 can be provided with or formed as an adapter permanently attached to or removable from the cannula 12 to support and center an instrument in the passage 38 when the outer diameter or cross-sectional dimension of the instrument is too small to enable the instrument to be supported and centered by virtue of a close fit with the passage 38. Such an adapter can be designed in various ways and may include a passage therethrough of fixed or variable cross-sectional size coaxial with axis x to receive an instrument therethrough with a close fit so that the instrument is centered in the passage 38 of the cannula 12 even where the outer diameter or cross-sectional dimension of the instrument is appreciably smaller than the inner diameter of tubular member 18.

Figure 7:
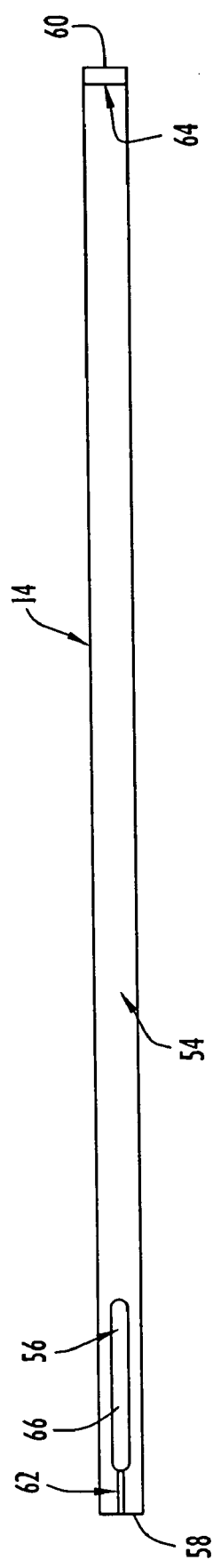
FIG. 7 is a top view of a cutting member of the cutting and visualization instrument assembly.

As depicted in FIGS. 1, 2 and 7, the cutting member 14 comprises an elongate cylindrical tube 54 having an internal lumen 56 extending entirely therethrough circumscribed by an exterior or outer wall of the tube, an open distal end 58 and an open proximal end 60 communicating with the lumen 56, a cutting blade 62 on a distal length segment of the tube 54, a handle 64 on a proximal length segment of the tube 54, and a slot or fenestration 66 in the outer wall along the distal length segment of the tube 54. The tube 54 preferably has an outer diameter to slidably fit concentrically or coaxially within the passage 38 of cannula 12 with a close fit. The open distal end 58 of the tube 54 is defined by a circumferential distal edge of the tube disposed in a plane perpendicular to a central longitudinal axis X of the tube. The open proximal end 60 of the tube 54 is configured with handle 64, which is depicted as a flange extending outwardly from the tube 54 at an angle to its central longitudinal axis X. A proximal or rearward face of the handle 64 is formed with a concave depression to accommodate the thumb or other fingers of the surgeon's hand placed against the handle 64 in order to manually slide or push the cutting member 14 longitudinally distally within the passage 38 of cannula 12. The handle 64 can also be grasped or engaged with the fingers and pulled in order to slide or pull the cutting member 14 longitudinally proximally within the passage 38 of cannula 12. The handle 64 is depicted extending outwardly from the tube 54 in an upward direction perpendicular to the central longitudinal axis X of the tube. It should be appreciated, however, that the handle 64 can be designed in various ways, can be formed with or mounted in various ways on the tube 54, and can be disposed at various locations on the tube 54 for use in effecting longitudinal sliding movement of the cutting member 14 within the passage 38 of cannula 12. The tube 54 is preferably of sufficient length for the blade 62 to reach the forward end of slot 26 when the cutting member 14 is distally advanced a maximum insertion distance in the cannula 12 with the handle 64 disposed proximally of the proximal end 36 of the cannula 12. When the cutting member 14 is disposed in the cannula 12 the maximum insertion distance, the handle 64 may be in abutment with the cannula 12. In the case of instrument assembly 10, the handle 64 comes into abutment with the proximal end 36 of tubular member 18 when the cutting member 14 is received in the cannula the maximum insertion distance. Depending on the design of the instrument assembly 10, however, the handle 64 can come into abutment with the proximal end 36 of tubular member 18, with the rearward end 46 of blade housing 22, with the handgrip 53, and/or with an adapter of the cannula 12.

The blade 62 is a thin, flat or planar blade of hook-like peripheral configuration extending outwardly from the tube 54, the blade 62 being disposed in a plane radial to the central longitudinal axis X of the tube. The blade 62 has arcuate forward and rearward edges 67 and 68 that curve outwardly from the outer or exterior surface of the tube 54 in the distal direction. The forward edge 67 is joined to the exterior surface of the tube 54 at, adjacent or near the distal end 58 of the tube, and the rearward edge 68 is joined to the exterior surface of the tube 54 proximally of the forward edge 67. The forward and rearward edges 67 and 68 each curve outwardly from the exterior surface of the tube 54 with a concave curvature toward the distal direction to meet one another at a blade tip 70, but with the forward edge 67 having a curvature greater than the curvature of the rearward edge 68. Accordingly, the more sharply curved forward edge 67 has a radius of curvature smaller than a radius of curvature of the more gently curved rearward edge 68, and the curvature of forward edge 67 resembles a reverse C-shape. The blade tip 70 does not extend distally beyond the circumferential distal edge of distal end 58 and is disposed at, adjacent or near the plane containing the circumferential distal edge of the tube 54. Also, an upper part of the rearward edge 68 curves over an upper part of the forward edge 67, and the forward edge 67 defines a cavity 72 between the blade tip 70 and the exterior surface of the tube 54 for accommodating the entire thickness of the transverse carpal ligament. The forward edge 67 is the leading edge of the blade 62 when the cutting member 14 is moved distally in cannula 12, and the forward edge 67 is provided with or formed as a sharp cutting edge between the blade tip 70 and the outer surface of the tube 54 to cut through the entire thickness of the ligament received in the cavity 72. However, the blade tip 70 itself is blunt to avoid trauma to nearby anatomical tissue.

The blade 62 is made of a medically acceptable material, such as stainless steel, of sufficient strength to withstand the force of cutting the transverse carpal ligament. The blade 62 and tube 54 can be formed as separate components, but preferably the blade 62 and tube 54 are formed integrally unitarily or monolithically as a single component. It is preferred that the cutting member 14 be disposable for single patient use. The blade 62 has a height extending beyond the outer surface of tube 54 in the radial plane of the blade and has a width or thickness perpendicular to the blade height. The blade 62 has a maximum length between the forward and rearward edges 67 and 68 at the outer surface of tube 54, the length of the blade being parallel to axis X in the radial plane of the blade.

The width of blade 62 is selected so that the blade 62 is slidable longitudinally within and along the slot 26 and channel 44 with the blade confined between the side edges of the slot 26 with a close fit when the tube 54 is slidably received in the passage 38 of cannula 12. Confinement of the blade 62 between the side edges of the slot 26 constrains the cutting member 14 from rotating within the cannula 12 and ensures that the blade 62 is guided in a straight cutting path along slot 26. The height and width of the blade 62 are selected to fit within the blade housing 22 with a close fit so that the blade 62 is protected and not exposed when it is slidably disposed in channel 44. The cavity 72 defined by forward edge 67 has a height in the radial plane of the blade 62 to receive the entire thickness of the transverse carpal ligament between blade tip 70 and the outer surface of tube 54, and the sharp cutting edge extends a sufficient distance along forward edge 67 to cut through the entire thickness of the ligament.

The slot 66 is formed through the outer wall of tube 54 in parallel with central longitudinal axis X, the longitudinal axis of the slot 66 being contained in the radial plane of blade 62. The slot 66 extends longitudinally from a closed forward or distal end of slot 66 located at, adjacent or near the rearward edge 68 of blade 62 to a closed rearward or proximal end of the slot 66. The slot 66 has parallel side edges and has a width between its parallel side edges. The slot 66 has a length between its forward and rearward ends, and the forward and rearward edges of the slot 66 at its respective forward and rearward ends may be arcuate or curved. The width of slot 66 may be the same or substantially the same as the width of slot 26 of cannula 12, and the slot 66 may be shorter in length than the slots 30a, 30b and 30c of cannula 12. The length of slot 66 is aligned with the length of blade 62, the slot 66 being bisected by the radial plane of blade 62. Accordingly, the slot 66 is in alignment with the slot 26 when the cutting member 14 is slidably received in the cannula 12 with blade 62 disposed in slot 26 and distally advanced from blade housing 22.

The endoscope or remote visualization device 16 comprises an elongate shaft 74 having a distal or image obtaining end 76 and having a proximal end associated with a housing 78. The image obtaining end 76 may include a lens 79 or other suitable optical device for obtaining an image within the field of view of the lens, and the lens may be disposed at an acute angle to a central longitudinal axis L of the shaft 74. In the case of endoscope 16, the lens 79 is disposed at an angle of 30° to the central longitudinal axis L of the shaft 74. The housing 78, which can serve as a handpiece for the endoscope 16, may include a fitting 80 for connection with a light source and may include a coupling 81 for connection with a video cable to establish communication with a video monitor (not shown). The shaft 74 and housing 78 can contain the components of a suitable optical transmission system for transmitting the image obtained by the image obtaining end 76 for remote visualization on the video monitor. The endoscope 16 can be a conventional endoscope and, in particular, a conventional 30° endoscope designed for use in minimally invasive or endoscopic surgery.

Preferably, the shaft 74 has an outer diameter to be slidably and rotatably received concentrically or coaxially in the lumen 56 of cutting member 14 with a close fit. The shaft 74 is preferably of sufficient length for the image obtaining end 76 to extend distally beyond the distal end 58 of the cutting member 14 into the interior of distal tip 20 and into alignment or substantial alignment with window 50 when the cutting member is inserted its maximum insertion distance into cannula 12 with the housing 78 disposed proximally of the handle 64 of the cutting member 14. The shaft 74 is also slidably and rotatably receivable concentrically or coaxially within the interior passage 38 of cannula 12 without the cutting member 14 received therein. The shaft 74 can be introduced in the passage 38 of cannula 12 through a suitable adapter designed to support the endoscope so that the shaft 74 is centered concentrically or coaxially within the passage 38 without the cutting member 14.

In a representative but not limiting cutting and visualization instrument assembly 10, the cannula 12 has an overall length of or about 19.0 cm, the distal tip 20 has a length of or about 1 cm; the tubular member 18 has an outer or exterior diameter of or about 6.5 mm and an inner or interior diameter of or about 5.5 mm which is also the diameter of passage 38; the blade housing 22 has a height of or about 5.5 mm; the slots 26, 30a, 30b and 30c have a width of or about 2 mm which is also the width of channel 44; the slots 30a, 30b and 30c have a length of or about 4.5 cm; the distal ends of protuberances 32 are located 1.2 cm or about 1.2 cm proximally from the distal terminus 51; the protuberances 32 have a length of or about 6 cm and a radius of curvature of or about 0.5 mm; the tubular member 18 has a width including the protuberances 32 of or about 7.5 mm; the window 50 has a length of or about 6 mm and a width of or about 2 mm; the handgrip 53 has a length of or about 3.0 cm and a width of or about 1.5 cm; the cutting member 14 has an overall length of or about 17.0 cm; the tube 54 has an outer or exterior diameter of or about 5.0 mm and an inner or interior diameter of or about 4.5 mm which is also the diameter of the lumen 56; the blade 62 has a height of or about 4.0 mm and a maximum length of or about 5.0 mm; the cutting edge of the blade 62 has a width or thickness of or about 0.7 mm; the slot 66 has a length of or about 2 cm and a width of or about 2 mm; and the endoscope 16 is a 30° endoscope conventionally known as a 5 mm endoscope with a shaft 74 that is 4.0 mm in diameter.

The cannula 12 and cutting member 14 comprise an instrument which, when assembled with an endoscope, form a cutting and visualization assembly. The cutting and visualization instrument assembly 10 is assembled by slidably inserting the cutting member 14, distal end first, in the open proximal end 36 of cannula 12 and slidably inserting the endoscope 16, distal end first, in the open proximal end 60 of cutting member 14. The cutting member 14 is slidably inserted in the cannula 12 with the tube 54 concentrically or coaxially disposed in the passage 38 and the blade 62 extending through the slot 26 into the channel 44 of the blade housing 22. When the blade 62 is disposed along the proximal length portion 24 of the cannula 12, it is disposed within the channel 44 of the blade housing 22 and is thusly protected and not exposed. As the cutting member 14 is moved distally within and relative to the cannula 12 by manually sliding the cutting member 14 longitudinally distally within the cannula 12, the blade 62 is exposed from the blade housing 22 when it exits the open forward end of the blade housing and is disposed along the distal length portion of the cannula 12. Distal movement of blade 62 from the blade housing 22 toward the forward end of slot 26 also brings the slot 66 of the cutting member 14 into alignment with the slot 26. The blade 62 is slidable within and along the slot 26 and the channel 44 as the tube 54 slides within the passage 38, and rotation of the cutting member 14 relative to the cannula 12 is limited or controlled due to confinement of the blade 62 between the side edges of the slot 26 and/or between the side walls of blade housing 22. Distal or forward movement of the cutting member 14 within the cannula 12 can be limited or controlled by abutment of the blade 62 with the forward edge of slot 26, by abutment of the distal end of the tube 54 with an interior surface of the distal tip 20, and/or by abutment of the handle 64 with the cannula 12 in the maximum inserted position for the cutting member within the cannula.

The endoscope 16 is slidably inserted in the open proximal end 60 of tube 54 so that shaft 74 is slidably and rotatably received in lumen 56 concentrically or coaxially. The shaft 74 is slidable distally and proximally relative to and within the tube 54 and is also rotatable relative to and within the tube 54. When the cutting member 14 is in its maximum inserted position in cannula 12, the endoscope 16 can be advanced longitudinally distally within and relative to the tube 54 so that the image obtaining end 76 of the endoscope 16 extends distally beyond the open distal end 58 of tube 54 and into the interior of distal tip 20. Rotation of the endoscope 16 relative to and within the cutting member 14 allows the image obtaining end 76 to be positioned in alignment or substantial alignment with the window 52 to provide visualization in the forward volar direction through the window 52. In a carpal tunnel release procedure, endoscopic visualization through window 52 permits viewing of the operative site or area including the transverse carpal ligament, passage of the blade 62, the superficial palmar arterial arch, and the area distal of the transverse carpal ligament. The endoscope 16 can also provide visualization of the operative site or area through the transparent wall of the distal tip 20 in other rotational positions for the image obtaining end 76 within the distal tip 20. The endoscope 16 can also be positioned longitudinally and rotatably within the tube 54 so that the image obtaining end 76 is in alignment with the slot 66 to provide visualization of the operative site or area through the volar slot 66 and the volar slot 26 with which the slot 66 is aligned. In this manner, endoscopic visualization can be obtained just proximal to the blade 62 to view the cutting zone of the blade and cutting of the transverse carpal ligament by the blade. The cutting and visualization instrument assembly 10 can be disassembled by withdrawing the cutting member 14 and the endoscope 16 from the cannula 12 and by withdrawing the endoscope from the cutting member. As the cutting member 14 is withdrawn from the cannula 12, the blade 62 is protected within the blade housing 22 and is not exposed as it is moved along the proximal portion of the cannula.

The cannula 12 comprises an instrument which, when assembled with an endoscope, forms a visualization instrument assembly. The visualization instrument assembly 11 is assembled by slidably inserting the endoscope 16 within the cannula 12 without the cutting member 14. The endoscope 16 is slidably inserted, distal end first, in the open proximal end 36 of cannula 12 so that the shaft 74 is slidably and rotatably received in the passage 38, preferably concentrically or coaxially. The endoscope 16 can be moved longitudinally and rotatably relative to and within the cannula 12 to selectively position the image obtaining end 76 in alignment with any of the slots 26, 30a, 30b or 30c or with the window 52 to provide visualization of the operative site or area through the slots or window in the volar, dorsal, radial, ulnar and distal directions. The endoscope 16 can also provide visualization through the transparent wall of the cannula 12 in other longitudinal and/or rotational positions for the endoscope within the cannula.

An alternative cannula 112 for any of the cutting and visualization instrument assemblies or for any of the visualization instrument assemblies described herein is depicted in FIGS. 10-13. The cannula 112 is similar to the cannula 12 and can be assembled with the endoscope 16 to obtain a visualization instrument assembly and can be assembled with both the cutting member 14 and the endoscope 16 to obtain a cutting and visualization instrument assembly as described above for cannula 12. The cannula 112 differs from the cannula 12 primarily in the configuration of distal tip 120, the configuration of the distal or forward end of blade housing 122, and the configuration of protuberances 132. Also, the handgrip 153 of cannula 112 is configured differently than the handgrip 53 of cannula 12 and is arranged differently on the tubular member 118.

Cannula 112 comprises tubular member 118, distal tip 120, blade housing 122 having interior channel 144, longitudinal slots 126, 130a, 130b and 130c in tubular member 118, exterior protuberances 132 on tubular member 118, and interior passage 138 as described for cannula 12. The cannula 112 has a closed, tapered distal end defined by distal tip 120 and has an open proximal end 136. The distal tip 120 is joined to the tubular member 118 at a peripheral or circumferential junction 134, and the interior of distal tip 120 is in communication with the passage 138. The channel 144 through blade housing 122 is in communication with the passage 138 via slot 126 as described for cannula 12. The handgrip 153 has a generally hourglass configuration. The proximal ends of tubular member 118 and blade housing 122 do not extend proximally beyond the handgrip 153 but, rather, terminate within the handgrip 153. A proximal or rearward face of handgrip 153 has an opening therein defining the open proximal end 136 of cannula 112 that is in communication with the passage 138.

The distal tip 120 has an external configuration that tapers in height in the distal direction but not in width. The distal tip 120 comprises an upper wall or surface segment 121 and a lower wall or surface segment 123 extending angularly inwardly toward one another from the junction 134 to meet at a narrow transverse distal border forming distal terminus 151. The upper and lower wall segments 121 and 123 extend angularly inwardly toward one another at the same but opposite slope or angle with respect to the central longitudinal axis x of the cannula 112 such that the distal terminus 151 is aligned with a horizontal plane containing the central longitudinal axis x and bisecting the distal tip 120 horizontally. The upper wall segment 121 thusly extends downwardly from the junction 134 toward the bottom or dorsal direction at the same or substantially the same slope or angle that the lower wall segment 123 extends upwardly from the junction 134 toward the top or volar direction. The distal terminus 151 has a length extending transverse to the central longitudinal axis x between opposed sides of the distal tip 120, and the length of the distal terminus 151 is the same or substantially the same as the exterior diameter or width of the tubular member 118. The distal terminus 151 for distal tip 120 is straight or substantially straight along its length and is perpendicular or substantially perpendicular to the central longitudinal axis x. However, the distal terminus 151 could be convexly curved as described below for distal terminus 251. The distal terminus 151 is configured or finished as a narrow but rounded or blunt edge to avoid inflicting unnecessary trauma on anatomical tissue. The exterior surfaces of the upper and lower wall segments 121 and 123 may be rounded or may be flat. The upper and lower wall segments 121 and 123 may be partial spherical in cross-section. The distal tip 120 includes window 152 formed through upper wall segment 121 and providing communication with the interior of the distal tip 120.

In a representative but not limiting embodiment, the distal tip 120 has a length of or about 1 cm; the distal terminus 151 has a length of or about 6.5 mm which is also the exterior diameter or width of the tubular member 118; and the window 152 has a length of or about 7 mm and a width of or about 2 mm. The configuration of distal tip 120 is particularly advantageous for guiding the cannula 112 along the subligamentous plane between the transverse carpal ligament and the flexor tendon synovium while gently separating or retracting anatomical tissue in an endoscopic carpal tunnel release procedure as explained further below.

The distal or forward end of blade housing 122 is defined by a forward end surface 148 that curves upwardly from the tubular member 118 with a concave curvature in the distal direction to meet the top wall 142 of the blade housing 122 at a narrow ledge 143. The ledge 143 extends perpendicular to the central longitudinal axis x and protrudes distally or forwardly beyond the union 150 where the forward end surface 148 meets the tubular member 118. Accordingly, a recess 145 is defined between the ledge 143 and the slot 126. An opening located along the forward end surface 148 leads into the channel 144 as described above for blade housing 22. The distal or forward end configuration of blade housing 122 is advantageous for use in stabilizing or holding the transverse carpal ligament in place during cutting of the ligament by the cutting member in a carpal tunnel release procedure as explained in greater detail below. In particular, the ledge 143 can lock into or on the transverse carpal ligament with the proximal edge of the ligament accommodated in the recess 145 to position the ligament for cutting by the blade of the cutting member as it exits the channel 144 from the forward end of the blade housing 122.

Figure 13:
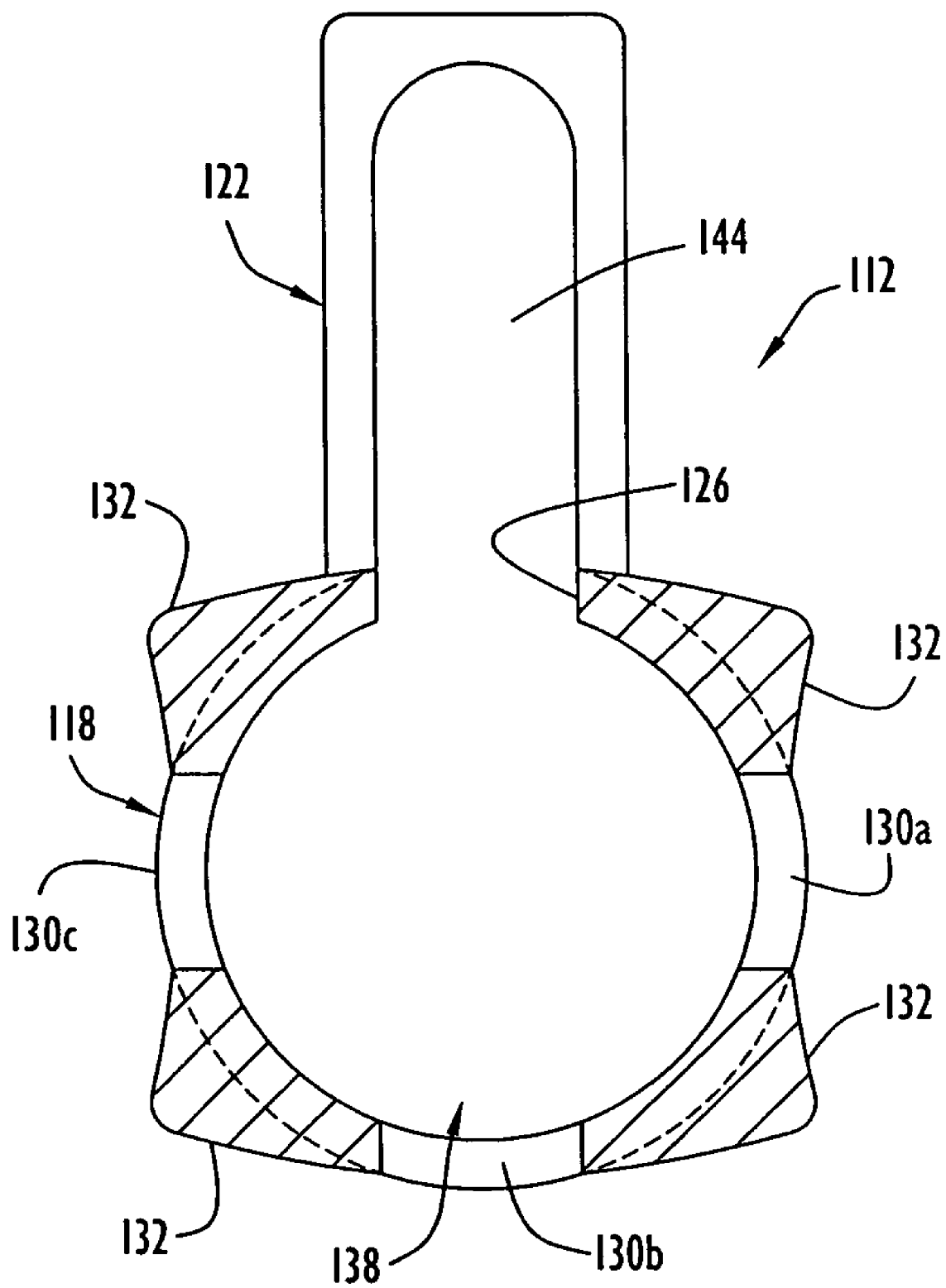
FIG. 13 is a sectional view of the alternative cannula taken along line 13-13 of FIG. 12.

The protuberances 132 are similar to the protuberances 32 but, as best seen in FIG. 13, have a more triangular configuration in cross-section than the protuberances 32 and are thusly less rounded and more pointed than the protuberances 32. The protuberances 132 are located on tubular member 118 at spaced radial locations about the central longitudinal axis x corresponding to the two o'clock, four o'clock, eight o'clock and ten o'clock positions about the central longitudinal axis x.

Figure 14:
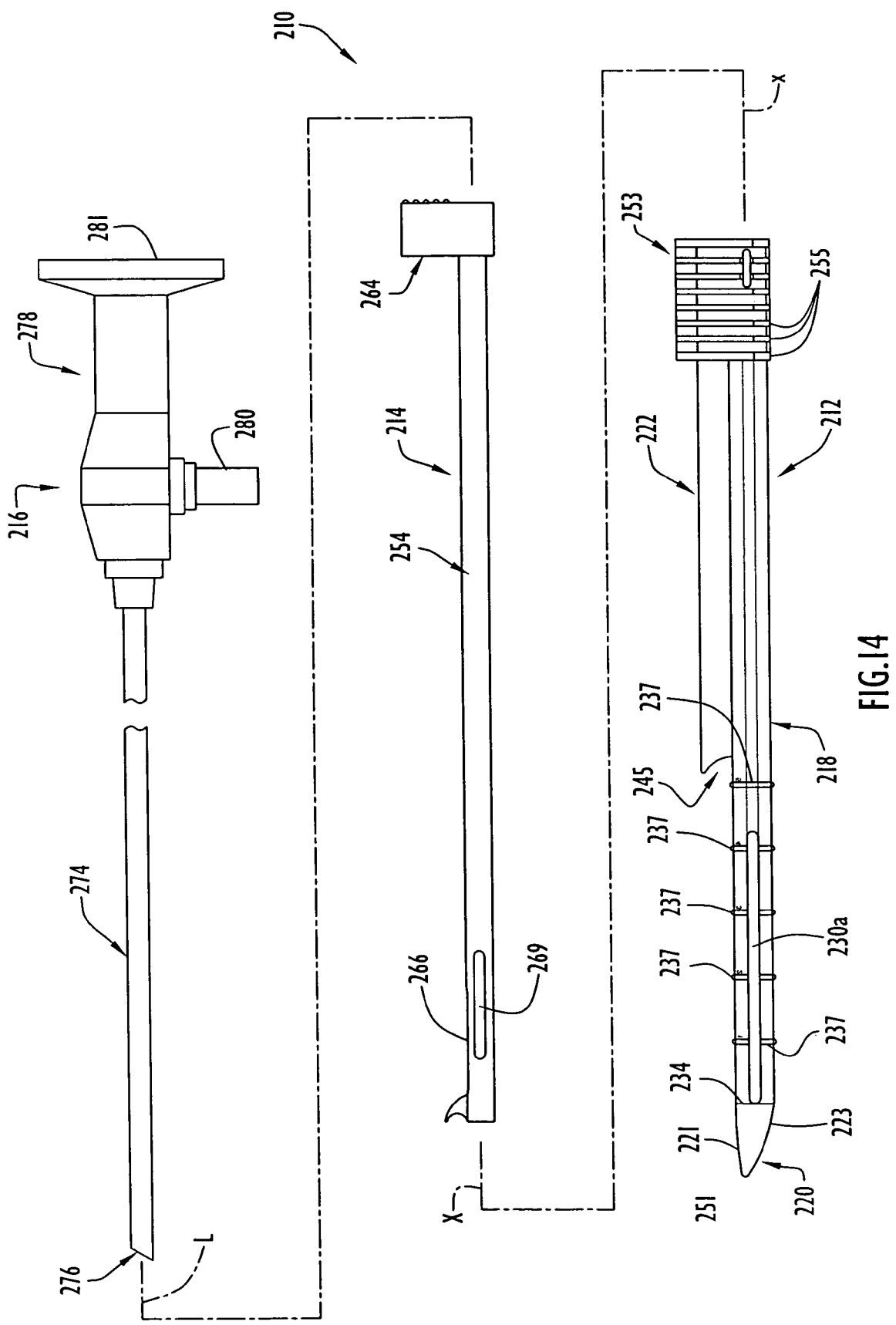
FIG. 14 is an exploded or unassembled side view of another and preferred embodiment of a cutting and visualization instrument assembly.
Figure 15:
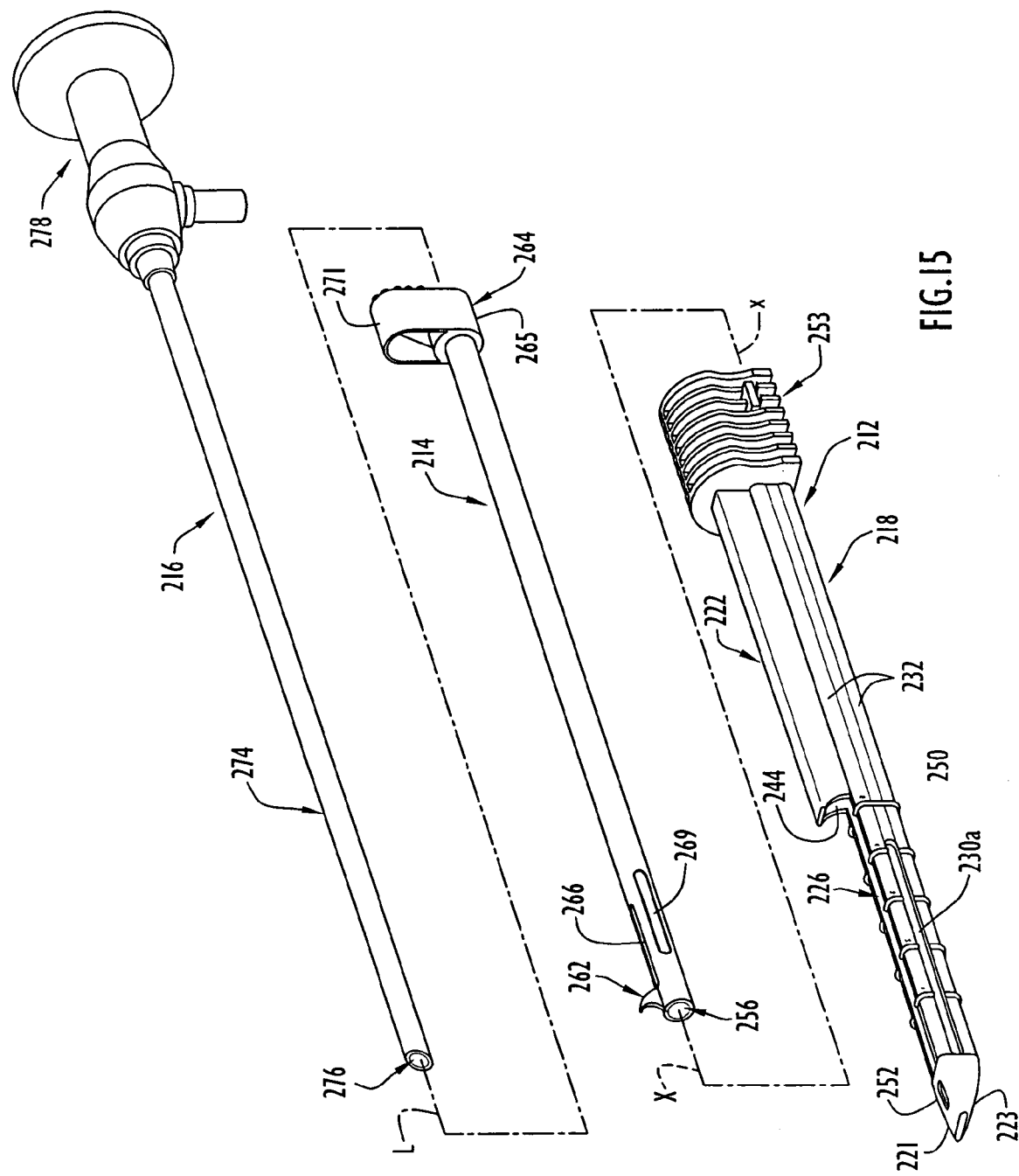
FIG. 15 is an exploded or unassembled perspective view of the preferred cutting and visualization instrument assembly.
Figure 18:
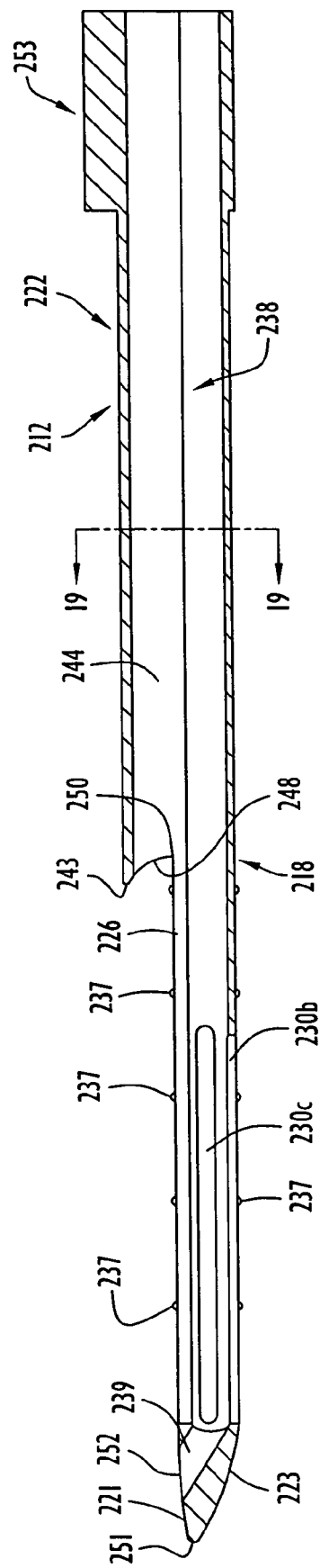
FIG. 18 is a longitudinal sectional view of the cannula of the preferred cutting and visualization instrument assembly.
Figure 22:
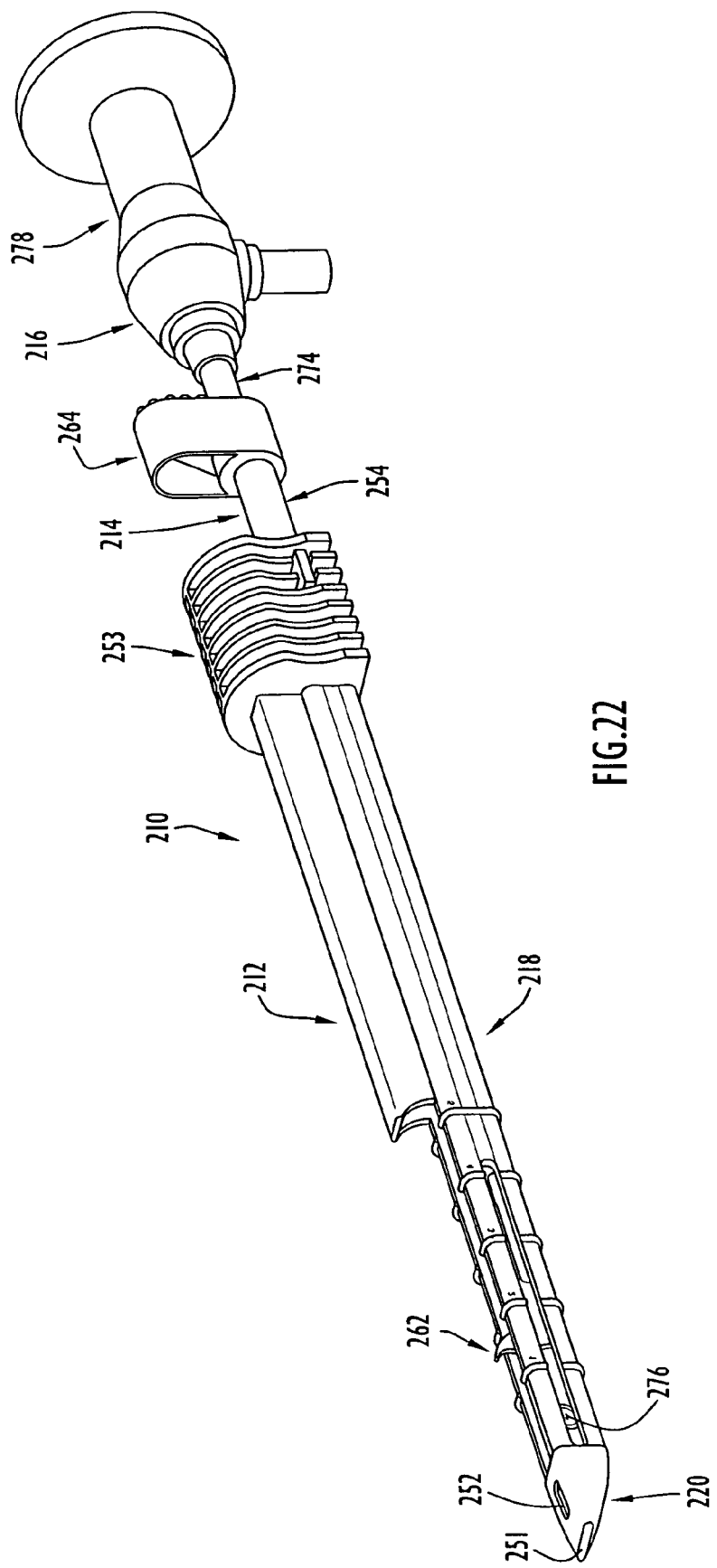
FIG. 22 is a perspective view of the cannula, the cutting member and an endoscope of the preferred cutting and visualization instrument assembly shown in an assembled condition for the preferred cutting and visualization instrument assembly.
Figure 23:
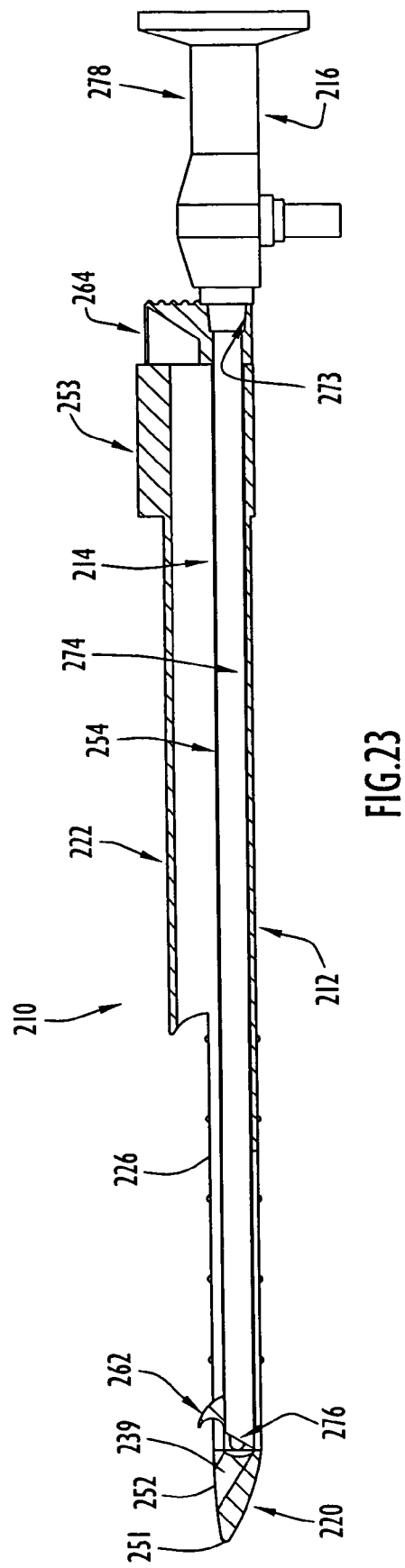
FIG. 23 is a longitudinal view, partly in section, of the preferred cutting and visualization instrument assembly in the assembled condition.
Figure 24:
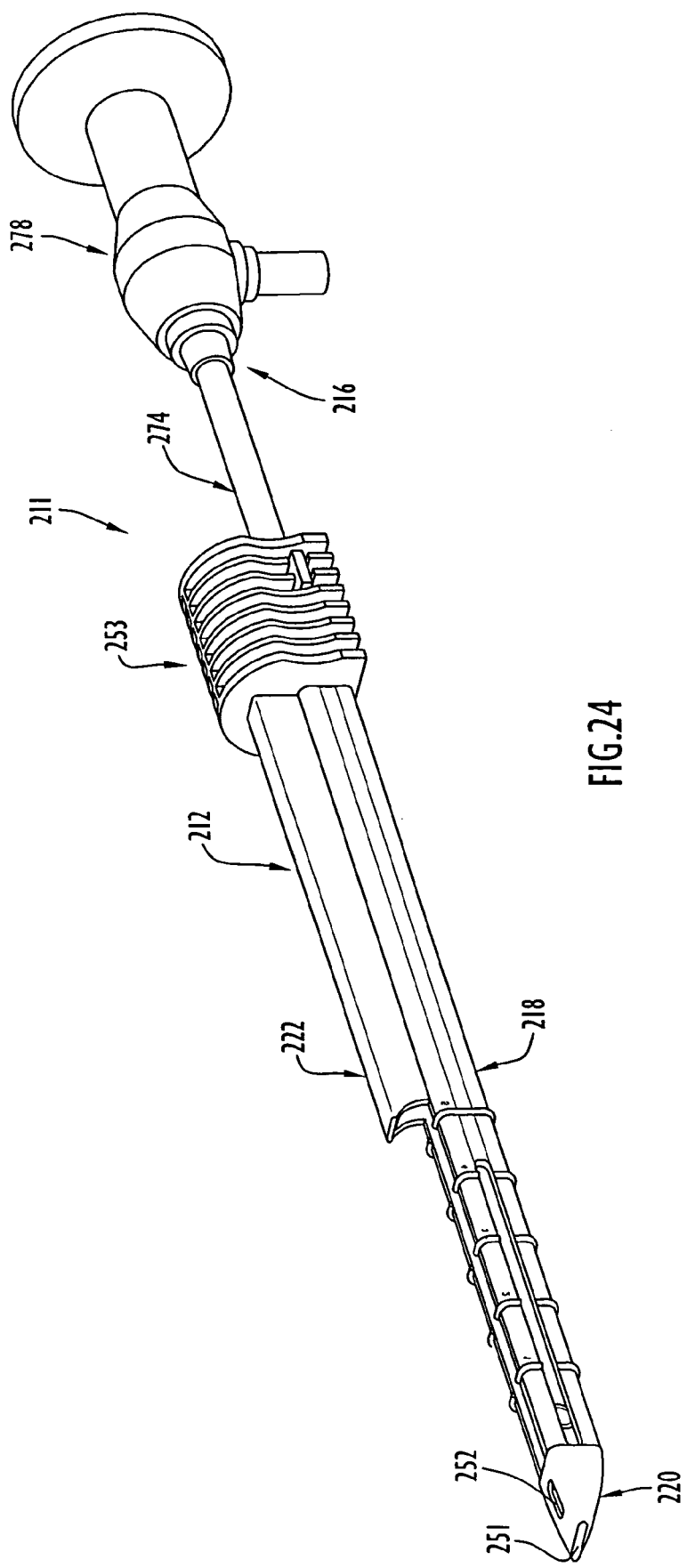
FIG. 24 is a perspective view depicting the cannula and the endoscope of FIG. 14 in an assembled condition, without the cutting member, to form an alternative and preferred visualization instrument assembly.

The components of another and preferred cutting and visualization instrument assembly 210 are depicted in an exploded or unassembled condition in FIGS. 14 and 15. The cutting and visualization instrument assembly 210 comprises cannula 212, cutting member 214 and endoscope 216. FIGS. 22 and 23 depict the cutting and visualization instruments assembly 210 in an assembled condition with the cutting member 214 slidably received within the cannula 212 and the endoscope 216 slidably and rotatably received within the cutting member 214. FIG. 24 illustrates the cannula 212 with the endoscope 216 slidably and rotatably received therein in an assembled condition, without the cutting member 214, thereby forming a visualization instrument assembly 211.

The cannula 212, as best seen in FIGS. 14-19, is similar to the cannula 112 but the distal terminus 251 for distal tip 220 of cannula 212 is convexly curved and is offset in the top or volar direction from the horizontal plane containing the central longitudinal axis x of cannula 212. The distal tip 220 has an external configuration that tapers in height in the distal direction, but the lower wall segment 223 of the distal tip 220 extends upwardly from junction 234 at a greater slope or angle toward the volar or top direction than the slope or angle that the upper wall segment 221 of the distal tip 220 extends downwardly from junction 234 toward the bottom or dorsal direction. The distal terminus 251 extends lengthwise between opposed sides of distal tip 220 in a direction transverse to the central longitudinal axis x of the cannula 212 but is not aligned with the horizontal plane containing axis x and is convexly curved along its length. Accordingly, the distal terminus 251 is offset in the volar direction from the horizontal plane of axis x and, due to its curvature, is not perpendicular to the central longitudinal axis x of the cannula 212. The distal terminus 251 could, however, be perpendicular or substantially perpendicular to the axis x as in the case of distal terminus 151. The width of distal tip 220 between its opposed sides is the same or substantially the same as the width of tubular member 218. The window 252 is formed in the upper wall segment 221 of distal tip 220 and is in communication with a chamber 239 extending within distal tip 220 at an upward angle from a forward end of the passage 238 to the window 252. Preferably, the chamber 239 extends upwardly at a 30° or substantially 30° angle to the central longitudinal axis x.

The blade housing 222 for cannula 212 is similar to blade housing 122 and includes ledge 243 and curved forward end surface 248 defining recess 245. The cannula 212 has volar slot 226, dorsal slot 230b, and radial/ulnar slots 230a and 230c similar to volar slots 26, 126, dorsal slots 30b, 130b and radial/ulnar slots 30a, 130a, 30c, 130c. The channel 244 of blade housing 222 is in communication with passage 238 via slot 226.

Figure 19:
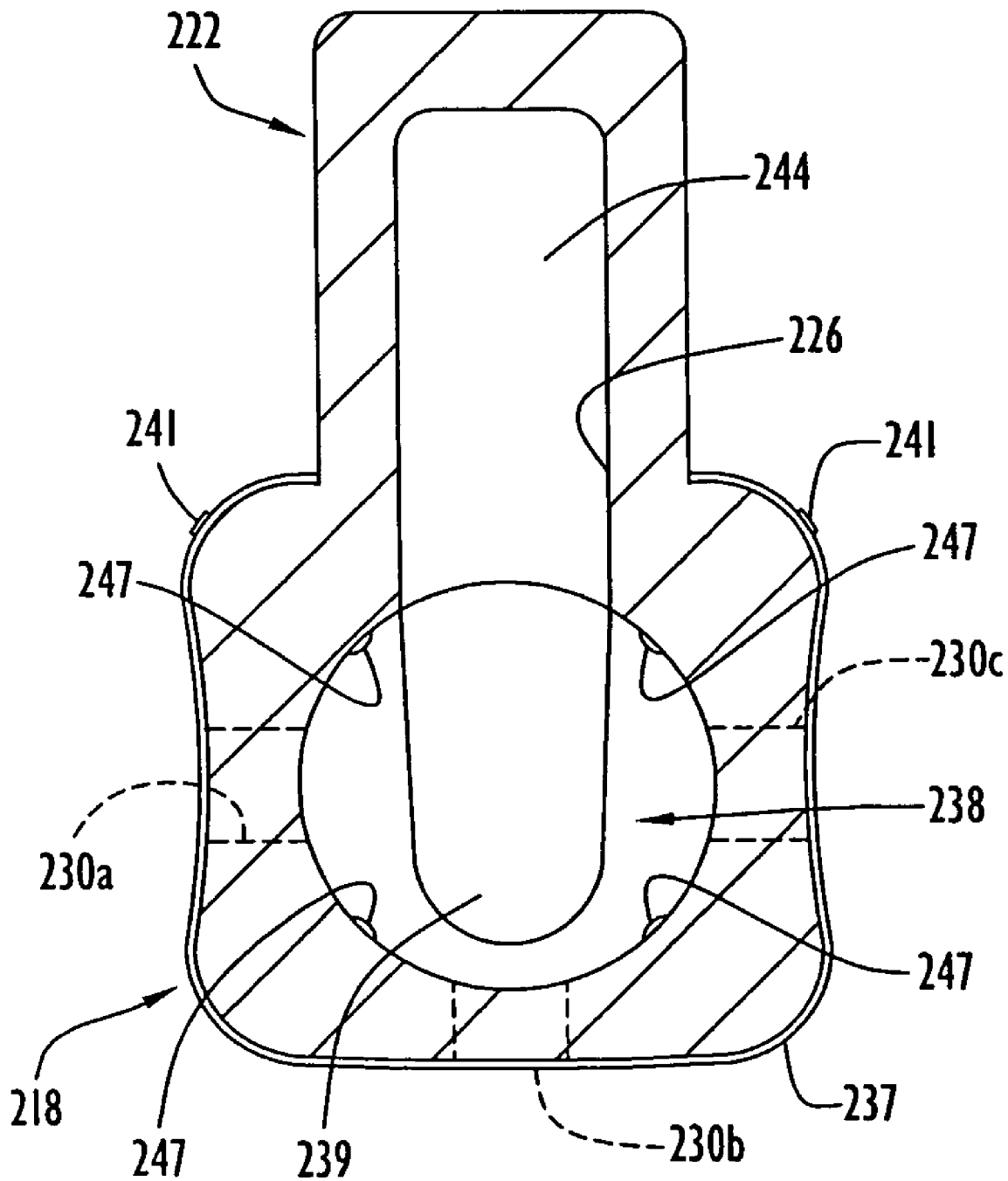
FIG. 19 is a sectional view of the cannula taken along line 19-19 of FIG. 18.
Figure 20:
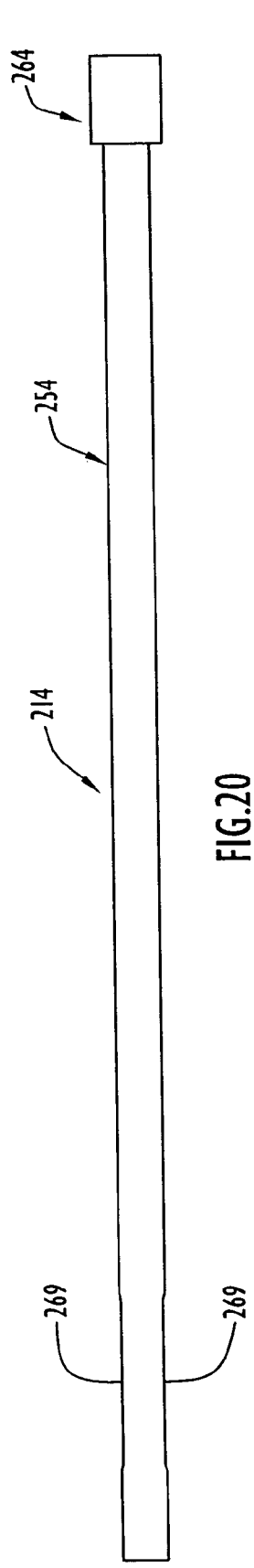
FIG. 20 is a bottom view of a cutting member of the preferred cutting and visualization instrument assembly.
Figure 21:
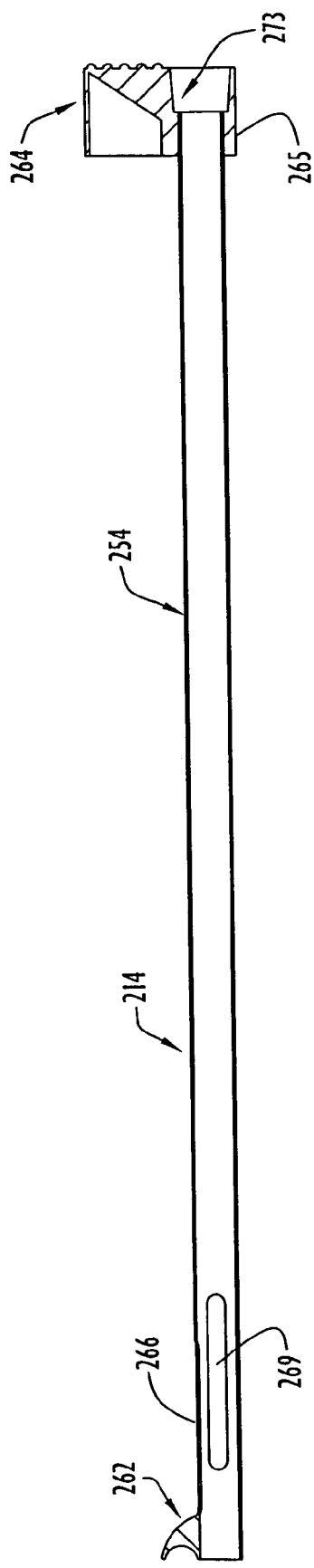
FIG. 21 is a longitudinal sectional view of the cutting member of the preferred cutting and visualization instrument assembly.

The tubular member 218 of cannula 212 differs from tubular member 18 in that the tubular member 218 has, as best shown in FIG. 19, a modified square peripheral configuration in external cross-section with four rounded corners defining protuberances 232. Each protuberance 232 is located between a respective pair of adjacent slots 226, 230a, 230b and 230c. Two of the protuberances 232 at the top of cannula 212 are upper or volar protuberances, and the two protuberances 232 at the bottom of the cannula 212 are lower or dorsal protuberances. Accordingly, there is a volar protuberance 232 and a corresponding dorsal protuberance 232 on each of radial and ulnar sides of the cannula 212. The tubular member 218 is of uniform or substantially uniform external cross-section along the distal and proximal length portions thereof such that the protuberances 232 extend longitudinally the entire or substantially the entire length of tubular member 218 in parallel with the central longitudinal axis x. The blade housing 222 and volar slot 226 are located between the two volar protuberances 232 and in opposition to the dorsal slot 230b which is located between the two dorsal protuberances 232. The configuration of tubular member 218 is particularly advantageous for guiding the cannula 212 along the subligamentous plane between the transverse carpal ligament and the flexor tendon synovial sheath, for stabilizing the cannula 212 in position in the subligamentous plane, for retracting or displacing adjacent anatomical tissue and/or structures via clockwise and/or counterclockwise rocking movement of the cannula, and for keeping important anatomical structures clear of the cutting zone of the cutting blade.

A plurality of raised reference formations 237 are provided along the periphery of the exterior surface of tubular member 218 at longitudinally spaced locations along the distal length portion of tubular member 218. The reference formations 237 are configured as rim formations equally spaced from one another in parallel planes perpendicular to the central longitudinal axis x, but can have other suitable configurations. The distalmost reference or rim formation 237 is spaced proximally from the junction 234 and/or from the forward end of slot 226 a distance equal or substantially equal to the spacing between each pair of adjacent reference or rim formations 237. The proximalmost reference or rim formation 237 is located at or adjacent the union 250 where the forward end surface of blade housing 222 meets the tubular member 218. The cannula 212 is depicted with five reference formations 237; however, a greater or lesser number of reference formations 237 could be provided on the cannula. The tubular member 218 is also provided with indicia 241 located thereon to distinguish or identify each reference formation 237. Each reference formation 237 is associated with at least one indicia 241 provided on the tubular member 218 adjacent or close to the corresponding reference formation and visible on the outside or exterior of the tubular member and by the endoscope 216 from within passage 238. In the case of cannula 212, each reference formation 237 is associated with a plurality of indicia 241 provided on the exterior surface of the tubular member 218. In particular, two indicia 241 are provided for each reference formation 237, there being an indicia 241 on each volar protuberance 232 adjacent the corresponding reference formation 237. The indicia 241 for each reference formation 237 identifies or distinguishes that reference formation from the remaining reference formations. Since the reference formations 237 are spaced along the distal length portion of tubular member 218 in equal increments between the forward end of blade housing 222 and the junction 234 and/or forward end of slot 226, the indicia 241 allow each reference formation 237 to be identified in relation to its location along the distal length portion of tubular member 218, its distance from the forward end of slot 226 and/or junction 234, and/or its distance from the forward end of blade housing 222. In the case of cannula 212, the indicia 241 are numerals. The first or distalmost reference formation 237 has the number "1" as its indicia; the second reference formation 237, which is the next proximal reference formation from the distalmost reference formation, has the number "2" as its indicia; the third reference formation 237, which is the next proximal reference formation from the second reference formation, has the number "3" as its indicia; the fourth reference formation 237, which is the next proximal rim formation from the third reference formation, has the number "4" as its indicia; and the fifth or proximalmost reference formation 237 has the number "5" as its indicia. When the blade 262 of cutting member 214 exits the forward end of blade housing 222 and is slid distally along the slot 226, the indicia 241 viewed by endoscope 216 from within the cutting member via the slots in the cutting member and the cannula provide an indication of the location of the cutting blade in reference to the reference formations 237 that is useful in gauging the extension distance of the blade 262 distally from the blade housing 222 to ensure complete division of the transverse carpal ligament while limiting overextension of the blade distally beyond the ligament as explained further below. The reference formations 237 may also serve as markers or reference points for appropriate insertion and positioning of the cannula 212 in the carpal tunnel, for gauging the location and size of anatomical features or structures in the carpal tunnel, and/or for appropriate insertion and positioning of the image obtaining end 276 of endoscope 216 in the passage 238 in accordance with anatomical features or structures desired to be viewed.

As seen in FIG. 19, the inner surface of the exterior wall of tubular member 218 that defines passage 238 has a plurality of raised, rounded ribs 247 extending longitudinally along the passage 238 in parallel with the central longitudinal axis x. The ribs 247, which may extend longitudinally the entire or substantially the entire length of passage 238, are arranged on the inner surface of tubular member 218 at spaced radial locations about the central longitudinal axis x. In particular, the ribs 247 are arranged in paired relation at diametrically or diagonally opposed locations. Four ribs 247 are provided on the inner surface of tubular member 218; however, a greater or lesser number of ribs could be provided. Two of the ribs 247 may be considered upper or volar ribs and are respectively located in symmetry on opposite sides of volar slot 226 adjacent or close to the side edges of the slot 226. The other two ribs 247 may be considered lower or dorsal ribs, each dorsal rib being located in symmetry on opposite sides of dorsal slot 230b and diametrically or diagonally opposite a volar rib. The ribs 247 project into the passage 238 and assist in supporting and centering the cutting member 214 within passage 238, provide a cushioning effect for the cutting member, and facilitate smooth longitudinal sliding movement of the cutting member within the passage.

The handgrip 253 for cannula 212 differs from the handgrips 53 and 153 and comprises a series of parallel flanges or fins 255 longitudinally spaced from one another along the tubular member 218, with the flanges extending outwardly beyond the outer surface of the tubular member 218 perpendicular to axis x. The handgrip 253 is disposed on the tubular member 218 such that the tubular member 218 and blade housing 222 do not extend proximally beyond the handgrip 253. Each flange 255 has the same or substantially the same peripheral configuration and size with a convexly curved top, a straight bottom and concavely indented sides to promote grasping. The flanges 255 may be interconnected by a longitudinal spine extending along the top of the handgrip 253. Advantages of handgrip 253 include ergodynamic comfort, sound grip, reduced weight and material requirements, and lower cost.

The cutting member 214 is best depicted in FIGS. 14, 15, 20 and 21. The cutting member 214 is similar to the cutting member 14 except that the tube 254 of cutting member 214 has slots 269 formed therein in addition to slot 266. Two additional slots 269 are formed in the tube 254, each slot 269 being disposed at a radial location spaced 90° from the radial location of slot 266 with respect to the central longitudinal axis X of the cutting member 214. The slot 266 is disposed at a 0° or twelve o'clock radial location on the cutting member 214 and, like the slot 66, may be considered an upper or volar slot. One slot 269 is disposed at a 90° or three o'clock radial location while the other slot 269 is disposed at a 270° or nine o'clock radial location on the cutting member 214. Like the slots 230a and 230c of cannula 212, the slots 269,269 may be considered radial or ulnar slots depending on whether the instrument assembly is used in a right or left wrist carpal tunnel release procedure. The distal or forward ends of slots 269 are disposed proximally of the distal or forward end of slot 266, and the slots 269 extend lengthwise beyond the proximal or rearward end of the slot 266. The slots 269 are therefore longitudinally offset from the slot 266. The slots 269 are parallel to slot 266 and to the central longitudinal axis X. The slots 269 provide communication through the wall of tube 254 with the lumen 256. When the cutting member 214 is received within the cannula 212 with blade 262 received in slot 226 of the cannula, the slots 266, 269 and 269 of cutting member 214 come into respective alignment with the slots 226, 230a and 230c of cannula 212. The endoscope 216, when received in the cutting member 214, may be rotated within the lumen 256 to selectively position the image obtaining end 276 of the endoscope 216 into alignment with any of the slots 266 and 269 to provide visualization of the operative site in the volar, radial and ulnar directions in an endoscopic carpal tunnel release procedure.

The handle 264 of cutting member 214 is somewhat different in configuration than handle 64. The handle 264 has an oblong peripheral or outer side wall defined by an adapter fitting 265 and an arch 271 extending upwardly from the adapter fitting 265. The fitting 265 contains an internal cavity 273 extending entirely therethrough coaxial with the central longitudinal axis X but in off-centered relation to the oblong peripheral wall. The proximal end of tube 254 is coaxially received in a distal portion of the cavity 273. The arch 271 is open along a distal or front edge thereof and is closed along a rearward or back edge thereof by a flange disposed perpendicular to the central longitudinal axis X. A rearward or proximal face of the flange is configured with ridges to provide a frictional or irregular surface conducive to retention of a finger or fingers of the hand in contact with the rearward face of the flange. A proximal portion of the cavity 273 is configured to mate with a forward part of the housing 278 of endoscope 216 and defines the open proximal or rearward end of the cutting member 214. When the shaft 274 of the endoscope 216 is inserted in the cutting member 214, mating engagement of the forward part of housing 278 with the proximal portion of cavity 273 causes the shaft 274 to be coaxially or concentrically centered within the tube 254 of the cutting member.

The endoscope 216 is similar to endoscope 16 except that its housing 278 differs in configuration from the housing 78. The forward part of housing 278 that mates with the proximal portion of the cavity 273 may be frustoconical in configuration and may extend from a vertical shoulder of the housing that comes into abutment with the flange of handle 264 when the forward part of the housing 278 is matingly engaged with the proximal portion of the cavity 273.

The cannula 212, cutting member 214 and endoscope 216 are assembled to form the cutting and visualization instrument assembly 210 in a manner similar to that described above for cutting and visualization instrument assembly 10. When the cutting member 214 is received within the cannula 212 its maximum insertion distance, the handle 264 of the cutting member is in abutment with the handgrip 253 of the cannula as best shown in FIG. 23. When the cutting member 214 is inserted in the cannula 212 the maximum insertion distance for the cutting member, the blade 262 is disposed at, adjacent or near the forward end of slot 226, and the open distal end of tube 254 is disposed at, adjacent or near the forward end of passage 238 that is in communication with the chamber 239 in distal tip 220. The endoscope 216 is inserted in the cutting member 214 a maximum insertion distance for the endoscope when the forward part of the housing 278 is in mating engagement with the proximal portion of the cavity 273 as illustrated in FIG. 23. When the endoscope 216 is at its maximum insertion distance within the cutting member 214, and the cutting member is also at its maximum insertion distance within the cannula 212, the image obtaining end 276 of the endoscope is in alignment or substantial alignment with the chamber 239 of distal tip 220 to provide visualization through the window 252. The configuration of the distal end of the passage 238 and the angle of chamber 239 allow the image obtaining end 276 to be aligned or substantially aligned with the chamber when the image obtaining end is extended distally only a small amount beyond the open distal end of the tube 254. The endoscope 216 is movable longitudinally and rotatably relative to and within the cutting member 214 to selectively position the image obtaining end 276 into alignment or substantial alignment with the pair of aligned slots 226, 266, the pair of aligned slots 230a, 269, or the pair of aligned slots 230c, 269 to provide visualization through the aligned slots. When the endoscope 216 is received within the cannula 212 without the cutting member 214 as shown in FIG. 24, the visualization instrument assembly 211 is obtained. The endoscope 216 is movable longitudinally and rotatably within the cannula 212 to selectively align the image obtaining end 276 with the window 252 or with any of the slots 226, 230a, 230b or 230c of the cannula to provide visualization. The image obtaining end 276 can also provide visualization through the transparent wall of the cannula 212.

It should be appreciated that the various components for the cutting and visualization instrument assemblies and for the visualization instrument assemblies are interchangeable in that any of the cannulas can be assembled with any of the cutting members and/or endoscopes to form various instrument assemblies.

Figure 25:
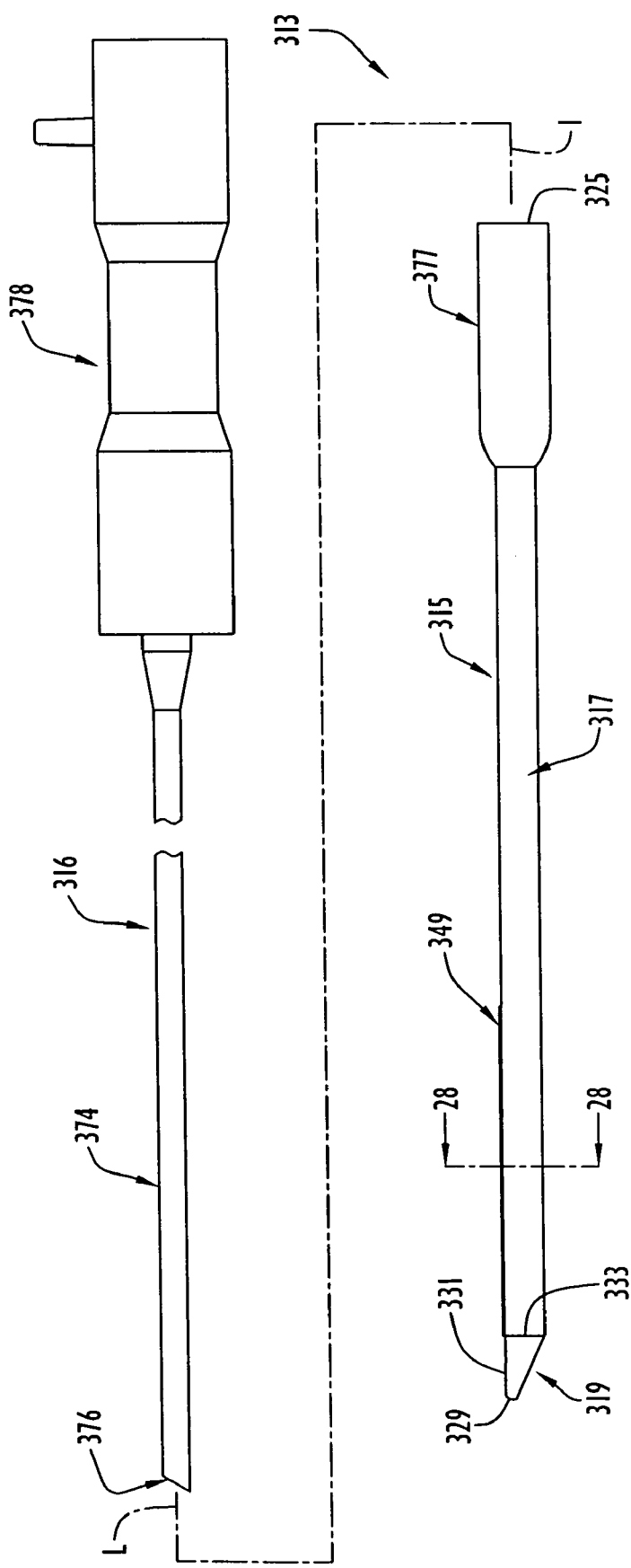
FIG. 25 is an exploded or unassembled side view of a dilating and visualization instrument assembly for use in endoscopic carpal tunnel release.
Figure 26:
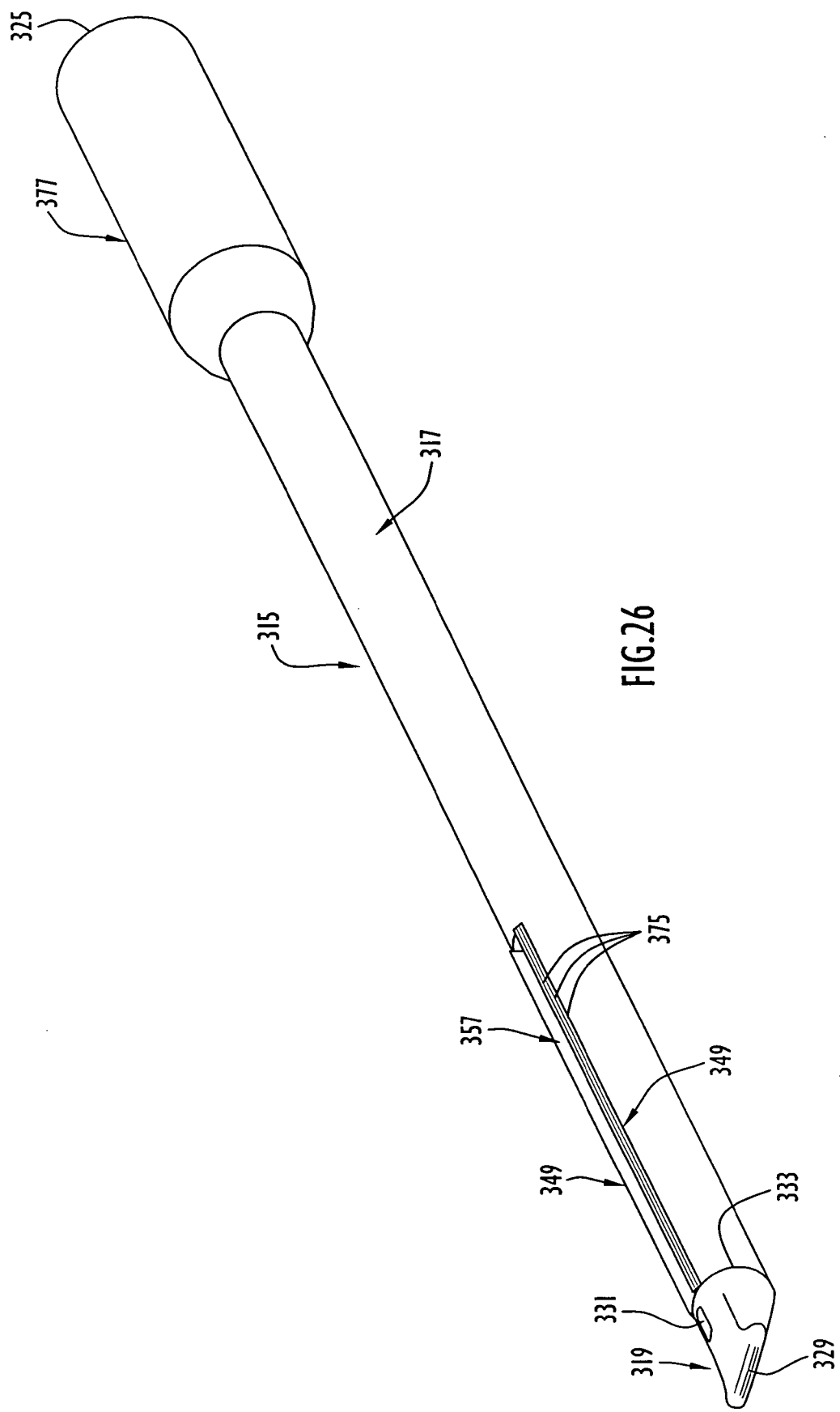
FIG. 26 is a perspective view of a dilating member of the dilating and visualization instrument assembly.
Figure 27:
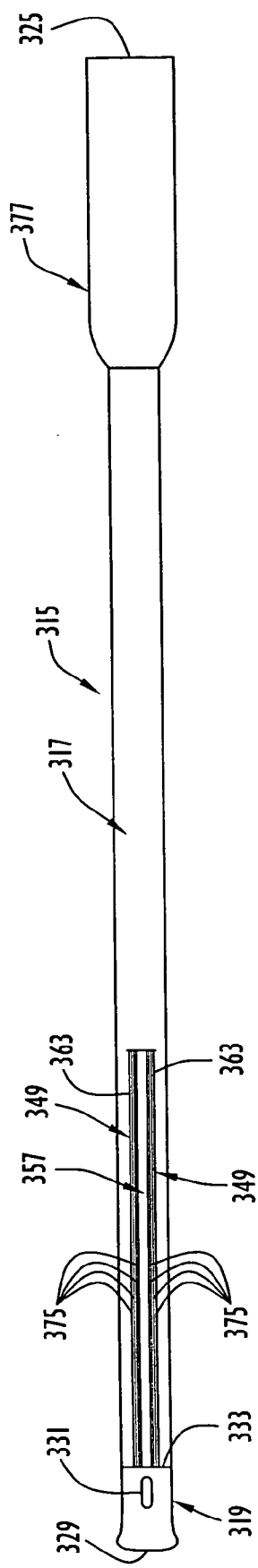
FIG. 27 is a top view of the dilating member.
Figure 28:
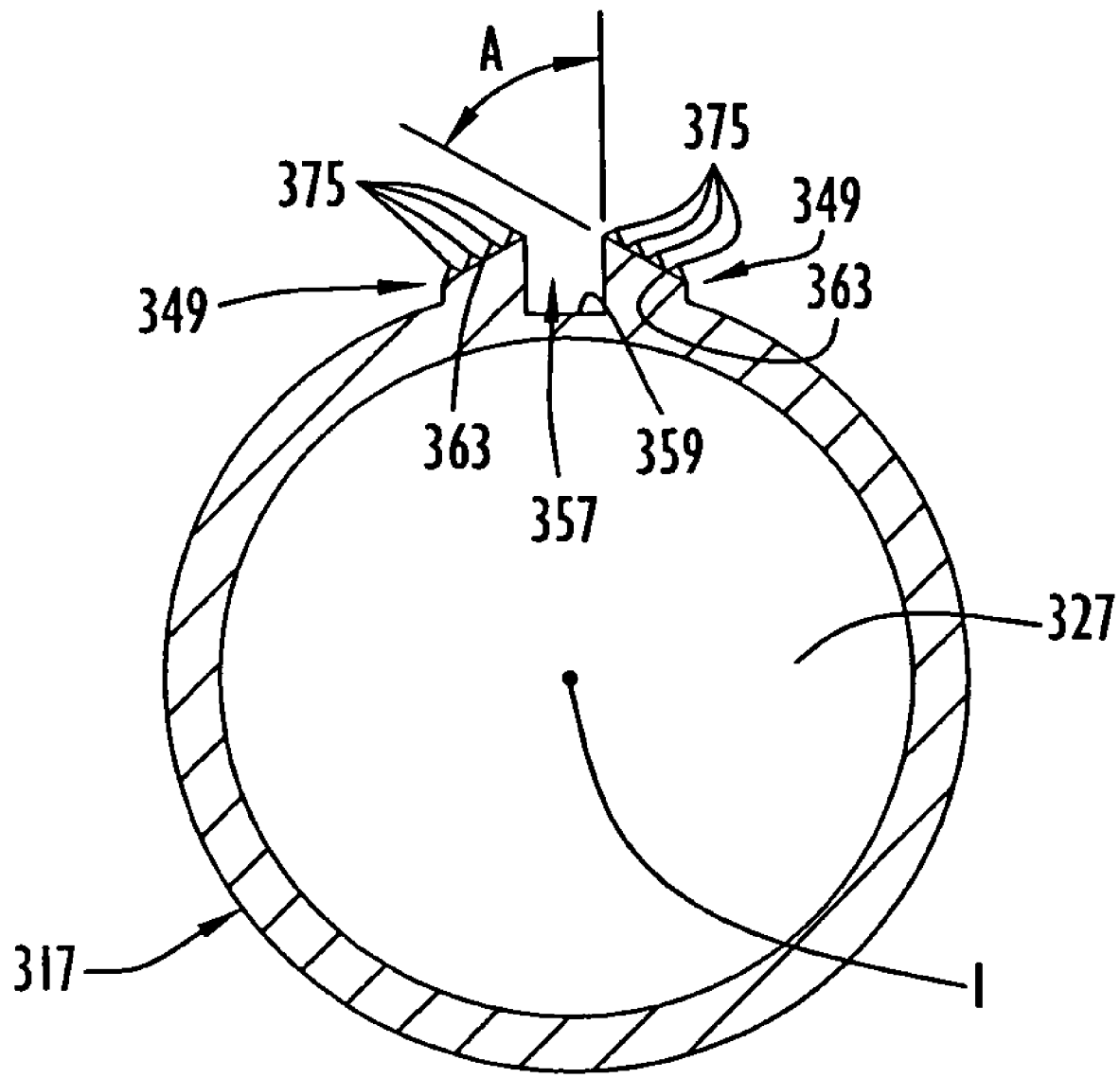
FIG. 28 is a sectional end view through a tubular portion of the dilating member.
Figure 29:
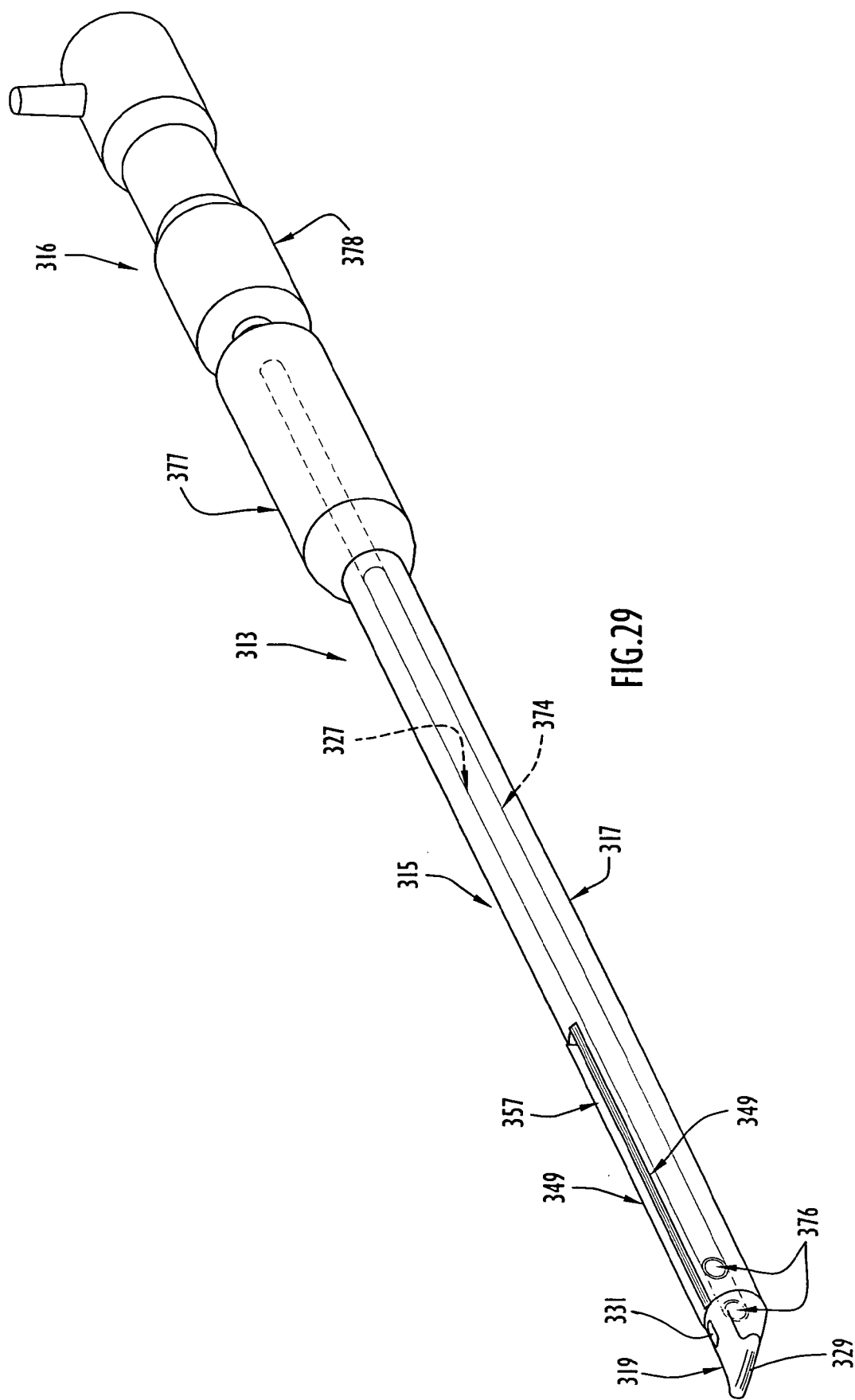
FIG. 29 is a perspective view of the dilating member and an endoscope of the dilating and visualization instrument assembly shown in an assembled condition for the dilating and visualization instrument assembly.

The components of a dilating and visualization instrument assembly 313 for use in an endoscopic carpal tunnel release procedure are depicted in FIG. 25 in an unassembled condition and are depicted in FIG. 29 in an assembled condition. The dilating and visualization instrument assembly 313 comprises a dilating member 315 and an endoscope 316 for being slidably and rotatably received in the dilating member 315. The dilating member 315 is depicted in FIGS. 25-29 and comprises an elongate tubular portion 317 joined to a closed, hollow distal end 319, an interior passage 327 extending through the tubular portion 317, in communication with the interior of distal end 319, an open proximal end 325 in communication with the interior passage 327, and a central longitudinal axis I. The distal end 319 of the dilating member 315 is joined to the tubular portion 317 at a peripheral or circumferential junction 333 and has an external configuration that narrows or tapers in height in a distal direction from the junction 333 toward the top of the dilating member 315 to terminate at a transverse distal, forward or leading nose or edge 329. The leading nose 329 is offset toward the top of the dilating member 315 from a horizontal plane containing the central longitudinal axis I, and extends transverse or perpendicular to the central longitudinal axis I in alignment with a horizontal plane that parallels the horizontal plane containing axis I. Accordingly, the closed distal end 319 has an external beveled configuration in profile with a lower or bottom wall portion thereof forming an acute angle with an upper or top wall portion thereof. The distal end 319 is of increasing width in the distal direction such that the length of the leading nose 329 extending between opposed sides of the distal end 319 transverse or perpendicular to the central longitudinal axis I is greater than the outer diameter or width of the tubular portion 317 of the dilating member 315. As seen in FIGS. 26 and 27, the sides of distal end 319 flare laterally outwardly to the leading nose 329. The leading nose 329 is configured as a narrow but rounded or blunt edge to avoid inflicting unnecessary trauma on anatomical tissue. The leading nose 329 has a central segment perpendicular to the central longitudinal axis I and has arcuate side segments extending respectively from the central segment to the opposed sides of distal end 319. An aperture 331 is formed in the top wall portion of the distal end 319 and provides communication with the interior of distal end 319 and with the passage 327. The aperture 331 may have an oval or oblong peripheral configuration with its length or major dimension extending longitudinally along the distal end 319 in parallel with the central longitudinal axis I. The tubular portion 317 can be cylindrical in configuration.

A pair of raised external ridges 349 separated by a gap or depression 357 extend longitudinally along a distal length section of the tubular portion 317 of the dilating member 315. The ridges 349 begin at, adjacent or near the junction 333 and extend longitudinally along the top of the dilating member 315 in parallel with the central longitudinal axis I. The ridges 349 have respective inner side surfaces extending upwardly from a base surface 359 of depression 357 to upper or top surfaces 363 of the ridges. The base surface 359 lies within the wall of the tubular portion 317, and the depression 357 is located between the inner side surfaces of the ridges 349. The inner side surfaces of the ridges 349 may be planar and may be parallel to one another as well as being perpendicular to the horizontal plane containing the central longitudinal axis I of the dilating member 315. The top surfaces 363 of the ridges 349 are angled downwardly from the upper edges of the corresponding inner side surfaces and are connected with the wall of the tubular portion 317. Each top surface 363 is thusly disposed at an acute angle A to its corresponding inner side surface, and the top surfaces 363 may be planar. The top surfaces 363 are serrated in a longitudinal direction to present a plurality of cutting edges or teeth 375 raised or elevated from the tubular portion 317 and extending longitudinally along each top surface 363 in parallel with the central longitudinal axis I of the dilating member 315. The dilating member 315, or at least the distal length portion thereof, may be made of clear or transparent material including plastic such as polycarbonate. A handgrip 377, which need not be transparent, may be provided on the tubular portion 317 of the dilating member 315 at or near the open proximal end 325 to facilitate manual grasping. In the case of dilating member 315, the handgrip 377 has an opening at its rearward end defining the open proximal end 325 of the dilating member, and the tubular portion 317 extends distally from a forward end of the handgrip. The dilating member 315 can be designed for single patient use.

In a representative but not limiting embodiment of dilating member 315, the dilating member 315 has an overall length of or about 18 cm; the tubular portion 317 has an outer diameter of or about 6 mm and an inner diameter of or about 4 mm which is also the diameter of the interior passage 327; the leading nose 329 has a length of or about 6.5 mm; the aperture 331 begins 5 mm or about 5 mm proximally from the leading nose; the aperture 331 has a length of or about 5 mm and a width of or about 2 mm; the ridges 349 have a length of or about 5 cm extending longitudinally along the tubular portion 317 of the dilating member; the depression 357 has a width of or about 2 mm between the inner side surfaces of the ridges; and the top surfaces 363 of the ridges are disposed at an angle A of or about 60° to the corresponding inner side surfaces.

The endoscope 316 may be similar to the endoscope 16, and the same endoscope used in the cutting and visualization instrument assemblies may be used for the dilating and visualization instrument assembly 313. The dilating member 315 comprises an instrument which, when assembled with an endoscope, forms a dilating and visualization instrument assembly. As depicted in FIG. 29, the dilating and visualization instrument assembly 313 is assembled by inserting the endoscope 316, distal end first, in the open proximal end 325 of the dilating member 315 such that the shaft 374 of the endoscope is slidably and rotatably received concentrically or coaxially in the passage 327 with a close fit. The endoscope 316 is advanced longitudinally distally in the passage 327 to position the image obtaining end 376 of the endoscope 316 in alignment or substantial alignment with the aperture 331 to provide visualization through the aperture. In addition, the endoscopic 316 can provide visualization through the transparent wall of the dilating member 315 in various longitudinal and/or rotational positions for the endoscope within the dilating member. The dilating and visualization instrument assembly 313 is particularly advantageous for creating and/or enlarging a subligamentous space in the subligamentous plane between the transverse carpal ligament and the flexor tendon synovium sheath to accommodate subsequent insertion of the cannula of a cutting and visualization instrument assembly, and for removing adhered synovium from the lower surface of the transverse carpal ligament in an endoscopic or minimally invasive carpal tunnel release procedure as described further below.

An endoscopic or minimally invasive carpal tunnel release procedure is described with reference to FIGS. 30-35. The endoscopic carpal tunnel release procedure can be performed in an outpatient surgery center or office operating room setting under a general, regional or local anesthetic. Standard operating room equipment used in the procedure includes an endoscope, such as endoscope 216, which is coupled with a light source and with a video camera and monitor (not shown) in a conventional manner. The monitor, which displays the images obtained by the image obtaining end 276 of the endoscope, may be supported on a rolling tower or cart for selectively positioning the monitor to be comfortably and conveniently viewed by the surgeon.

Figure 30:
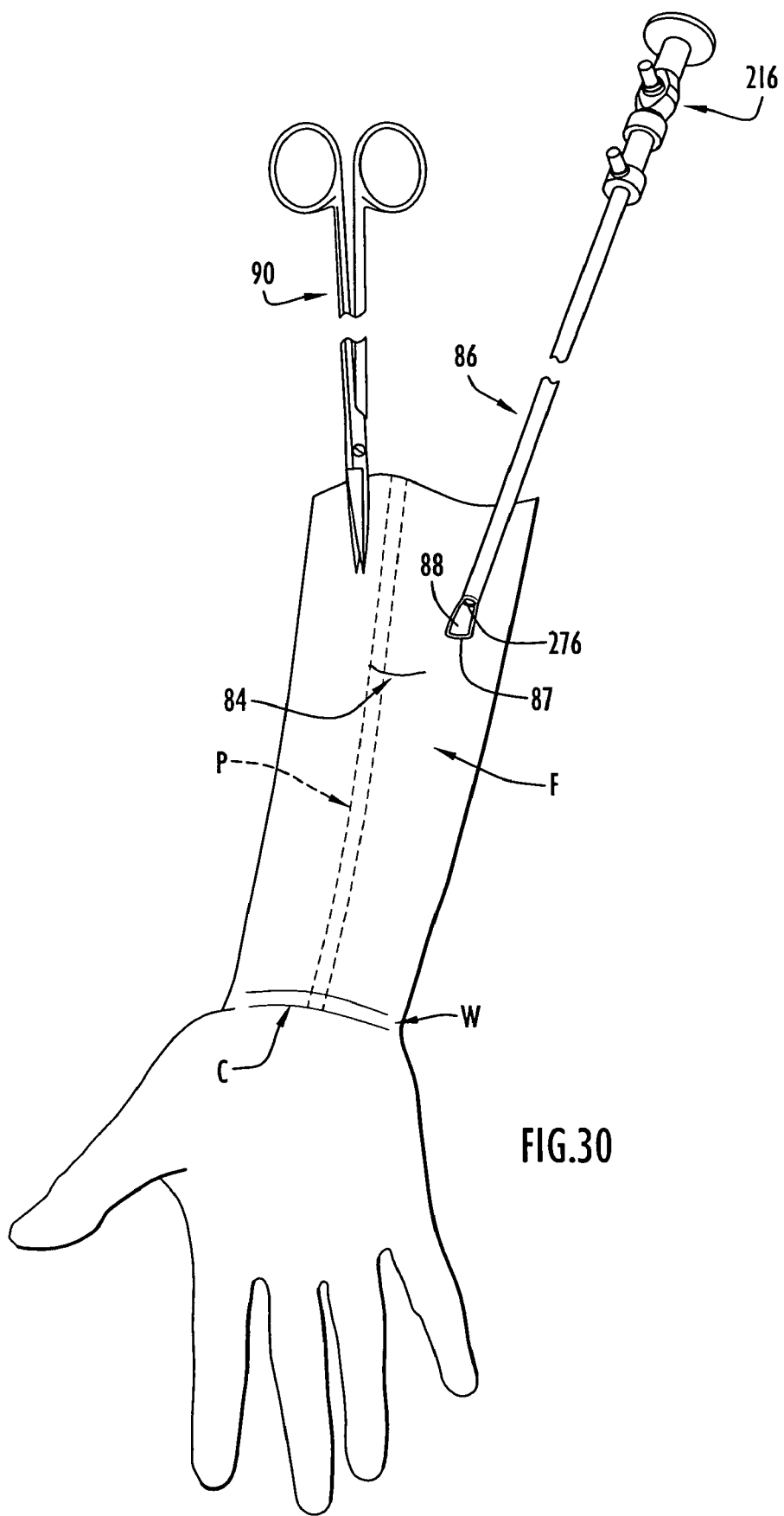
FIG. 30 is a broken perspective view of a wrist and forearm depicting the initial steps in a minimally invasive carpal tunnel release procedure involving creation of a pathway by dissection from an incision along the mid-volar forearm into the carpal tunnel under direct endoscopic visualization.

The arm and correct wrist W to be operated on are supported with the palm and volar aspect of the wrist W and forearm F facing upwardly. As shown in FIG. 30, an entry or access portal or incision 84, typically about 2.5 cm in length, is made in the mid-volar forearm F at a location 6-7 cm proximal of the distal wrist flexion crease C visible in the patient's skin along the volar aspect of the wrist W. This location for the entry incision is favorable because it is in an anatomically safe area well away from the sensitive and critical anatomical tissue and structures of the wrist W. The endoscope 216 is initially removably assembled to a retractor 86 so that a retractor head 87 of the retractor 86 extends from the image obtaining end 276 of the endoscope. The retractor head 87 can have a spatula shape or any suitable configuration or shape conducive to retracting, separating, elevating, displacing, supporting and/or manipulating anatomical tissue and structures in subcutaneous regions to create room for the insertion of other instruments and/or to clear a field of view for endoscopic visualization by the image obtaining end 276. The retractor head 87 is depicted as having a spatula shape circumscribing a void 88, and the image obtaining end 276 may be positioned to face the void 88 to permit visualization therethrough.

Standard endoscopic surgical scissors 90 of suitable length are inserted in the incision 84 and used to begin blunt dissection of the superficial fascia from the deep fascia of the forearm F. The retractor head 87, with the endoscope 216 attached thereto, is inserted through the incision 84 and positioned to elevate or separate the dissected superficial fascia from the deep fascia. Dissection of the superficial fascia from the deep fascia using the scissors 90 or other suitable instrument is continued distally toward the wrist W under continuous endoscopic visualization provided by the endoscope 216 attached to the retractor head 87 which is used to elevate or separate the dissected superficial fascia from the deep fascia. Elevating or separating the superficial fascia from the deep fascia using the retractor head 87 clears a field of view for the image obtaining end 276 of the endoscope to visualize the dissection and creates room for the scissors 90 or other suitable instrument to continue the dissection. The endoscope 216 directly guides dissection along the forearm F toward the wrist W and allows the anatomy of the volar forearm, including the palmaris longus tendon P, to be observed as dissection is continued distally toward the wrist. Upon reaching the wrist W, approximately at or proximally near the location of the distal flexion crease C, the deep fascia is opened, preferably via blunt spreading dissection using the scissors 90 or another suitable spreading instrument, to expose the median nerve N, flexor tendon synovial sheath S (ulnar bursa) and proximal entry into the carpal tunnel under direct endoscopic visualization provided by endoscope 216 and facilitated by use of the retractor head 87 to manipulate anatomical tissue and/or structures. Dissection to establish a proximal entry into the carpal tunnel under direct endoscopic visualization avoids the blind insertion of instruments into the carpal tunnel, avoids the adverse consequences of a blind entry, and also avoids injury to the sensory branch of the median nerve which gives sensation to the volar forearm. Once the proximal entry into the carpal tunnel has been exposed, the scissors 90 or other spreading instrument is withdrawn through the incision 84. As a result of dissection from the incision 84 into the carpal tunnel, a subcutaneous pathway or tunnel 92 is formed from the incision 84 leading into the carpal tunnel for the subsequent introduction of instruments into the carpal tunnel. The endoscope 216 is used to locate and visualize important anatomical structures including the median nerve N, the flexor tendon synovial sheath S containing the flexor digitorum superficialis tendons and the flexor digitorum profundis tendons, and the transverse carpal ligament T prior to inserting any instruments in the carpal tunnel.

The transverse carpal ligament T characteristically is very white in color and has transverse striations extending in the ulnar to radial directions. Endoscopic visualization of the white color and transverse striations assists in identifying the transverse carpal ligament T. Endoscopic identification of the median nerve N is assisted by observing the characteristic yellow-white color of the median nerve and the slight movement of the nerve capable of being elicited in response to gentle rocking of an instrument clockwise and counterclockwise as described further below. Endoscopic identification of the flexor digitorium superficialis tendons is assisted by observing their characteristic off-white color and dramatic movement when the long and ring fingers are flexed and extended at the proximal interphalangeal joints.

Once the known anatomy including the median nerve N, flexor tendon synovial sheath S and transverse carpal ligament T have been identified with confidence through endoscopic visualization, one or more standard dilators (not shown) may be introduced into the carpal tunnel through the incision 84 and the previously created pathway 92 to create and/or enlarge a subligamentous space in the carpal tunnel beneath the transverse carpal ligament T along the subligamentous plane between the ligament T and the flexor tendon synovial sheath S large enough in size to accommodate the cannula of the cutting and visualization instrument assembly to be used in the procedure. The one or more dilators are introduced in the carpal tunnel while the retractor head 87 and endoscope 216 remain in place at the operative site to displace or retract anatomical tissue and/or structures as needed to facilitate insertion of the dilators while providing continuous endoscopic visualization as the dilators are inserted. A 5 mm dilator may be inserted first in the carpal tunnel just beneath the transverse carpal ligament T, above the flexor tendon synovial sheath S, and alongside the ulnar aspect or side of the median nerve N to create and/or enlarge the subligamentous space in the carpal tunnel. The dilator is used to push the flexor tendon synovial sheath S away from the transverse carpal ligament T and is inserted on the ulnar aspect of the median nerve N so as to push the median nerve toward the thumb, thusly separating it from the flexor tendons. After withdrawing the first dilator through the incision 84, a second larger size dilator, typically a 7 mm dilator, may be inserted in a manner similar to the first smaller size dilator to further dilate or enlarge the subligamentous space under direct endoscopic visualization. The subligamentous space, as enlarged by the 7 mm dilator, will be large enough in size to accommodate the cannula of the cutting and visualization instrument assembly. As the dilators are inserted in the carpal tunnel, the wrist W may be gently flexed in the volar and dorsal directions to facilitate passage of the dilators along the subligamentous plane. Accordingly, the hand is not required to be rigidly secured in hyperextension during the minimally invasive carpal tunnel release procedure. The median nerve N and other anatomical structures are thusly not held in a fixed, rigid position which reduces the risk of injury to the median nerve and such other structures when instruments are inserted in the carpal tunnel. Furthermore, allowing for movement of the fingers provides movement of various anatomical structures in a relative fashion which assists in identifying such structures with confidence by endoscopic visualization. For example, flexion and extension at the proximal and distal interphalangeal joints causes selective movement of the flexor digitorium superficialis and flexor digitorium profundis tendons but relatively minimal movement of the median nerve which assists in confirming the identity and location of those structures endoscopically.

The distal end configuration of standard dilators requires that an exceptionally high level of skill be employed to guide the dilators along the upward proximal to distal slope of the subligamentous plane without the dilators penetrating or snagging in or on the synovium of sheath S as they are inserted between the transverse carpal ligament T and the flexor tendon synovial sheath S. If the dilators penetrate or snag in or on the synovium, the clarity of endoscopic visualization carried out from the subligamentous space created and/or enlarged by the dilators may be impaired or obstructed by synovial tissue, making it more difficult to accurately or confidently identify anatomical tissue and/or structures in the carpal tunnel. For example, the synovial tissue may present a film that distorts the color, texture and/or visual detail of the endoscopic images and may interfere with endoscopic visualization of the striations along the lower or dorsal facing surface of the transverse carpal ligament T. Moreover, some synovium may remain attached or adhered to the lower surface of the transverse carpal ligament T when the flexor tendon synovial sheath S is separated from the transverse carpal ligament T to create and/or enlarge the subligamentous space. The adhered synovium may interfere with and impair endoscopic visualization of the striations along the lower surface of the transverse carpal ligament T and may adversely impact or retard the cutting procedure by which the ligament is divided. The dilating and visualization instrument assembly 313 is particularly useful as an alternative or in addition to standard dilators to better create and/or enlarge the subligamentous space without penetrating or snagging on or in the synovium, and/or to remove adhered synovial tissue from the lower surface of the transverse carpal ligament T.

Figure 31:
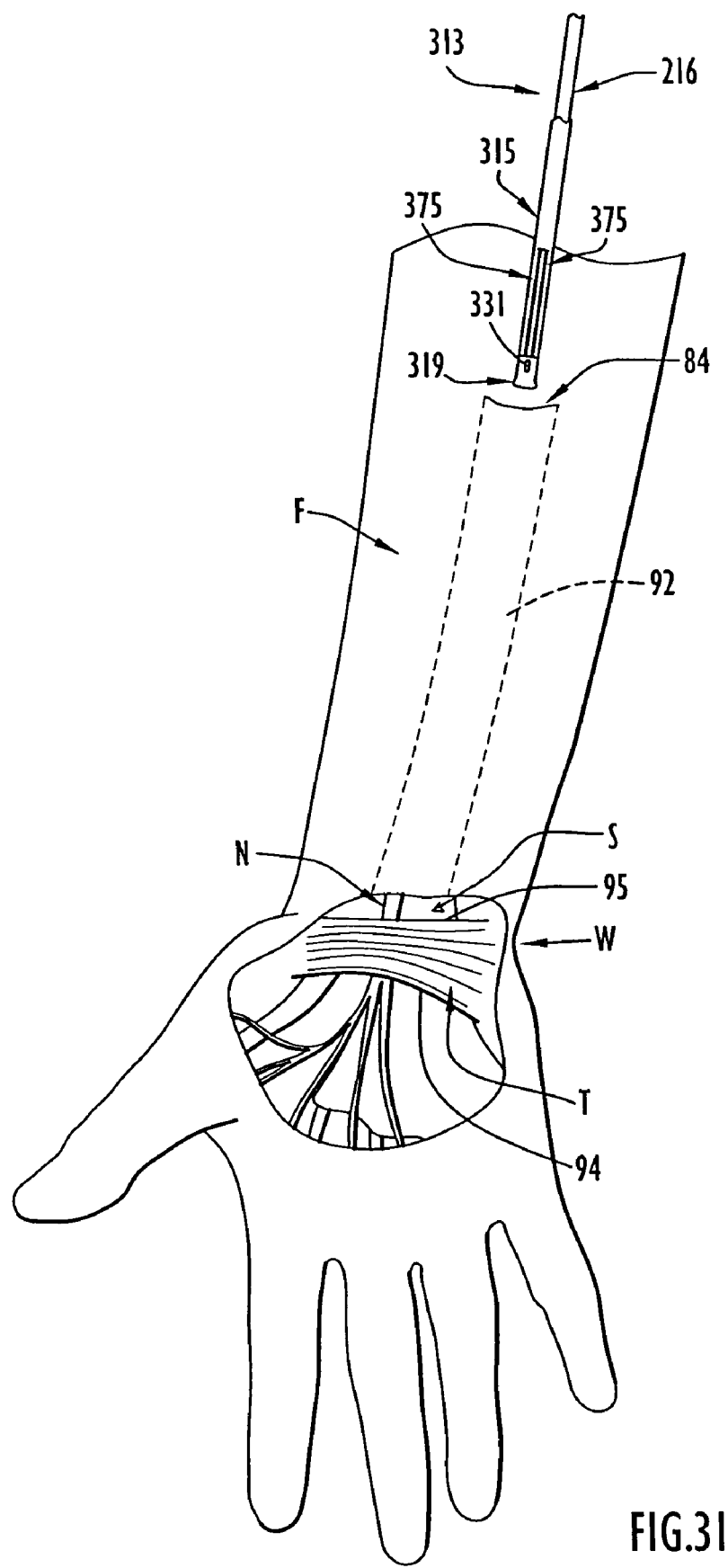
FIG. 31 is a broken perspective view of the wrist, with the transverse carpal ligament exposed, and forearm depicting insertion of the dilating and visualization instrument assembly in the incision for advancement along the pathway into the carpal tunnel.
Figure 32:
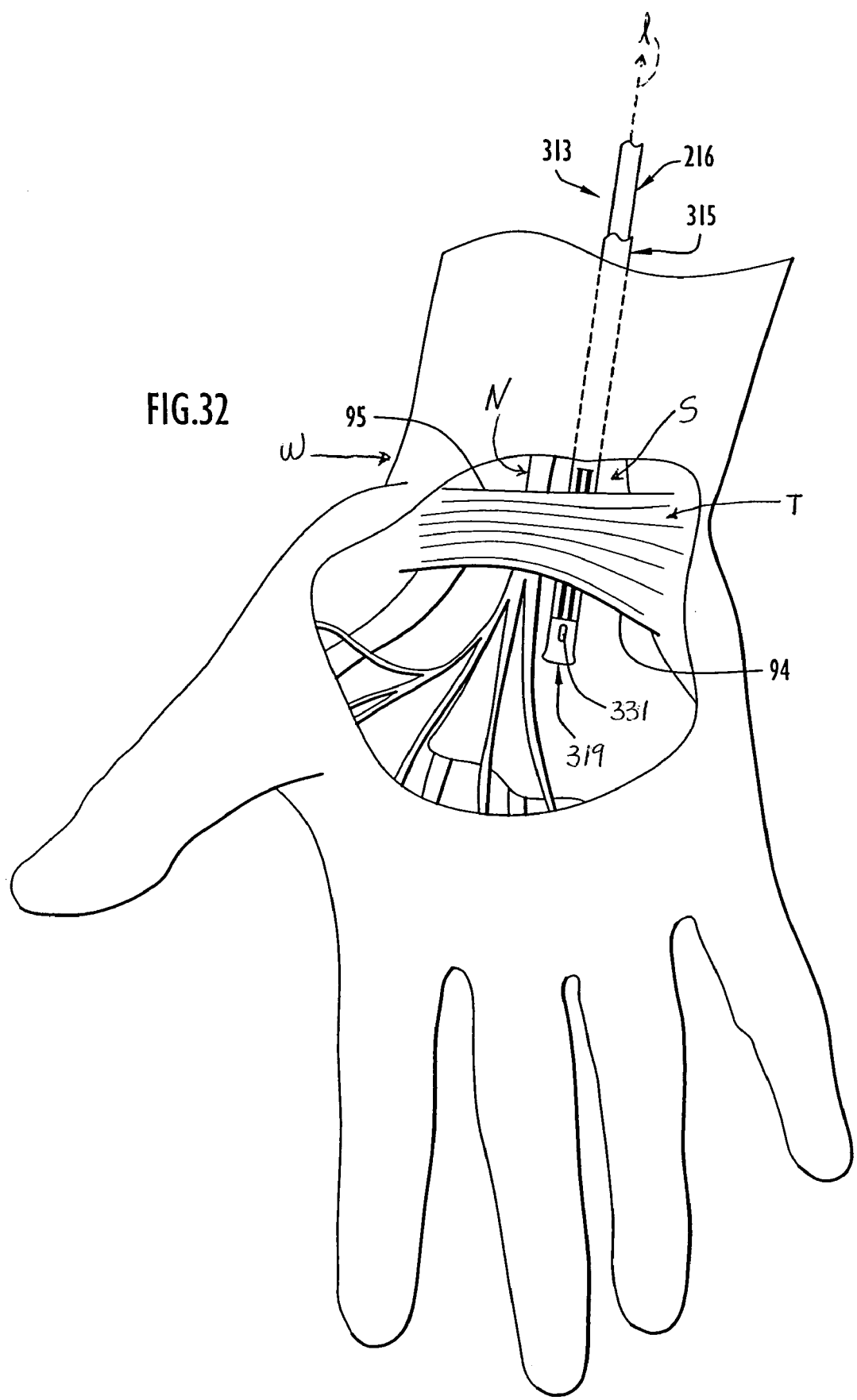
FIG. 32 is a broken perspective view depicting the dilating and visualization instrument assembly introduced in the carpal tunnel of the wrist along the subligamentous plane between the transverse carpal ligament and the flexor tendon synovial sheath to create and/or enlarge a subligamentous space.

The dilating and visualization instrument assembly 313 may be inserted in the carpal tunnel in place of a standard dilator to create and/or enlarge the subligamentous space, and/or it may be inserted in a subligamentous space previously created and/or enlarged by one or more standard dilators. Use of the dilating and visualization instrument assembly 313 in the minimally invasive carpal tunnel release procedure is described below with the endoscope 216 comprising the endoscopic of the dilating and visualization instrument assembly. However, it should be appreciated that the endoscope 316 or any other suitable endoscope can be used in the dilating and visualization instrument assembly. As shown in FIG. 31, the dilating member 315 is inserted, distal end 319 first, in the carpal tunnel via the incision 84 and the previously created pathway 92. The dilating member 315 may be inserted in the carpal tunnel while the retractor head 87 and endoscope 216 attached thereto are in place at the operative site to facilitate insertion of the dilating member 315 while providing continuous endoscopic visualization as the dilating member is inserted in the carpal tunnel. Alternatively, the dilating member 315 can be inserted in the carpal tunnel via the incision 84 and pathway 92 with the endoscope 216 received within the dilating member to provide endoscopic visualization through aperture 331 and/or through the transparent wall of the dilating member. The endoscope 216 can be selectively positioned longitudinally and rotatably within the dilating member 315 to orient the image obtaining end 276 to face in a desired rotational direction at a selected longitudinal location. As seen in FIG. 32, the dilating member 315 is advanced distally within the carpal tunnel along the upwardly sloping subligamentous plane, with the aperture 331 and cutting edges 375 facing upwardly or in the volar direction. The configuration of the distal end 319 facilitates distal advancement of the dilating member 315 along the subligamentous plane by guiding the dilating member to follow the upward slope of the subligamentous plane without the dilating member penetrating or snagging in or on the synovium of the flexor tendon synovial sheath S. In particular, the configuration of distal end 319 makes the dilating member 315 advantageous for separating the synovial sheath S from the transverse carpal ligament T by non-traumatically pushing the synovial sheath downwardly in the dorsal direction away from the transverse carpal ligament as the dilating member is advanced distally between the ligament and the synovial sheath. It is preferred that the dilating member 315 be advanced far enough distally for the distal end 319 to extend beyond the distal edge 94 of the transverse carpal ligament T and create a space, which is essentially a distal extension or continuation of the subligamentous space, in the fat that lies under the deep fascia extending distally beyond the transverse carpal ligament T, around the superficial palmar arch artery, and between the median nerve and flexor digitorum superficialis tendons. It is preferred that the dilating member 315 enter and advance through the proximal portion of the carpal tunnel with the hand dorsiflexed, and that the dilating member move through the mid and distal portions of the carpal tunnel with the hand volar flexed. Entry and distal advancement of the dilating member 315 in the carpal tunnel occurs under direct endoscopic visualization by which important anatomical structures can be identified and inadvertent injuries to such anatomical structures can be averted.

Figure 33:
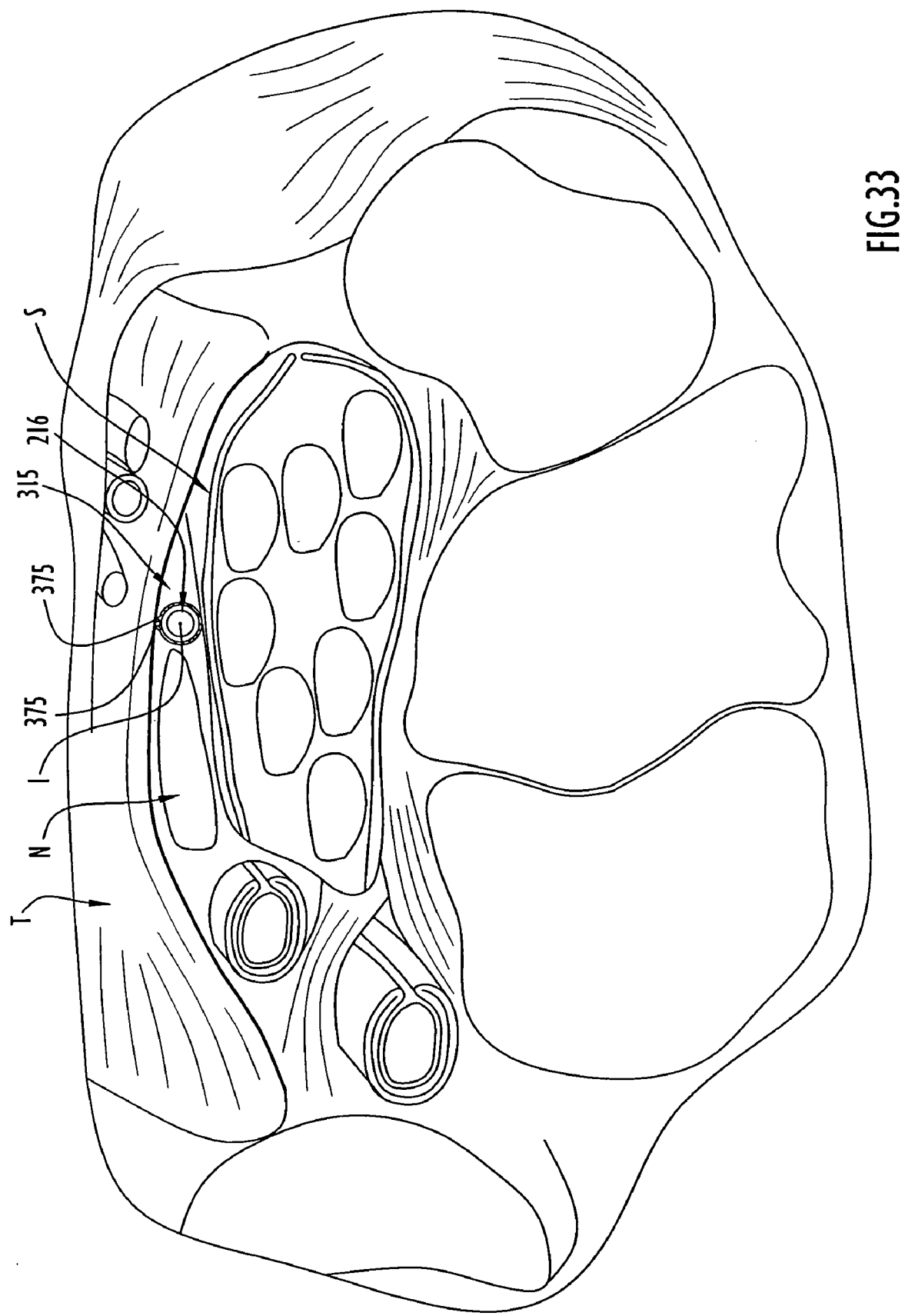
FIG. 33 is a sectional view of the carpal tunnel illustrating removal of adhered synovium from the lower surface of the transverse carpal ligament using the dilating and visualization instrument assembly.

Once the dilating member 315 has been advanced distally through the carpal tunnel the appropriate distance and the endoscope 216 has been used to visualize important anatomical structures from within the dilating member, the dilating and visualization instrument assembly 313 is gently elevated upwardly or in the volar direction to position the cutting edges 375 in close contact with the lower surface of the transverse carpal ligament T as seen in FIG. 33. Elevation of the dilating member 315 in this manner is performed by manual manipulation of the proximal end 325 which remains exteriorly of the patient's body. The cutting edges 375, which extend transverse to the length of the ligament T and in the same direction as the ligament width, are preferably of sufficient length to span the entire width of the ligament T from its distal edge 94 to its proximal edge 95. With the cutting edges 375 in contact with the lower surface of the transverse carpal ligament T, the dilating member 315 is rotated or rocked back and forth clockwise and counterclockwise about its central longitudinal axis I such that the cutting edges 375 abrade or remove from the lower surface of the ligament any attached or adhered synovium. The synovium that is abraded or removed from the lower surface of the transverse carpal ligament T collects in depression 357 for removal from the operative site when the dilating member 315 is withdrawn from the operative site and from the patient's body. Removal of attached or adhered synovium from the lower surface of the transverse carpal ligament can be observed and confirmed endoscopically via the endoscope 216 within the dilating member 315. Thereafter, the dilating and visualization instrument assembly 313 is withdrawn from the carpal tunnel and is withdrawn from the patient's body through the incision 84. The dilating and visualization instrument assembly 313 can be withdrawn while in its assembled condition. Alternatively, the endoscope 216 can be withdrawn first, followed by withdrawal of the dilating member 315.

Once the subligamentous space has been prepared, the cannula of a cutting and visualization instrument assembly is inserted, distal end first, through the incision 84, the previously prepared pathway 92 and into the subligamentous space under direct endoscopic visualization. Although the minimally invasive carpal tunnel release procedure is explained herein with the cutting and visualization instrument assembly 210 and the visualization instrument assembly 211 being used in the procedure, it should be appreciated that any of the various cutting and visualization assemblies and visualization assemblies of the present invention can be used in the procedure. The cannula 212, without the cutting member 214 or endoscope 216 received therein, can be inserted, distal tip 220 first, in the subligamentous space with the retractor 86 and attached endoscope 216 positioned to retract or displace anatomical tissue and/or structures to facilitate insertion of the cannula 212 while providing continuous direct endoscopic visualization. Alternatively, as shown in FIG. 33, the cannula 212 can be inserted with the endoscope 216 received therein to form the visualization instrument assembly 211, the endoscope 216 providing visualization through slots 226, 230a, 230b and/or 230c, through the window 252, and/or through the transparent wall of the tubular member 218. Endoscopic visualization obtained via slots 226, 230a, 230b and/or 230c and/or through window 252 is preferable for its better visual quality as compared with endoscopic visualization obtained through the wall of tubular member 218. In addition, the slots and window provide an air interface that enhances endoscopic visualization as explained further below.

Figure 34:
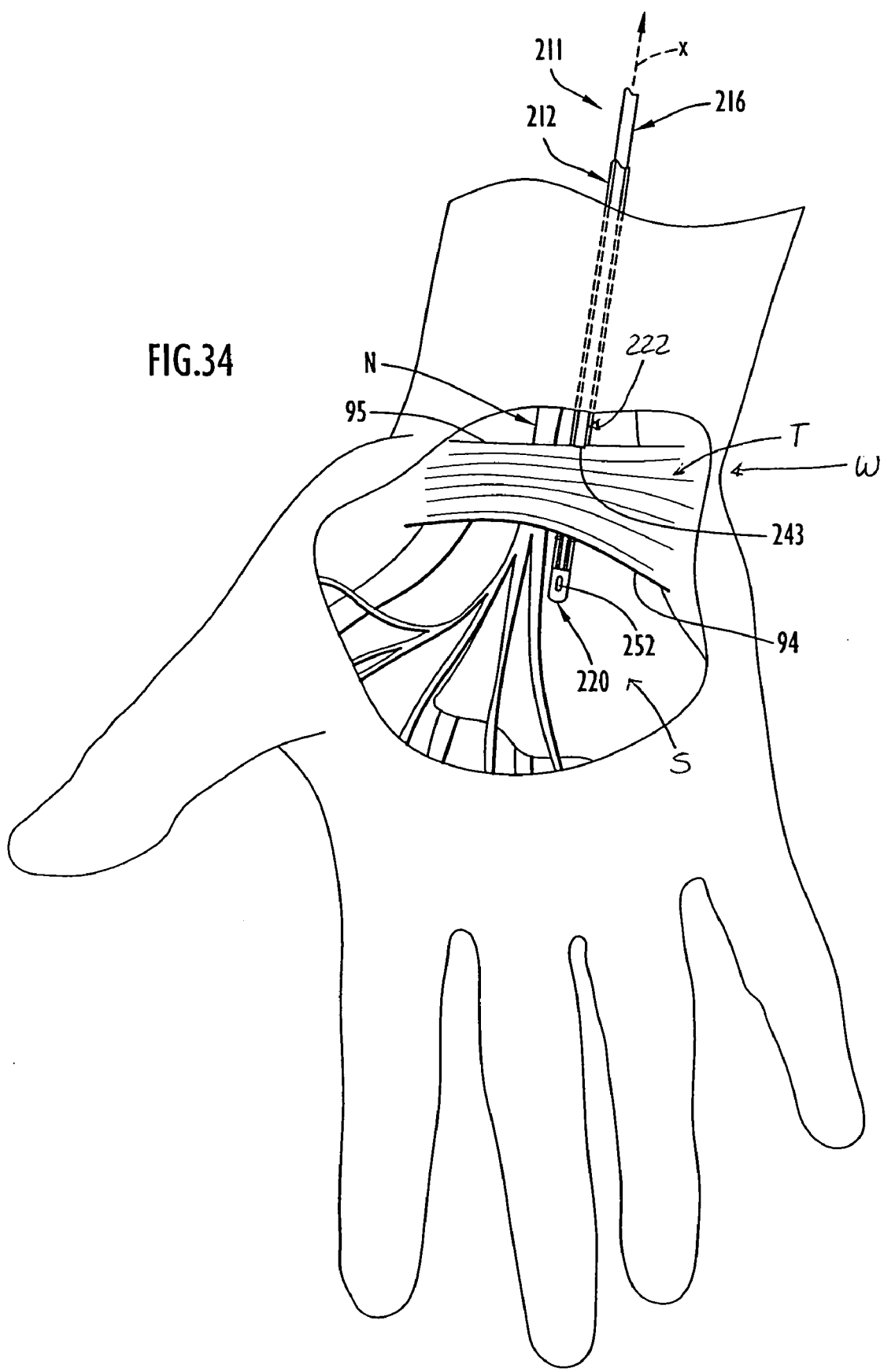
FIG. 34 is a broken perspective view showing the preferred visualization instrument assembly introduced in the subligamentous space to provide endoscopic visualization prior to division of the transverse carpal ligament.

The cannula 212 is introduced in the subligamentous space with the blade housing 222, the slot 226 and the window 252 facing upwardly or in the volar direction. The cannula 212 is advanced distally in the subligamentous space, which follows the subligamentous plane, so that the distal tip 220 passes distally beyond the distal edge 94 of the transverse carpal ligament T and can be seen externally creating a bulge in the mid-palm. In this position for the cannula 212, which may be considered a cutting position, the transverse carpal ligament T extends across the slot 226 transverse to the central longitudinal axis x of the cannula 212, and the entire width of the transverse carpal ligament T from its proximal edge 95 to distal edge 94 is contained between the forward end of blade housing 222 and the forward edge of slot 226. Also, the entire thickness of the transverse carpal ligament T between its upper or volar facing surface and its lower surface is accommodated in the recess 245 defined by the forward end surface of the blade housing 222, and the ledge 243 may lock in or on the ligament to hold it in position over the slot. For example, the ledge 243 may curve over the upper surface of the ligament T to hold the proximal edge 95 of the ligament in place adjacent the forward end of blade housing 222 as depicted in FIG. 34. The slot 226 defines a cutting line or zone along which the ligament T is to be cut, severed or divided from its proximal edge 95 to its distal edge 94 by the cutting member 214. The slot 226 establishes the location of the cutting zone in the mid-portion of the ligament T between the opposed ends of the ligament that are attached to the wrist bones. The window 252 is located distally beyond the distal edge 94 of the transverse carpal ligament T and, therefore, is located to provide endoscopic visualization distally of the cutting zone. During insertion of the cannula 212, the hand may be flexed to facilitate insertion as described above for the standard dilators and for dilating member 315. If the endoscope 216 has been providing visualization while attached to the retractor 86 and is not already received in the cannula 212, it should be inserted in the cannula 212 once the cannula is correctly positioned snugly in the carpal tunnel.

In contrast to the distal tip configurations of prior art instruments for minimally invasive carpal tunnel release, the configuration of distal tip 220, as well as that of distal tips 20 and 120, promotes smooth distal advancement of the cannula, assists in guiding the cannula to follow the slope of the subligamentous plane, and gently displaces anatomical tissue and/or structures to make way for insertion of the cannula. The configuration of distal tip 220, and that of distal tips 20 and 120, minimizes the resistance to insertion of the cannula presented by anatomical tissue and/or structures compared to the greater resistance to insertion encountered with the open ended and/or blunt configured distal tips of the prior art instruments. The exterior protuberances 232 add structural strength and rigidity to the cannula 212 and better enable the cannula to follow the subligamentous plane. The protuberances 232 assist in stabilizing the cannula 212 in the carpal tunnel so that the cannula does not deviate from the cutting position. The protuberances 232 enable the cannula 212 to resist rotation and to maintain the cutting zone at a fixed location on the ligament T. The protuberances 232 also assist in maintaining the slots in the cannula 212 unobstructed by anatomical tissue and/or structures so as to maintain a clear field of view for the endoscope 216 from within the cannula 212. However, the cannula 212 can still be intentionally rotated or rocked back and forth from the cutting position about its central longitudinal axis x in the radial and ulnar directions via manipulation of the handgrip 253 to effect some displacement of adjacent anatomical tissue and/or structures, which displacement is assisted by the protuberances 232. Intentional displacement of anatomical tissue and/or structures as assisted by the protuberances 232 may be useful for facilitating insertion of the cannula, establishing the correct cutting position for the cannula, displacing tissue and/or structures to avoid injury, clearing the slots and/or window in the cannula from obstruction by anatomical tissue and/or structures, orienting the cannula to obtain a desired field of endoscopic view, orienting the cannula to locate particular anatomical features, and/or facilitating positive identification of anatomical tissue and/or structures.

The endoscope 216 received in the cannula 212 is used to visualize anatomical tissue and/or structures in and adjacent the carpal tunnel and in relation to the cannula 212. With the cannula 212 in the cutting position, the image obtaining end 276 of the endoscope 216 can be positioned in the cannula 212 to provide endoscopic visualization of the transverse carpal ligament T through the slot 226. Endoscopic observation of the color, striations, and direction of the striations of the ligament T assist in confirming the identity of the ligament. When the cannula 212 is rotated from the cutting position as described above, the transverse carpal ligament T does not move, and the immovability of the ligament further assists in confirming its identification. When the image obtaining end 276 is rotated toward the radial slot 230c located adjacent median nerve N when the cannula 212 is in the cutting position, the median nerve N can be endoscopically observed and evidenced by its color and by slight movement of the nerve caused by gentle rotation or rocking back and forth of the cannula 212 from the cutting position. Endoscopic visualization obtained by rotating the image obtaining end 276 respectively toward the ulnar and dorsal slots 230a and 230b when the cannula 212 is in the cutting position provides views of the flexor digitorum superficialis tendons. Identification of the flexor digitorum superficialis tendons is assisted by observing their color and dramatic movement in response to flexion and extension of the long and ring fingers at the proximal interphalyngeal joints. When the image obtaining end 276 is positioned in alignment or substantial alignment with the window 252 with the cannula 212 in the cutting position, the area distal to the cutting zone can be endoscopically observed including the superficial palmar arterial arch. Although the image obtaining end 276 can provide endoscopic visualization through the transparent wall of the tubular member 218, visualization through the slots 226, 230a, 230b and 230c and through the window 252 provides greater visual clarity and, therefore, more reliable identification of important anatomical tissue and/or structures. The slots 226, 230a, 230b and 230c and window 252 provide an air interface between the operative site and the image obtaining end 276 within the cannula 212. The separation provided by these air interfaces keeps the image obtaining end 276 clear and provides better visual detail resulting in quicker and more reliable identification of anatomical features. The rim formations 237 and associated indicia 241 provide reference points to assist in confirming correct placement and orientation of the cannula 212 and in identifying and evaluating various anatomical features. The reference points are useful for gauging the locations and sizes of various anatomical features.

Once the key anatomical structures, including the transverse carpal ligament T, the median nerve N, flexor tendons and superficial palmar arterial arch, have been located and positively identified endoscopically, and the cannula 212 is in the cutting position, it is advisable to obtain a final endoscopic view through the volar slot 226 and the window 252 prior to cutting the transverse carpal ligament. Endoscopic visualization along slot 226 allows the full width of the transverse carpal ligament to be observed. Visualization through window 252 allows the superficial palmar arterial arch to be observed to ensure that it is safely away from the cutting zone. With the cannula 212 maintained in the correct cutting position, the endoscope 216 is then withdrawn from the cannula and the cutting member 214 is inserted in the cannula with the endoscope 216 received in or subsequently inserted in the cutting member 214. The cutting member 214 is inserted, distal end 358 first, in the open proximal end of cannula 212 with the cutting blade 262 received in slot 226 and extending through slot 226 into the channel 244 of blade housing 222. The blade 262 is thusly shielded and not exposed until the cutting member 214 is moved far enough distally within the cannula 212 for the blade 262 to exit the open forward end of blade housing 222 which is adjacent the proximal edge 95 of the transverse carpal ligament T. Prior to moving the cutting member 214 far enough distally for the blade 262 to exit the blade housing 222 and begin division of the ligament T, the endoscope 216 may be moved distally relative to the cutting member 214 to position the image obtaining end 276 distally beyond the forward end of blade housing 222 and the open distal end 258 of the cutting member 214 for endoscopic visualization prior to cutting. With the blade 262 still disposed in blade housing 222, the endoscope 216 can be selectively moved longitudinally and/or rotatably within the cutting member 214 to position the image obtaining end 276 for endoscopic visualization through any of the slots 226, 230a, 230b and 230c and/or window 252 of cannula 212.

Figure 35:
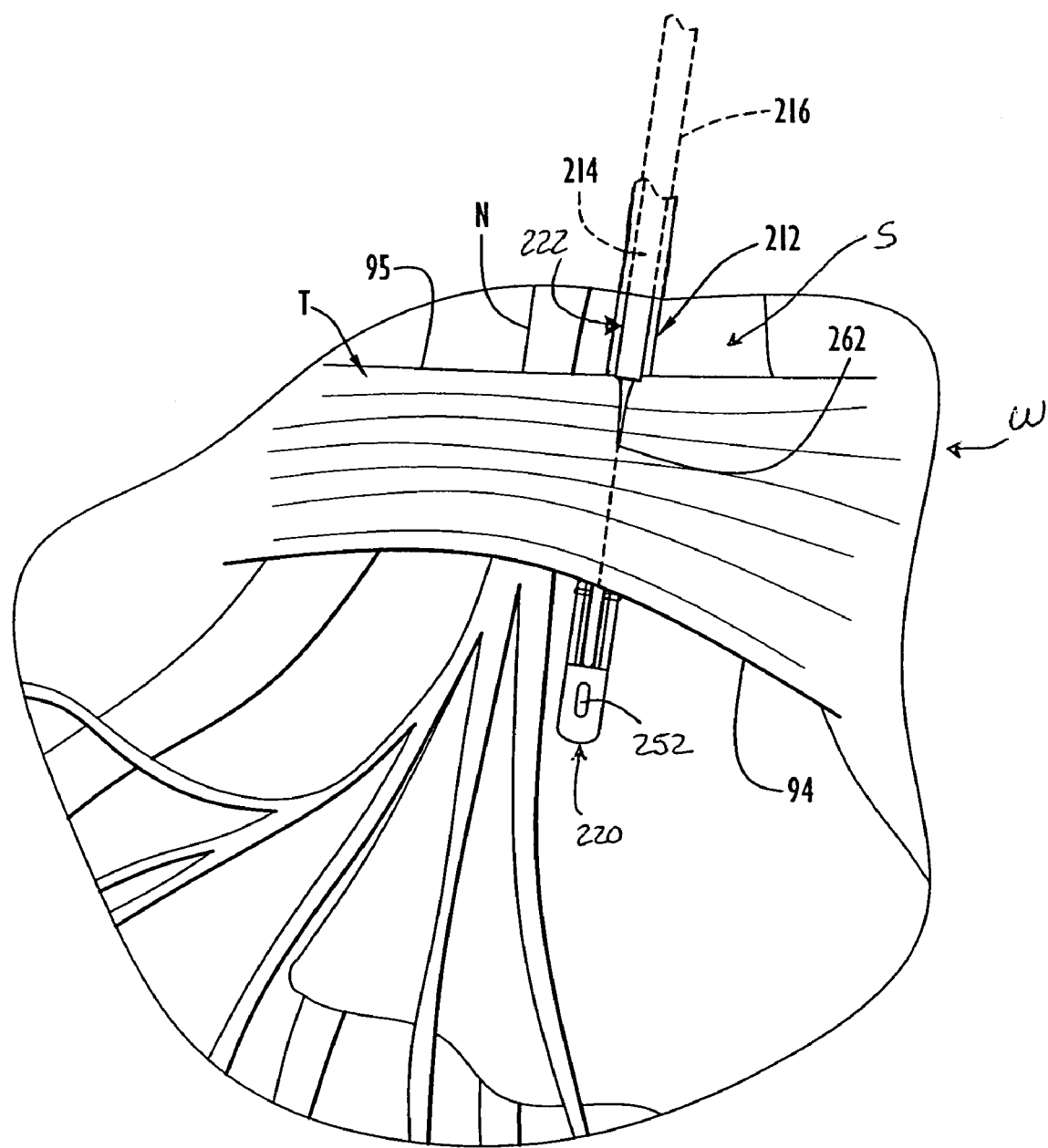
FIG. 35 is a broken perspective view of the wrist depicting division of the transverse carpal ligament using the preferred cutting and visualization instrument assembly.

Upon final endoscopic confirmation that the cannula 212 is in the correct cutting position and that cutting of the ligament T can be safely performed, the endoscope 216 is moved proximally within the cutting member 214 so that the image obtaining end 276 is located to face slot 266 just proximal to the cutting blade 262. The cutting member 214 and endoscope 216 are then advanced distally in tandem within the cannula 212. The ribs 247 of cannula 212 assist in centering the cutting member 214 within the cannula 212, provide a cushioning effect for the cutting member, and promote smooth continuous gliding movement of the cutting member within the cannula. As the cutting blade 262 exits and is extended distally from the forward end of the blade housing 222, the cutting edge of the blade 262 comes into contact with the proximal edge 95 of the ligament T. As illustrated in FIG. 35, continued distal advancement of the cutting member 214 and endoscope 216 in tandem within cannula 212 causes the blade 262 to cut, sever or divide the ligament T along the cutting zone or line established by slot 226. The image obtaining end 276 located just proximal of the cutting blade 262 provides direct continuous endoscopic visualization of the cutting procedure through slot 266 which comes into alignment with slot 226 of the cannula. The cutting edge of cutting blade 262 is of sufficient height to cut through the entire thickness of the transverse carpal ligament T, and the cutting member 214 is advanced distally within the cannula 212 a sufficient distance for the cutting blade 262 to cut through the entire width of the ligament T. Cutting through the entire thickness and width of the transverse carpal ligament T can be confirmed endoscopically by the endoscope 216 through the slot 266 of the cutting member 214 which is aligned with the slot 226 of the cannula 212. In addition, the slots 269 of the cutting member 214 come into alignment with the slots 230a and 230c of the cannula 212 to allow endoscopic visualization therethrough. Once the cutting blade 262 has cut through the distal edge 94 of the ligament T, the surgeon will typically feel a reduction in resistance or pressure on the cutting member 214 which serves as a tactile indication that the ligament has been completely divided. This tactile sensation can serve as an indicator to the surgeon to discontinue distal advancement of the cutting member 214. Distal advancement of the cutting member 214 can also be controlled or limited to a safe distance by abutment of the cutting member 214 with the cannula 212 as discussed above. The rim formations 237 and indicia 241 may also be of assistance in gauging the amount of distal advancement required for the cutting member 214 to effectuate complete division of the ligament T. Subsequent to the cutting procedure, and at any time during the cutting procedure, the endoscope 216 can be moved longitudinally and/or rotatably within the cutting member 214 to visualize the operative site through the slots 266, 269 and 269 of the cutting member which are in alignment with the slots 226, 230a and 230c of the cannula, and/or through the window 252 of the cannula. The cutting member 214 and endoscope 216 can be removed from the cannula 212 subsequent to the cutting procedure and the endoscope alone can be inserted in the cannula for visualization through slots 226, 230a, 23b, 230c and/or window 252. Once complete division of the transverse carpal ligament T has been confirmed endoscopically, the cutting and visualization instrument assembly 210 is withdrawn through the incision 84. The incision 84 may then be closed with an absorbable intracuticular suture and a bulky dressing may be applied with an Ace wrap for about 24 hours. Subsequently, all dressings can be removed and light activity can be resumed. At about one week post-surgery, the patient may return to work and after three weeks post-surgery strenuous activity may be resumed.

The instruments and method disclosed herein allow minimally invasive carpal tunnel release to be performed while avoiding injury to the specialized skin and superficial fascia of the palm and wrist; ensuring the safety of vital anatomical structures of the wrist and hand; avoiding blind entry and the blind insertion of instruments into the carpal tunnel; creating and/or enlarging the subligamentous space without penetrating or becoming snagged in or on the flexor tendon synovial sheath; facilitating separation of the flexor tendon synovial sheath from the transverse carpal ligament; removing adhered synovium from the lower surface of the transverse carpal ligament; providing redundant endoscopic confirmation of anatomical features and correct positioning of instruments; providing enhanced quality of endoscopic imagery as well as endoscopic fields of view in all important directions; maintaining correct placement and orientation of the instruments; eliminating the need for rigid hyper extension of the wrist during the procedure; providing controlled, guided cutting along a pre-established cutting line; and providing continuous endoscopic visualization of the ligament being divided as well as endoscopic confirmation of complete division of the ligament.

Inasmuch as the present invention is subject to various modifications, additions or changes in detail, the preferred embodiments described herein should be considered illustrative only and should not be taken in a limiting sense since various modifications can be made thereto without departing from the intended scope of the invention as defined by the appended claims.

What is claimed is:

1. An instrument for use in minimally invasive carpal tunnel release wherein the transverse carpal ligament is severed with the assistance of endoscopic visualization, said instrument comprising a cannula for insertion in a distal direction along the subligamentous plane beneath the transverse carpal ligament, said cannula including an open proximal end, a closed distal tip, an elongate tubular member between said proximal end and said distal tip, said tubular member having a central longitudinal axis, a proximal length portion, a distal length portion joined to said distal tip, and a longitudinal interior passage in communication with said proximal end, a slot in said tubular member in communication with said passage and extending longitudinally along said proximal length portion and said distal length portion in parallel with said central longitudinal axis, said slot along said distal length portion being positionable beneath the entire width of the transverse carpal ligament from a proximal edge of the ligament to a distal edge of the ligament, and a blade housing extending exteriorly outwardly from said tubular member along said proximal length portion and enclosing an interior channel extending entirely through said blade housing in communication with said slot, said blade housing having an open proximal end in communication with said channel and an open forward end in communication with said channel, said slot having a closed forward end on said distal length portion of said tubular member a sufficient distance distally of said forward end of said blade housing for the entire width of the transverse carpal ligament to be accommodated between said forward end of said blade housing and said forward end of said slot when said slot along said distal length portion is positioned beneath the transverse carpal ligament, said tubular member being of sufficient length for said slot along said distal length portion to be positioned beneath the entire width of the transverse carpal ligament with said proximal length portion extending through an incision in the mid-volar forearm; and a cutting member slidably receivable in said cannula, said cutting member including an elongate tube having a central longitudinal axis, a lumen extending longitudinally through said tube for slidably and rotatably receiving an endoscope, a cutting blade extending exteriorly outwardly from an outer surface of said tube, and at least one fenestration in said tube in communication with said lumen and extending longitudinally in parallel with said central longitudinal axis of said tube proximally of said cutting blade, said tube being slidable longitudinally in said passage of said cannula with said cutting blade extending through said slot to extend exteriorly outwardly from said tubular member and into said interior channel of said blade housing when disposed longitudinally along said proximal length portion of said tubular member, said blade being movable longitudinally distally from said forward end of said blade housing along said slot to expose said blade extending exteriorly outwardly from said tubular member to sever the transverse carpal ligament disposed over said slot along said distal length portion of said tubular member, said blade being slidable within said slot from said forward end of said blade housing toward said forward end of said slot to sever the entire width of the transverse carpal ligament in the distal direction from the proximal edge to the distal edge of the ligament, said fenestration being aligned in parallel with said slot as said blade is moved distally from said forward end of said blade housing to permit an endoscope within said tube to visualize the ligament being severed through said fenestration and said slot aligned therewith.

2. The instrument recited in claim 1 wherein said distal tip has an external configuration tapering distally from said tubular member to a distal terminus.

3. The instrument recited in claim 1 wherein said forward end of said blade housing is configured to hold in place the proximal edge of the transverse carpal ligament disposed over said slot along said distal length portion of said tubular member.

4. The instrument recited in claim 1 wherein at least said distal tip and said distal length portion of said tubular member are of a transparent material to permit visualization therethrough by an endoscope within said cannula.

5. The instrument recited in claim 1 wherein said slot is a volar slot and said cannula further includes a dorsal slot in said tubular member along a bottom of said cannula, a radial slot in said tubular member along a side of said cannula, and an ulnar slot in said tubular member along a side of said cannula opposite said radial slot, said dorsal, radial and ulnar slots each having a closed forward end on said distal length portion and extending longitudinally along said distal length portion in parallel with said central longitudinal axis of said tubular member, said dorsal, radial and ulnar slots being in communication with said passage, said slots permitting visualization therethrough by an endoscope rotatably disposed within said cannula.

6. The instrument recited in claim 5 wherein said fenestration is a volar fenestration and said cutting member further includes a radial fenestration and an ulnar fenestration in said tube extending longitudinally in parallel with said central longitudinal axis of said tube and being in communication with said lumen, said radial fenestration and said ulnar fenestration being in respective alignment in parallel with said radial slot and said ulnar slot in said cannula when said blade is disposed in said volar slot to permit endoscopic visualization through said fenestrations and said slots aligned therewith by an endoscope rotatably disposed within said cutting member.

7. The instrument recited in claim 5 wherein said cannula further includes a plurality of exterior protuberances on said tubular member extending longitudinally in parallel with said central longitudinal axis of said tubular member, said plurality of protuberances including a protuberance between each pair of adjacently located ones of said slots.

8. The instrument recited in claim 1 wherein said cannula further includes a plurality of interior ribs on said tubular member projecting into said interior passage, said ribs extending longitudinally at least substantially the entire length of said interior passage in parallel with said central longitudinal axis of said tubular member at spaced radial locations about said central longitudinal axis of said tubular member.

9. The instrument recited in claim 1 wherein said cannula further includes a plurality of reference formations on an exterior surface of said distal length portion of said tubular member at longitudinally spaced locations along said distal length portion, said reference formations being raised from said exterior surface of said tubular member and being located on said distal length portion to provide an indication of the distance that said blade is moved distally from said forward end of said blade housing.

10. The instrument recited in claim 9 wherein said cannula further includes indicia on said distal length portion of said tubular member to distinguish each of said reference formations.

11. The instrument recited in claim 1 wherein said blade housing includes a pair of side walls having lower ends respectively joined to said tubular member on opposite sides of said slot, said side walls extending longitudinally along said slot and extending exteriorly outwardly from said tubular member.

12. An instrument for use in minimally invasive carpal tunnel release wherein the transverse carpal ligament is severed with the assistance of endoscopic visualization, said instrument comprising a cannula for insertion in the carpal tunnel in a distal direction along the subligamentous plane between the transverse carpal ligament and the flexor tendon synovial sheath, said cannula having an open proximal end, a closed hollow distal tip, an elongate tubular member between said proximal end and said distal tip, said tubular member having a central longitudinal axis, a proximal length portion, a distal length portion joined to said distal tip, a longitudinal interior passage within said tubular member in communication with said open proximal end, a window opening in said distal tip along a top of said cannula in communication with said passage, a longitudinal slot in said tubular member extending along said proximal length portion and said distal length portion in communication with said passage along said top of said cannula, said slot along said distal length portion being positionable beneath the entire width of the transverse carpal ligament from a proximal edge of the ligament to a distal edge of the ligament, and a blade housing extending along said proximal length portion and having an interior channel extending entirely therethrough in communication with said slot, said blade housing having an open proximal end in communication with said channel and an open forward end in communication with said channel, said slot having an open rearward end at said proximal end of said cannula and having a closed forward end on said tubular member adjacent said distal tip, said forward end of said slot being a sufficient distance distally of said forward end of said blade housing for the entire width of the transverse carpal ligament to be accommodated between said forward end of said blade housing and said forward end of said slot when said slot along said distal length portion is positioned beneath the transverse carpal ligament, said distal tip having an external configuration tapering distally in height from said tubular member to a distal terminus, said distal tip having an upper wall segment along said top of said cannula extending distally from said tubular member to said distal terminus and having a lower wall segment along a bottom of said cannula extending distally at an upward angle from said tubular member to said distal terminus, said height of said external configuration of said distal tip being defined between said upper and lower wall segments, said external configuration of said distal tip facilitating insertion of said cannula from proximal to distal along the subligamentous plane between the flexor tendon synovial sheath and the transverse carpal ligament to position said slot along said distal length portion of said tubular member beneath the transverse carpal ligament, said tubular member being of sufficient length for said slot along said distal length portion to be positioned beneath the entire width of the transverse carpal ligament with said proximal length portion extending through an incision in the mid-volar forearm; and a cutting member slidably receivable in said cannula, said cutting member including an elongate tube slidably receivable in said passage and having a central longitudinal axis, a lumen extending longitudinally through said tube for slidably and rotatably receiving an endoscope, a cutting blade extending exteriorly outwardly from an outer surface of said tube, and a fenestration in said tube in communication with said lumen, said fenestration extending longitudinally in parallel with said central longitudinal axis of said tube proximally of said cutting blade, said tube being movable longitudinally in said passage with said cutting blade extending through said slot to extend exteriorly outwardly from said tubular member, said cutting blade extending exteriorly outwardly from said tubular member into said channel of said blade housing when disposed longitudinally along said proximal length portion of said tubular member and being movable distally from said forward end of said blade housing along said slot to expose said blade extending exteriorly outwardly from said tubular member to sever the transverse carpal ligament positioned over said slot along said distal length portion of said tubular member, said blade being slidable within said slot from said forward end of said blade housing toward said forward end of said slot to sever the entire width of the transverse carpal ligament in the distal direction from the proximal edge to the distal edge of the ligament, said fenestration being aligned in parallel with said slot as said blade is moved distally from said forward end of said blade housing to permit an endoscope within said tube to visualize the ligament being severed through said fenestration and said slot aligned therewith, said window opening permitting the endoscope within said tube to visualize an area distal of the ligament.

13. The instrument recited in claim 12 wherein said distal tip has a conical external configuration with a base joined to said tubular member and a rounded apex at said distal terminus aligned with a horizontal plane containing said central longitudinal axis of said tubular member.

14. The instrument recited in claim 12 wherein said distal tip has an external configuration defining a width perpendicular to said height, and said width of said external configuration does not taper distally from said tubular member to said distal terminus.

15. The instrument recited in claim 14 wherein said width of said external configuration increases distally from said tubular member to said distal terminus.

16. The instrument recited in claim 12 wherein said distal tip has an external configuration defining a width perpendicular to said height, and said distal terminus extends transverse to said central longitudinal axis of said tubular member in the direction of said width of said external configuration and in alignment with an offset plane that is offset toward said top of said cannula from a horizontal plane containing said central longitudinal axis of said tubular member.

17. The instrument recited in claim 16 wherein said distal terminus is substantially straight transverse to said central longitudinal axis of said tubular member in the direction of said width of said external configuration in said offset plane.

18. The instrument recited in claim 16 wherein said distal terminus is substantially convexly curving transverse to said central longitudinal axis of said tubular member in the direction of said width of said external configuration in said offset plane.

19. An instrument for use in minimally invasive carpal tunnel release wherein the transverse carpal ligament in the wrist is severed with the assistance of endoscopic visualization, said instrument comprising a cannula for slidably receiving a cutting member and an endoscope slidably and rotatably disposed in the cutting member to form a cutting and visualization instrument assembly and for slidably and rotatably receiving an endoscope without a cutting member disposed within said cannula to form a visualization instrument assembly, said cannula having an open proximal end, a closed tapered distal tip having a window opening along a top of said cannula, an elongate tubular member between said open proximal end and said distal tip, said tubular member having a central longitudinal axis, a proximal length portion, a distal length portion joined to said distal tip, and a longitudinal interior passage in communication with said window opening and with said open proximal end, a plurality of slots in said tubular member in communication with said passage and extending longitudinally along said tubular member in parallel with said central longitudinal axis at spaced radial locations about said central longitudinal axis, a plurality of exterior protuberances on said tubular member extending longitudinally at least substantially the entire length of said tubular member in parallel with said central longitudinal axis and with each of said protuberances being located between a pair of adjacently located ones of said slots, and a blade housing extending exteriorly from said tubular member along said top of said cannula, said plurality of slots including a volar slot along said top of said cannula at a volar position relative to the wrist, a dorsal slot along a bottom of said cannula at a dorsal position relative to the wrist, and radial and ulnar slots respectively disposed along opposite sides of said cannula at respective radial and ulnar positions relative to the wrist, said volar slot extending along said proximal length portion and said distal length portion of said tubular member, said volar slot having an open rearward end at said proximal end of said cannula and a closed forward end on said distal length portion adjacent said distal tip, said dorsal slot, said radial slot and said ulnar slot extending along said distal length portion and having closed rearward ends on said distal length portion distal of said blade housing and having closed forward ends on said distal length portion adjacent said distal tip, said tubular member having an approximately square external cross-sectional configuration with four rounded corners defining said protuberances, said volar slot along said distal length portion being positionable beneath the entire width of the transverse carpal ligament from a proximal edge of the ligament to a distal edge of the ligament, said blade housing extending along said proximal length portion of said tubular member and having a channel extending entirely therethrough in communication with said volar slot, said blade housing having an open proximal end in communication with said channel and an open forward end in communication with said channel, said forward end of said volar slot being a sufficient distance distally of said forward end of said blade housing for the entire width of the transverse carpal ligament to be accommodated between said forward end of said blade housing and said forward end of said volar slot when said volar slot along said distal length portion of said tubular member is positioned beneath the transverse carpal ligament, said tubular member being of sufficient length for said volar slot along said distal length portion to be positioned beneath the entire width of the transverse carpal ligament with said proximal length portion extending through an incision in the mid-volar forearm, said window opening and said slots permitting visualization therethrough by an endoscope slidably and rotatably disposed in said passage, said window opening and said slots forming an air interface between an endoscope within said passage and anatomical structure located external to said cannula to facilitate visual identification of the anatomical structure by the endoscope from within said passage; and a cutting member comprising an elongate tube slidably receivable in said passage of said cannula, said tube having a central longitudinal axis, a lumen extending entirely therethrough for slidably and rotatably receiving an endoscope, a blade extending exteriorly outwardly from said tube to slidably extend through said volar slot of said cannula when said tube is slidably received within said passage, and at least one fenestration in said tube extending longitudinally in parallel with said central longitudinal axis of said tube proximal of said blade, said blade extending through said volar slot to extend exteriorly outwardly from said tubular member and into said channel of said blade housing when disposed along said proximal length portion of said tubular member, said blade being movable distally from said forward end of said blade housing along said volar slot along said distal length portion of said tubular member in response to longitudinal distal movement of said tube within said passage to expose said blade extending exteriorly outwardly from said tubular member to sever the transverse carpal ligament disposed over said volar slot along said distal length portion of said tubular member, said blade being slidable within said volar slot from said forward end of said blade housing toward said forward end of said volar slot to sever the entire width of the transverse carpal ligament in the distal direction from the proximal edge to the distal edge of the ligament along a cutting line defined by said volar slot, said fenestration being aligned in parallel with said volar slot as said blade is moved distally from said forward end of said blade housing to permit the endoscope within said tube to visualize the ligament being severed through said fenestration and said volar slot aligned therewith, said fenestration and said volar slot aligned therewith forming an air interface between an endoscope within said tube and the anatomical structure located external to said cannula to facilitate visual identification of the anatomical structure by the endoscope through said fenestration and said volar slot aligned therewith, said external cross-sectional configuration of said tubular member resisting rotation of said cannula when positioned beneath the transverse carpal ligament and during severance of the ligament in the distal direction.

20. The instrument recited in claim 19 wherein said fenestration is a volar fenestration and said cutting member further includes a radial fenestration in said tube and an ulnar fenestration in said tube, said radial and ulnar fenestrations extending longitudinally in parallel with said central longitudinal axis of said tube and being respectively aligned in parallel with said radial and ulnar slots of said cannula when said tube is moved longitudinally distally within said passage to permit visualization therethrough by the endoscope from within said tube, said radial and ulnar fenestrations respectively aligned with said radial and ulnar slots forming an air interface between the endoscope within said tube and the anatomical structure located external to said cannula to facilitate visual identification of the anatomical structure by the endoscope through said fenestrations and said slots aligned therewith.

* * * * *